US008741899B2

(12) United States Patent
Zhang et al.

(10) Patent No.: US 8,741,899 B2
(45) Date of Patent: *Jun. 3, 2014

(54) (4-CHLORO-2-FLUORO-N-(2-FLUOROPHENYL)-5-[(8AR)-HEXAHYDROPYRROLO-[1,2-A]PYRAZIN-2(1H)-YLCARBONYL]-BENZENESULFONAMIDE, AND PHARMACEUTICALLY ACCEPTABLE SALTS THEREOF

(71) Applicant: AbbVie Inc., North Chicago, IL (US)

(72) Inventors: Qingwei Zhang, Libertyville, IL (US); Andrew O. Stewart, Libertyville, IL (US); Zhiren Xia, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,615

(22) Filed: Feb. 4, 2013

(65) Prior Publication Data

US 2013/0210827 A1    Aug. 15, 2013

Related U.S. Application Data

(63) Continuation of application No. 13/323,029, filed on Dec. 12, 2011, now Pat. No. 8,404,719, which is a continuation of application No. 12/687,465, filed on Jan. 14, 2010, now Pat. No. 8,101,614.

(60) Provisional application No. 61/144,899, filed on Jan. 15, 2009.

(51) Int. Cl.
*A61K 31/495* (2006.01)

(52) U.S. Cl.
USPC .......................... 514/249; 544/349

(58) Field of Classification Search
USPC .......................... 514/249; 544/349
See application file for complete search history.

(56) References Cited

U.S. PATENT DOCUMENTS

| 8,420,823 | B2 | 4/2013 | Jitsuoka et al. |
| 2005/0148587 | A1 | 7/2005 | Fraser et al. |

FOREIGN PATENT DOCUMENTS

| CN | 1741986 A | 3/2006 |
| WO | 0059882 A1 | 10/2000 |
| WO | 2004065351 A1 | 8/2004 |
| WO | 2004089896 A1 | 10/2004 |
| WO | 2006105127 A2 | 10/2006 |
| WO | 2006105127 A3 | 10/2006 |
| WO | 2009131065 A1 | 10/2009 |
| WO | 2010083264 A1 | 7/2010 |
| WO | WO 2010/083264 | * 7/2010 |

OTHER PUBLICATIONS

Wolff, Manfred E., Ed. Burger's Medicinal Chemistry and Drug Discovery—Fifth Edition, New York: John Wiley & Sons, 1996, vol. 1, 975-976.*
Jordan, V. C. Nature Reviews: Drug Discovery, 2, 2003, 205.*
Angeli et al., "Calcium channel blockade to prevent stroke in hypertension," Am J. Hypertension, 2004 17(9), 817-822.
Arulmozhi et al., "Migraine: Current concepts and emerging therapies," Vascular Pharmacology, 2005, 43, 176-187.
Bao et al., "Differences in Ca2+ Channels Governing Generation of Miniature and Evoked Excitatory Synaptic Currents in Spinal Laminae I and II ," J. Neurosci, 1998, 18(21), 8740-8750.
Barone et al., "SB 201823-A Antagonizes Calcium Currents in Central Neurons and Reduces the Effects of Focal Ischemia in Rats and Mice," Stroke, 1995, 26, 1683-1690.

(Continued)

*Primary Examiner* — Douglas M Willis

(57) ABSTRACT

The present application relates to calcium channel inhibitors comprising compounds of formula (I), formula (II), formula (III), or formula (IV), wherein $L^1$, $R^1$, $R^2$, $R^3$, $R^4$, $R^5$, $R^6$, $R^7$ and $R^c$ are as defined in the specification. The present application also relates to compositions comprising such compounds, and methods of treating conditions and disorders using such compounds and compositions.

2 Claims, No Drawings

(56) References Cited

OTHER PUBLICATIONS

Bell, "Cell-Specific Alternative Splicing Increases Calcium Channel Current Density in the Pain Pathway," Neuron, 2004, 41(1), 127-138.
Berge et al., "Pharmaceutical Salts," J. Pharmaceutical Sciences, 1977, 66(1), 1-19.
Beuckmann et al., "N-Type Calcium Channel α1B Subunit (CaV2.2) Knock-Out Mice Display Hyperactivity and Vigilance State Differences," J. Neurosci, 2003, 23(17), 6793-6797.
Bhatia et al., "Fresh and globular amyloid β protein (1-42) induces rapid cellular degeneration: evidence for AβP channel-mediated cellular toxicity," FASEB J., 2000, 14(9), 1233-1243.
Bhattacharjee et al., "T-Type Calcium Channels Facilitate Insulin Secretion by Enhancing General Excitability in the Insulin-Secreting β-Cell Line, INS-1," Endocrinology, 1997, 138(9), 3735-3740.
Bilici et al., "Protective Effect of T-Type Calcium Channel Blocker in Histamine-Induced Paw Inflammation in Rat," Pharmacological Research, 2001, 44(6), 527-531.
Bowersox et al., Selective N-Type Neuronal Voltage-Sensitive Calcium Channel Blocker, SNX-111, Produces Spinal Antinociception in Rat Models of Acute, Persistent and Neuropathic Pain, J. Pharmacol. Experimental Therapeutics, 1996, 279(3), 1243-1249.
Castiglioni et al., "Alternative splicing in the C-terminus of CaV2.2 controls expression and gating of N-type calcium channels," J. Physiol, 2006, 576(1), 119-134.
Cavalli et al., "Multi-target-Directed Ligands to Combat Neurodegenerative Diseases," J. Med. Chem. 2008, 51(3), 347-372.
Chaplan et al., "Quantitative assessment of tactile allodynia in the rat paw," J. Neuroscience Methods, 1994, 53, 55-63.
Chaplan et al., "Role of Voltage-Dependent Calcium Channel Subtypes in Experimental Tactile Allodynia," J. Pharmacol. Experimental Therapeutics, 1994, 269(3), 1117-1123.
Cizkova et al., "Localization of N-type CA2+ channels in the rat spinal cord following chronic constrictive nerve injury," Exp. Brain Res., 2002, 147, 456-463.
Colbourne et al., "Continuing Postischemic Neuronal Death in CA1: Influence of Ischemia Duration and Cytoprotective Doses of NBQX and SNX-111 in Rats," Stroke, 1999, 30(3), 662-668.
Croom et al, "Modified-release nifedipine: a review of the use of modified-release formulations in the treatment of hypertension and angina pectoris," Drugs, 2006, 66 (4), 497-528.
Darszon et al., "Ion Channels in Sperm Physiology," Physiological Reviews, 1999, 79(2), 481-510.
Dolphin, "A short history of voltage-gated calcium channels," Brit. J. Pharmacology, 2006, 147, S56-S62.
Dorwald, "Side Reactions in Organic Synthesis," 2005 Wiley-VCH Verlag GmbH & KGaA, Weinheim, Preface.
Evans et al., "Differential regulation of evoked peptide release by voltage-sensitive calcium channels in rat sensory neurons," Brain Res. 1996, 712 (2), 265-273.
Feng et al., "Determinants of Inhibition of Transiently Expressed Voltage-gated Calcium Channels by ω-Conotoxins GVIA and MVIIA," J. Biol. Chem. 2003, 278(22), 20171-20178.
Geldenhuys et al., "Structure-activity relationships of pentacycloundecylamines at the N-methyl-D-aspartate receptor," Bioorganic and Medicinal Chemistry, 2007, 15, 1525-1532.
Gitlin, "Treatment-resistant bipolar disorder," Molecular Psychiatry, 2006, 11, 227-240.
Gladstone et al., "Current and emerging treatment options for migraine and other primary headache disorders," Expert Rev. Neurotherapeutics, 2003, 3(6), 845-872.
Gould et al., "Antischizophrenic drugs of the diphenylbutylpiperidine type act as calcium channel antagonists," PNAS USA, 1983, 80, 5122-5125.
Gray et al, "Neuronal calcium channels: Splicing for optimal performance," Cell Calcium, 2007, 42 (4-5), 409-417.
Hatakeyama et al., "Differential nociceptive responses in mice lacking the α1B subunit of N-type Ca2+ channels," Neuroreport, 2001, 12(11), 2423-2427.
Heineman et al., Extracellular Free Calcium and Potassium during Paroxysmal Activity in the Cerebral Cortex of the Cat, Exp. Brain Res., 1977, vol. 27, 237-243.
Heinke et al., "Pre- and postsynaptic contributions of voltage-dependent Ca2+ channels to nociceptive transmission in rat spinal laminal neurons," Eur. J. Neurosci, 2004 19(1), 103-111.
Ino et la., "Functional disorders of the sympathetic nervous system in mice lacking the α1B subunit (Cav 2.2) of N-type calcium channels," PNAS USA, 2001, 98(9), 5323-5328.
International Preliminary Report on Patentability issued for related PCT Application Serial No. PCT/US2010/020964 dated Jul. 19, 2011 (9 pages).
IUPAC "Rules for the Nomenclature of Organic Chemistry, Section E: Stereochemistry," Pure & Appl. Chem., 1976, 4(1-B), 13-30.
Jiang et al., "Palladium-Catalyzed Aromatic Carbon-Nitrogen Bond Formation," Metal-Catalyzed Cross-Coupling Reactions, vol. 1, Wiley & Sons, 2nd Edition, 2004, Chapter 13, p. 699-760 (Index only).
Jordan, "Tamoxifen: A Most Unlikely Pioneering Medicine," Nature Reviews: Drug Discovery, 2, 2003, 205-213.
Kim et al., "Altered Nociceptive Response in Mice Deficient in the α1B Subunit of the Voltage-Dependent Calcium Channel," Mol. Cell. Neurosci, 2001, 18(2), 235-245.
Ley et al., "Modern Synthetic Methods for Copper-Mediated C(aryl)-O, C(aryl)-N, and C(aryl)-S Bond Formation," Angew. Chem. Int. 2003, 42(44), 5400-5449.
Little et al., "Calcium Channel Antagonists Decrease the Ethanol Withdrawal Syndrome," Life Sciences, 1986, 39(22), 2059-2065.
Liu et al., "In Vivo Analysis of Voltage-Dependent Calcium Channels," J. Bioenerg. Biomembr, 2003, 35(6), 671-685.
Lorton et al., "β-Amyloid-induced IL-1β release from an activated human monocyte cell line is calcium-and G-protein-dependent," Mech. Aging Dev., 1997, 94 (1-3), 199-211.
Luebke et al., "Multiple Calcium Channel Types Control Glutamatergic Synaptic Transmission in the Hippocampus," Neuron, 1993, 11(5), 895-902.
Luo et al., "Upregulation of Dorsal Root Ganglion α2δ Calcium Channel Subunit and its Correlation with Allodynia in Spinal Nerve-Injured Rats," J. Neurosci, 2001, 21(6), 1868-1875.
Malmberg et al., "Voltage-Sensitive Calcium Channels in Spinal Nociceptive Processing: Blockade of N- and P-Type Channels Inhibits Formalin-induced Nociception," J. Neurosci, 1994, 14(18), 4882-4890.
Mason et al., "Antioxidant and Cytoprotective Activities of the Calcium Channel Blocker Mibefradil," Biochemical Pharmacology, 1998, 55(11), 1843-1852.
Matthews et al., "Effects of spinally delivered N- and P-type voltage-dependent calcium channel antagonists on dorsal horn neuronal responses in a rat model of neuropathy," Pain, 2001, 92 (1-2), 235-246.
McGivern et al., "Targeting N-type and T-type calcium channels for the treatment of pain," Drug Discovery Today, 2006, 11(5/6), 245-253.
Miljanich et al., "Antagonists of Neuronal Calcium Channels: Structure, Function, and Therapeutic Implications," Annu. Rev. Pharmacol. Toxicol, 1995, 35, 707-734.
Newton et al., "Dorsal root ganglion neurons show increased expression of the calcium channel α2δ-1 subunit following partial sciatic nerve injury," Mol. Brain. Res., 2001, 95(1-2), 1-8.
Olivera et al., "Calcium channel Diversity and Neurotransmitter Release: The ω-Conotoxins and ω-Agatoxins," Annu. Rev. Biochem., 1994, 63, 823-867.
Otoom et al., "Nifedipine inhibits picrotoxin-induced seizure activity: further evidence on the involvement of L-type calcium channel blockers in epilepsy," Fundamental and Clinical Pharmacology, 2006, 20, 115-119.
Pietrobon, "Function and dysfunction of synaptic calcium channels: insights from mouse models," Curr. Opin. Neurobiol, 2005, 15 (3), 257-265.
Prescott, "Lipid Vesicles as Carriers for Introducing Biologically Active Materials Into Cells," Methods in Cell Biology, 1976, Academic Press, Chapter 4, 33-71.

(56) References Cited

OTHER PUBLICATIONS

Raingo et al., "Alternative splicing controls G protein-dependent inhibition of N-type calcium channels in nociceptors," Nat. Neurosci, 2007, 10(3), 285-292.

Rodnitzky et al., "Can Calcium Antagonists Provide a Neuroprotective Effect in Parkinson's Disease?" Drugs, 1999, 57(6), 845-849.

Saade et al., "The L-type calcium channel blocker nimodipine mitigates 'learned helplessness' in rats," Pharmacology, Biochemistry and Behavior, 2003, 74, 269-278.

Saegusa et al., "Suppression of inflammatory and neuropathic pain symptoms in mice lacking the N-type Ca2+ channel," EMBO J, 2001 20(10), 2349-2356.

Schlummer et al., "Palladium-Catalyzed C—N and C—O Coupling—A Practical Guide for an Industrial Vantage Point," Adv. Synth. Catal., 2004, 346, 1599-1626.

Scott et al., "Actions of intrathecal omega-conotoxins CVID, GVIA, MVIIA, and morphine in acute and neuropathic pain in the rat," Eur. J. Pharmacol., 2002, 451(3), 279-286.

Shin et al., "T-type Ca2+ channels as therapeutic targets in the nervous system," Curr Opin Pharmacol, 2008, 8(1), 33-41.

Smith et al., "The novel N-type calcium channel blocker, AM336, produces potent dose-dependent antinociception after intrathecal dosing in rats and inhibits substance P release in rat spinal cord slices," Pain 2002, 96(1-2), 119-127.

Takahashi et al., "Different types of calcium channels mediate central synaptic transmission," Nature, 1993, 366(6451), 156-158.

Takei et al, "Increased sensitivity to halothane but decreased sensitivity to propofol in mice lacking the N-type Ca2+ channel," Neurosci. Lett, 2003, 350(1), 41-45.

Tort et al., "Atypical antipsychotic profile of flunarizine in animal models," Psychopharmacology, 2005, 177(3), 344-348.

Urban et al., "Medullary N-type and P/Q-type calcium channels contribute to neuropathy-induced allodynia," Neuroreport, 2005, 16(6), 563-566.

Vagnucci et al., "Alzheimer's disease and angiogenesis," Lancet, 2003, 361(9357), 605-608.

Veng et al., "Age-related working memory impairment is correlated with increases in the L-type calcium channel protein alpha1D (Cav1.3) in area CA1 of the hippocampus and both are ameliorated by chronic nimodipine treatment," Molecular Brain Research, 2003, 110(2), 193-202.

Vezzani et al., "Effect of various calcium channel blockers on three different models of limbic seizures in rats," Neuropharmacology, 1988, 27(5), 451-458.

Wang et al., "Effects of intrathecal administration of ziconotide, a selective neuronal N-type calcium channel blocker, on mechanical allodynia and heat hyperalgesia in a rat model of postoperative pain," Pain 2000, 84 (2-3), 151-158.

Westenbrook et al., "Localization of Ca2+ Channel Subtypes on Rat Spinal Motor Neurons, Interneurons, and Nerve Terminals," J. Neurosci, 1998, 18 (16), 6319-6330.

Wolff, Burger's Medicinal Chemistry and Drug Discovery, 5$^{th}$ Ed., John Wiley & Sons, 1996, 975-976.

Yokoyama et al., "Plastic Change of N-type Ca Channel Expression after Preconditioning is Responsible for Prostaglandin E2-induced Long-lasting Allodynia," Anesthesiology, 2003, 99(6), 1364-1370.

Zanchetti et al., "Calcium Antagonist Lacidipine Slows Down Progression of Asymptomatic Carotid Atherosclerosis," Circulation, 2002, 106, 2422-2427.

\* cited by examiner

US 8,741,899 B2

(4-CHLORO-2-FLUORO-N-(2-FLUOROPHENYL)-5-[(8AR)-HEXAHYDROPYRROLO-[1,2-A]PYRAZIN-2(1H)-YLCARBONYL]-BENZENESULFONAMIDE, AND PHARMACEUTICALLY ACCEPTABLE SALTS THEREOF

CROSS-REFERENCE SECTION TO RELATED APPLICATIONS

This application is a continuation of U.S. patent application Ser. No. 13/323,029, filed on Dec. 12, 2011, which claims priority to U.S. patent application Ser. No. 12/687,465, filed on Jan. 14, 2010, which claims priority to U.S. patent application Ser. No. 61/144,899, filed Jan. 15, 2009, all of which are incorporated herein by reference in their entirety.

TECHNICAL FIELD

The present invention relates to compounds that are calcium channel blockers, compositions including such compounds, and methods of treating conditions and disorders using such compounds and compositions.

BACKGROUND OF THE INVENTION

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A. C. A short history of voltage-gated calcium channels. British Journal of Pharmacology 2006, 147 (Suppl. 1), S56-S62). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~−30 mV) and are involved in "presynaptic" neurotransmission (McGivern J. G. Targeting N-type and T-type calcium channels for the treatment of pain. Drug Discovery Today 2006, 11, 245-253). T-type channels are activated at relatively negative membrane potentials (~−60 mV) and are primarily involved in "postsynaptic" excitability (Shin, H.-S.; et al. T-type $Ca^{2+}$ channels as therapeutic targets in the nervous system. Curr. Opin. in Pharmacology 2008, 8, 33-41).

N-type channel $α_s$ subunits are encoded by a single gene ($α_1B$ or $Ca_v2.2$) in contrast to pharmacologically defined L- and T-type currents that are encoded by multiple $α_1$-subunit genes. A diversity of N-type channels arises due to extensive alternative splicing of the α subunit gene that generates variants with different expression patterns and GPCR-modulated biophysical properties (Gray, A. C.; et al. Neuronal calcium channels: splicing for optimal performance. Cell Calcium, 2007, 42(4-5), 409-417). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M.; et al. Functional disorders of the sympathetic nervous system in mice lacking the $α_{1B}$ subunit ($Ca_v2.2$) of N-type calcium channels. Proc. Natl. Acad. Sci. USA 2001, 98(9), 5323-5328). In pain pathways, N-type channels are expressed in the rostral ventral medulla, an important site of descending pain modulation (Urban, M. O.; et al. Medullary N-type and P/Q-type calcium channels contribute to neuropathy-induced allodynia. Neuroreport 2005, 16(6), 563-566) and are a major contributor to the synaptic neurotransmission that occurs between C/Aδ nociceptors and spinal lamina I neurons (Bao, J.; et al. Differences in $Ca^{2+}$ channels governing generation of miniature and evoked excitatory synaptic currents in spinal laminae I and II. J. Neurosci. 1998, 18(21), 8740-50. Heinke, B.; et al. Pre- and postsynaptic contributions of voltage-dependent $Ca^{2+}$ channels to nociceptive transmission in rat spinal lamina I neurons. Eur. J. Neurosci. 2004, 19(1), 103-111). In contrast, P/Q type channels are expressed almost exclusively in laminae II-IV of the spinal cord and show little co-localization with Substance P and N-type channels (Westenbroek, R. E.; et al. Localization of $Ca^{2+}$ channel subtypes on rat spinal motor neurons, interneurons, and nerve terminals. J. Neurosci. 1998, 18(16), 6319-6330).

Following nerve injury there is increased expression of $Ca_v2.2$ (Westenbroek, R. E.; et al. Localization of $Ca^{2+}$ channel subtypes on rat spinal motor neurons, interneurons, and nerve terminals. J. Neurosci. 1998, 18(16), 6319-6330. Cizkova, D.; et al. Localization of N-type $Ca^{2+}$ channels in the rat spinal cord following chronic constrictive nerve injury. Exp. Brain Res. 2002, 147, 456-463. Yokoyama, K.; et al. Plastic change of N-type calcium channel expression after preconditioning is responsible for prostaglandin E2-induced long-lasting allodynia. Anesthesiology 2003, 99(6), 1364-1370) and α2δ1 subunits (Luo, Z. D.; et al. Upregulation of dorsal root ganglion α2δ calcium channel subunit and its correlation with allodynia in spinal nerve-injured rats. J. Neurosci. 2001, 21(6), 1868-1875. Newton, R. A.; et al. Dorsal root ganglion neurons show increased expression of the calcium channel α2δ-1 subunit following partial sciatic nerve injury. Mol. Brain. Res. 2001, 95(1-2), 1-8) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T. J.; et al. Cell specific alternative splicing increases calcium channel density in the pain pathway. Neuron 2004, 41(1), 127-138). These channels have distinct electrophysiological properties and current densities (Castiglioni, A. J.; et al. Alternative splicing in the C-terminus of $Ca_v2.2$ controls expression and gating of N-type calcium channels. J. Physiol. 2006, 576(Pt 1), 119-134) compared to wild-type $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; et al. Alternative splicing controls G protein-dependent inhibition of N-type calcium channels in nociceptors. Nat. Neurosci. 2007, 10(3), 285-292). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M.; et al. Functional disorders of the sympathetic nervous system in mice lacking the alpha 1B subunit ($Ca_v2.2$) of N-type calcium channels. Proc. Natl. Acad. Sci. USA 2001, 98(9), 5323-5328. Kim, C.; et al. Altered nociceptive response in mice deficient in the alpha$_{1B}$ subunit of the voltage-dependent calcium channel. Mol. Cell. Neurosci. 2001, 18(2), 235-245. Hatakeyama, S.; et al. Differential nociceptive responses in mice lacking the alpha$_{1B}$ subunit of N-type Ca$^{2+}$ channels. Neuroreport 2001, 12(11), 2423-2427. Liu; L.; et al. In vivo analysis of voltage-dependent calcium channels. J. Bioenerg. Biomembr. 2003, 35(6), 671-685). This finding suggests that other types of Ca$_V$ channels are able to compensate for the lack of Ca$_V$2.2 channels at most synapses in these mice (Pietrobon, D. Function and dysfunction of synaptic calcium channels: insights from mouse models. Curr. Opin. Neurobiol. 2005, 15(3), 257-265). Ca$_V$2.2 deficient mice are resistant to the development of inflammatory and neuropathic pain (Kim, C.; et al. Altered nociceptive response in mice deficient in the alpha$_{1B}$ subunit of the voltage-dependent calcium channel. Mol. Cell. Neurosci. 2001, 18(2), 235-245. Hatakcyama, S.; et al. Differential nociceptive responses in mice lacking the alpha$_{1B}$ subunit of N-type Ca$^{2+}$ channels. Neuroreport 2001, 12(11), 2423-2427. Saegusa, H.; et al. Suppression of inflammatory and neuropathic pain symptoms in mice lacking the N-type calcium channel. EMBO J. 2001, 20(10), 2349-2356), have decreased sympathetic nervous system function Ono, M.; et al. Functional disorders of the sympathetic nervous system in mice lacking the alpha 1B subunit (Ca$_V$2.2) of N-type calcium channels. Proc. Natl. Acad. Sci. USA 2001, 98(9), 5323-5328), and altered responses to both ethanol and anesthetics (Newton, R. A.; et al. Dorsal root ganglion neurons show increased expression of the calcium channel alpha2delta-1 subunit following partial sciatic nerve injury. Brain Res. Mol. Brain. Res. 2001, 95(1-2), 1-8. Takei, R. et al. Increased sensitivity to halothane but decreased sensitivity to propofol in mice lacking the N-type Ca$^{2+}$ channel. Neurosci. Lett. 2003, 350(1), 41-45). Additional behavioral studies indicate that Ca$_V$2.2 knockout mice are less anxious, are hyperactive, and show enhanced vigilance compared to wild-type littermates (Beuckmann, C. T.; et al. N-type calcium channel alpha$_{1B}$ subunit (Ca$_V$2.2) knock-out mice display hyperactivity and vigilance state differences. J. Neurosci. 2003, 23(17), 6793-6797).

N- and P/Q-type channels are localized at neuronal synaptic junctions and contribute significantly to neurotransmitter release (Olivera, B. M.; et al. Calcium channel diversity and neurotransmitter release: the omega-conotoxins and omega agatoxins. Annu Rev. Biochcm. 1994, 63, 823-867. Miljanich, G. P.; et al. Antagonists of neuronal calcium channels: structure, function, and therapeutic implications. Annu. Rev. Pharmacol. Toxicol. 1995, 35, 707-734). N-type channels play a major role in the release of glutamate, acetylcholine, dopamine, norepinephrine, GABA and calcitonin gene-related protein (CGRP). P/Q-type channels may be involved in the release of glutamate, aspartate, 5HT, GABA and probably glycine (Pietrobon, D. Function and dysfunction of synaptic calcium channels: insights from mouse models. Curr. Opin. Neurobiol. 2005, 15(3), 257-265).

L, P/Q and N-type channels are blocked by channel specific antagonists i.e., dihydropyridines, ω-agatoxin IVA and ω-conotoxin MVIIA/ziconotide, respectively. Agatoxin IVa has been shown to block excitatory (Luebke, J. I.; et al. Multiple calcium channel types control glutamatergic synaptic transmission in the hippocampus. Neuron 1993, 11(5), 895-902) as well as inhibitory neurotransmission (Takahashi, T.; et al. Different types of calcium channels mediate central synaptic transmission. Nature 1993, 366(6451), 156-158). Intrathecal injection of selective N-type channel blockers (e.g. conotoxin-derived peptides such as GVIA, MVIIA (ziconotidc), and CVID) significantly attenuates pain responses in animal models of neuropathic pain, formalin-induced pain, and post-operative pain (Chaplan, S. R.; et al. Role of voltage-dependent calcium channel subtypes in experimental tactile allodynia. J. Pharmacol. Exp. Ther. 1994, 269(3), 1117-1123. Malmberg, A. B.; et al. Voltage-sensitive calcium channels in spinal nociceptive processing: blockade of N- and P-type channels inhibits formalin-induced nociception. J. Neurosci. 1994, 14(8), 4882-4890. Bowersox, S. S.; et al. Selective N-type neuronal voltage-sensitive calcium channel blocker, SNX-111, produced spinal antinociception in rat models of acute, persistent and neuropathic pain. J. Pharmacol. Exp. Ther. 1996, 279(3), 1243-1249. Wang, Y. X.; et al. Effects of intrathecal administration of ziconotide, a selective neuronal N-type calcium channel blocker, on mechanical allodynia and heat hyperalgesia in a rat model of postoperative pain. Pain 2000, 84(2-3), 151-158. Scott, D. A.; et al. Actions of intrathecal omega-conotoxins CVID, GVIA, MVIIA, and morphine in acute and neuropathic pain in the rat. Eur. J. Pharmacol. 2002, 451(3), 279-286). These peptide blockers bind to the pore region of the channel, do not show voltage- or frequency-dependent activity, and show irreversible channel block (Feng, Z. P.; et al. Determinants of inhibition of transiently expressed voltage-gated calcium channels by omega-conotoxins GVIA and MVIIA. J. Biol. Chem. 2003, 278(22), 20171-20178). Ziconotide potently blocks neurotransmitter release in the spinal cord dorsal horn (Matthews, E. A.; et al. Effects of spinally delivered N- and P-type voltage-dependent calcium channel antagonists on dorsal horn neuronal responses in a rat model of neuropathy. Pain 2001, 92(1-2), 235-246. Smith, M. T.; et al. The novel N-type calcium channel blocker, AM336, produces potent dose-dependent antinociception after intrathecal dosing in rats and inhibits substance P release in rat spinal cord slices. Pain 2002, 96(1-2), 119-127. Heinke, B.; et al. Pre- and postsynaptic contributions of voltage-dependent Ca$^{2+}$ channels to nociceptive transmission in rat spinal lamina I neurons. Eur. J. Neurosci. 2004, 19(1), 103-111) and in dorsal root ganglion (DRG) neurons (Evans, A. R.; et al. Differential regulation of evoked peptide release by voltage-sensitive calcium channels in rat sensory neurons. Brain Res. 1996, 712(2), 265-273. Smith, M. T.; et al. The novel N-type calcium channel blocker, AM336, produces potent dose-dependent antinociception after intrathecal dosing in rats and inhibits substance P release in rat spinal cord slices. Pain 2002, 96(1-2), 119-127). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S. R.; et al. Role of voltage-dependent calcium channel subtypes in experimental tactile allodynia. J. Pharmacol. Exp. Ther. 1994, 269(3), 1117-1123) or thermal hyperalgesia in the chronic constriction injury model (Yamamoto, T.; et al. Differential effects of intrathecally administered N- and P-type voltage-sensitive calcium channel blockers upon two models of experimental mononeuropathy in the rat. Brain Res. 1998, 794(2), 329-332) of neuropathic pain.

Accordingly, since pain is the most common symptom of disease and the most frequent complaint with which patients present to physicians, there is a need for compounds, such as those of the present invention, that are novel calcium channel blockers that have a utility in treating pain, amongst other conditions.

SUMMARY OF THE INVENTION

The invention is directed to compounds of formula (I) or formula (II)

(I)

[structure I]

(II)

[structure II]

or a pharmaceutically acceptable salt, prodrug, salt of a prodrug, or a combination thereof, wherein one of $R^1$ and $R^2$ is X, and the other of $R^1$ and $R^2$ is Y;

X is (i) or (ii);

(i)

[structure i]

(ii)

[structure ii]

m and n, at each occurrence, are independently 1 or 2;

$G^1$ is azetidinyl, pyrrolidinyl, piperidinyl, morpholinyl, thiomorpholinyl or azepanyl, wherein $G^1$ is connected through the nitrogen atom of said azetidinyl, pyrrolidinyl, piperidinyl, morpholinyl, thiomorpholinyl or azepanyl;

Y is —$NR^cAr^1$, —$NR^cAr^2$—$Ar^1$, —$NR^cCH(Ar^1)_2$, —$NR^c(CR^aR^b)_pAr^1$, —$NR^c(CR^aR^b)_pCH(Ar^1)_2$, —$NR^c$-$G^2$, —$NR^c$-$G^2$-$Ar^1$, (iii), (iv), (v) or (vi);

(iii)

[structure iii]

(iv)

[structure iv]

(v)

[structure v]

(vi)

[structure vi]

$Ar^1$, at each occurrence, is independently aryl or heteroaryl, wherein said aryl and heteroaryl are unsubstituted or substituted with 1, 2, 3, or 4, or 5 substituents selected from alkoxy, alkyl, cyano, haloalkyl, halogen, or —$N(alkyl)_2$;

$Ar^2$ is aryl or heteroaryl, wherein said aryl and heteroaryl are unsubstituted or substituted with 1, 2, 3, or 4 substituents selected from alkoxy, alkyl, cyano, haloalkyl, or halogen;

$G^2$ is cycloalkyl;

$R^a$ and $R^b$ are at each occurrence independently hydrogen, alkyl, or hydroxyalkyl;

$R^c$ is hydrogen or alkyl;

p is 1, 2, 3, or 4; and $R^3$, $R^4$, $R^5$ and $R^6$ are each independently hydrogen, alkoxy, alkyl, or halogen.

The invention is also directed to compounds of formula (III) or formula (IV)

(III)

[structure III]

(IV)

[structure IV]

or a pharmaceutically acceptable salt, prodrug, salt of a prodrug, or a combination thereof, wherein $L^1$ is C(O) or $S(O)_2$;

$R^2$ is X;

X is (i) or (ii);

(i)

[structure i]

-continued

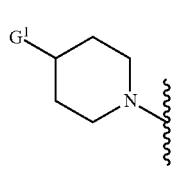
(ii)

m and n, at each occurrence, are independently 1 or 2;

$G^1$ is azetidinyl, pyrrolidinyl, piperidinyl, morpholinyl, thiomorpholinyl or azepanyl, wherein $G^1$ is connected through the nitrogen atom of said azetidinyl, pyrrolidinyl, piperidinyl, morpholinyl, thiomorpholinyl or azepanyl;

$R^3$, $R^4$, $R^5$ and $R^6$ are each independently hydrogen, alkoxy, alkyl, or halogen;

$R^7$ is —S(O)$_2$Ar$^3$, —C(O)Ar$^3$, —S(O)$_2$(CR$^a$R$^b$)$_p$Ar$^3$, —C(O)(CR$^a$R$^b$)$_p$Ar$^3$, —S(O)$_2$(CR$^a$R$^b$)$_p$CH(Ar$^3$)$_2$, —C(O)(CR$^a$R$^b$)$_p$CH(Ar$^3$)$_2$, —C(O)CH(Ar$^3$)$_2$, or —CH(Ar$^3$)$_2$;

Ar$^3$, at each occurrence, is aryl or heteroaryl, wherein said aryl and heteroaryl are unsubstituted or substituted with 1, 2, 3, 4, or 5 substituents selected from alkoxy, alkyl, cyano, haloalkyl, or halogen;

$R^a$ and $R^b$ are at each occurrence independently hydrogen, alkyl, or hydroxyalkyl;

p is 1, 2, 3, or 4; and $R^c$ is hydrogen or alkyl.

Another aspect of the invention relates to pharmaceutical compositions comprising a therapeutically effective amount of compound(s) of the invention or pharmaceutically acceptable salts thereof, in combination with one or more pharmaceutically acceptable carriers. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of formula (I), or a pharmaceutically acceptable salt thereof. The disorders of the central nervous system include stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction, or combinations thereof.

The compounds, compositions comprising the compounds, and methods for treating or preventing conditions and disorders by administering the compounds are further described herein.

DETAILED DESCRIPTION OF THE INVENTION

Compounds of formula (I), formula (II), formula (III), or formula (IV) are disclosed in this invention

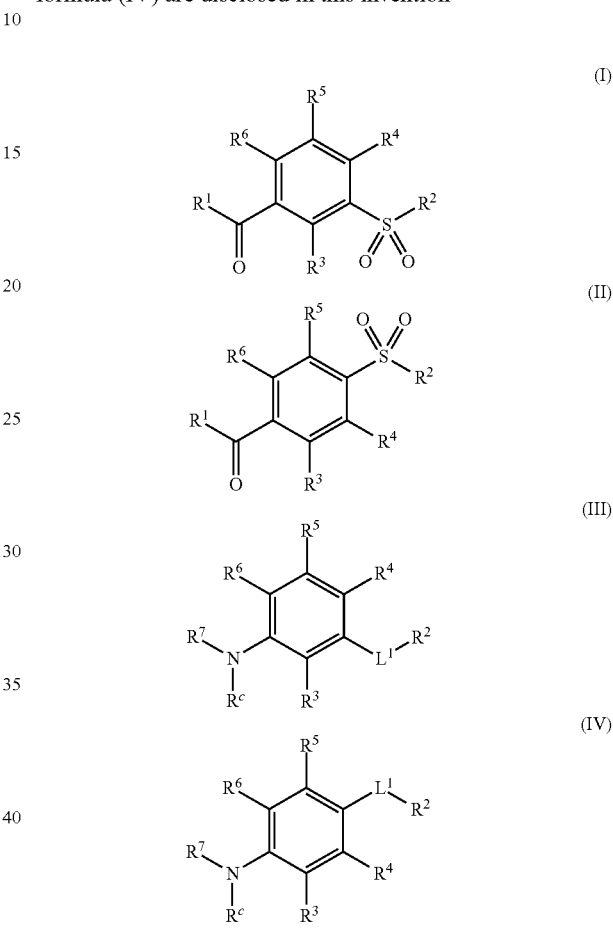

wherein $L^1$, $R^1$, $R^2$, $R^3$, $R^4$, $R^5$, $R^6$, $R^7$, and $R^c$ are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl groups include, but are not limited to, dihydroindenyl, indenyl, naphthyl, dihydronaphthalenyl, and tetrahydronaphthalenyl. The bicyclic awl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroatom" as used herein, means a nitrogen, oxygen, or sulfur atom.

The term "hydroxy" or "hydroxyl" as used herein, means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

b. Compounds

Compounds of the invention have the formula (I), formula (II), formula (III), or formula (IV) as described above.

Particular values of variable groups in compounds of formula (I), formula (II), formula (III), or formula (IV) are as follows. Such values may be used where appropriate with any of the other values, definitions, claims or embodiments defined hereinbefore or hereinafter.

As described generally above for the compounds of formula (I) or formula (II), $R^1$ can be selected from X, wherein X is

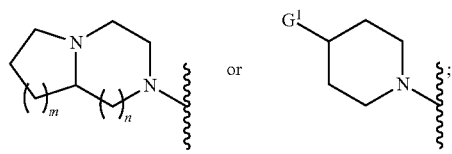

m and n are independently 1 or 2; and $G^1$ is azetidinyl, pyrrolidinyl, piperidinyl, morpholinyl, thiomorpholinyl or azepanyl, wherein $G^1$ is connected through the nitrogen atom of said azetidinyl, pyrrolidinyl, piperidinyl, morpholinyl, thiomorpholinyl or azepanyl.

Thus, compounds within formula (I) or formula (II) include compound of the following formula (V), formula (VI), formula (VII), or formula (VIII) and pharmaceutically acceptable salts thereof:

(V)

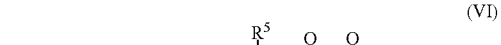

(VI)

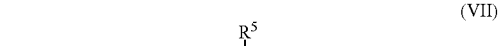

(VII)

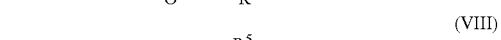

(VIII)

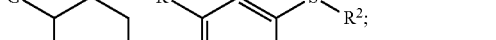

wherein $R^2$ is Y, and Y is selected from —NR$^c$Ar$^1$, —NR$^c$Ar$^2$—Ar$^1$, —NR$^c$CH(Ar$^1$)$_2$, —NR$^c$(CR$^a$R$^b$)$_p$Ar$^1$, —NR$^c$(CR$^a$R$^b$)$_p$CH(Ar$^1$)$_2$, —NR$^c$-G$^2$, —NR$^c$-G$^2$-Ar$^1$, (iii), (iv), (v) or (vi);

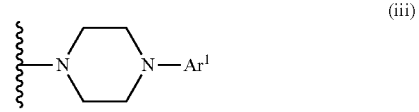

(iii)

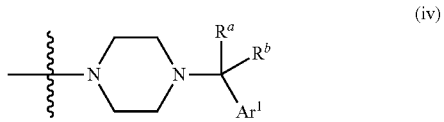

(iv)

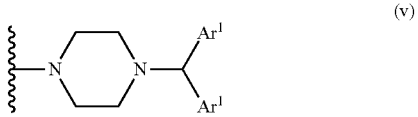

(v)

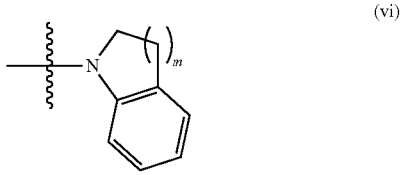

(vi)

Ar$^1$, at each occurrence, is independently aryl or heteroaryl, wherein said aryl and heteroaryl are unsubstituted or substituted with 1, 2, 3, or 4, or 5 substituents selected from alkoxy, alkyl, cyano, haloalkyl, halogen, or —N(alkyl)$_2$; Ar$^2$ is aryl or heteroaryl, wherein said aryl and heteroaryl are unsubstituted or substituted with 1, 2, 3, or 4 substituents selected from alkoxy, alkyl, cyano, haloalkyl, or halogen; $G^2$ is cycloalkyl; $R^a$ and $R^b$ are at each occurrence independently hydrogen, alkyl, or hydroxyalkyl; $R^c$ is hydrogen or alkyl; p is 1, 2, 3, or 4; and $R^3$, $R^4$, $R^5$ and $R^6$ are as disclosed in the Summary of the Invention and the embodiments described herein.

Other compounds formula (I) or formula (II) can include compounds wherein $R^2$ can be selected from X, wherein X is

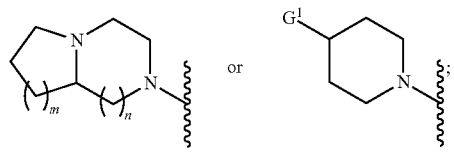

m and n are independently 1 or 2; and $G^1$ is azetidinyl, pyrrolidinyl, piperidinyl, morpholinyl, thiomorpholinyl or azepanyl, wherein $G^1$ is connected through the nitrogen atom of said azetidinyl, pyrrolidinyl, piperidinyl, morpholinyl, thiomorpholinyl or azepanyl.

Thus, compounds within formula (I) or formula (II) include compound of the following formula (IX), formula (X), formula (XI), or formula (XII) and pharmaceutically acceptable salts thereof:

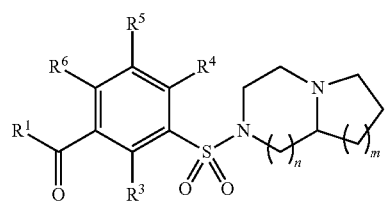

(IX)

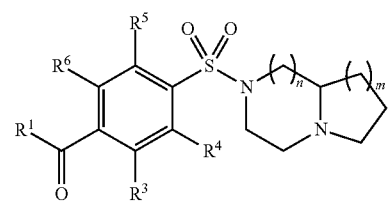

(X)

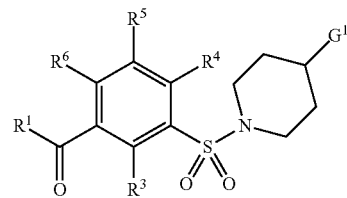

(XI)

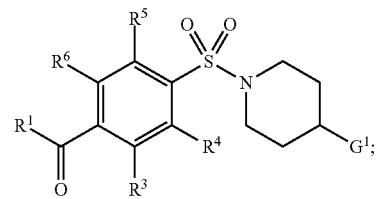

(XII)

wherein $R^1$ is Y, and Y is selected from —$NR^cAr^1$, —$NR^cAr^2$—$Ar^1$, —$NR^cCH(Ar^1)_2$, —$NR^c(CR^aR^b)_pAr^1$, —$NR^c(CR^aR^b)_pCH(Ar^1)_2$, —$NR^c$-$G^2$, —$NR^c$-$G^2$-$Ar^1$, (iii), (iv), (v) or (vi);

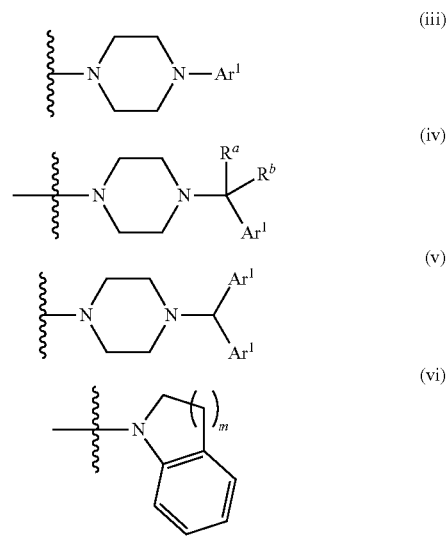

$Ar^1$, at each occurrence, is independently aryl or heteroaryl, wherein said aryl and heteroaryl are unsubstituted or substituted with 1, 2, 3, or 4, or 5 substituents selected from alkoxy, alkyl, cyano, haloalkyl, halogen, or —$N(alkyl)_2$; $Ar^2$ is aryl or heteroaryl, wherein said aryl and heteroaryl are unsubstituted or substituted with 1, 2, 3, or 4 substituents selected from alkoxy, alkyl, cyano, haloalkyl, or halogen; $G^2$ is cycloalkyl; $R^a$ and $R^b$ are at each occurrence independently hydrogen, alkyl, or hydroxyalkyl; $R^c$ is hydrogen or alkyl; p is 1, 2, 3, or 4; and $R^3$, $R^4$, $R^5$ and $R^6$ are as disclosed in the Summary of the Invention and the embodiments described herein.

As described generally above for the compounds of formula (III) or formula (IV), $R^2$ can be selected from X, wherein X is

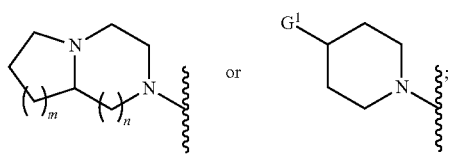

m and n are independently 1 or 2; and $G^1$ is azetidinyl, pyrrolidinyl, piperidinyl, morpholinyl, thiomorpholinyl or azepanyl, wherein $G^1$ is connected through the nitrogen atom of said azetidinyl, pyrrolidinyl, piperidinyl, morpholinyl, thiomorpholinyl or azepanyl.

Thus, compounds within formula (III) or formula (IV) include compound of the following formula (XIII), formula (XIV), formula (XV), or formula (XVI) and pharmaceutically acceptable salts thereof:

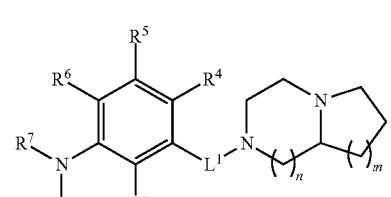

(XIII)

(XIV)

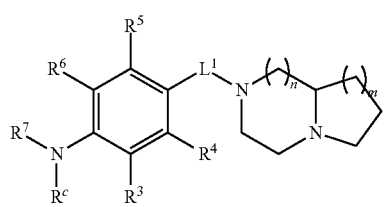

(XV)

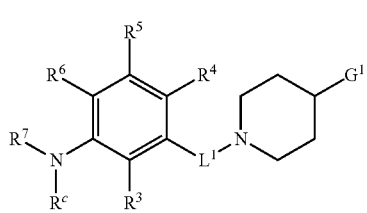

(XVI)

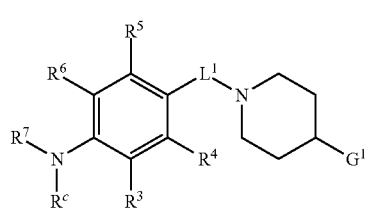

wherein L¹ is C(O) or S(O)₂; R⁷ is S(O)₂Ar³, —C(O)Ar³, —S(O)₂(CRᵃRᵇ)ₚAr³, —C(O)(CRᵃRᵇ)ₚAr³, —S(O)₂(CRᵃRᵇ)ₚCH(Ar³)₂, —C(O)(CRᵃRᵇ)ₚCH(Ar³)₂, —C(O)CH(Ar³)₂, or —CH(Ar³)₂; Arᵃ, at each occurrence, is aryl or heteroaryl, wherein said aryl and heteroaryl are unsubstituted or substituted with 1, 2, 3, 4, or 5 substituents selected from alkoxy, alkyl, cyano, haloalkyl, or halogen; Rᵃ and Rᵇ are at each occurrence independently hydrogen, alkyl, or hydroxyalkyl; p is 1, 2, 3, or 4; and R³, R⁴, R⁵, R⁶ and Rᶜ are as disclosed in the Summary of the Invention and the embodiments described herein.

For each substructure wherein X is

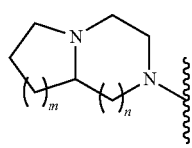

and m and n are independently 1 or 2; there exist the following embodiments which further define the scope of the compounds of the present invention. Accordingly, one aspect of the invention is directed to a group of substructures wherein X is formula (a), (b), (c), or (d).

(a)

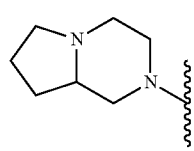

(b)

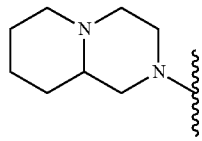

(c)

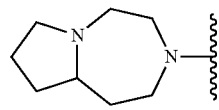

(d)

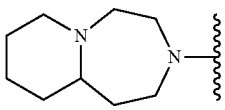

For each substructure wherein X is

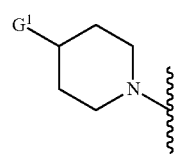

and G¹ is azetidinyl, pyrrolidinyl, piperidinyl, morpholinyl, thiomorpholinyl or azepanyl, wherein G¹ is connected through the nitrogen atom of said azetidinyl, pyrrolidinyl, piperidinyl, morpholinyl, thiomorpholinyl or azepanyl; there exist the following embodiments which further define the scope of the compounds of the present invention. Accordingly, one aspect of the invention is directed to a group of substructures wherein X is formula (e), (f), (g), (h), (i), or (j).

(e)

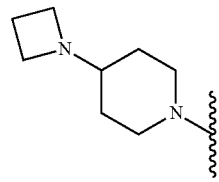

(f)

(g)

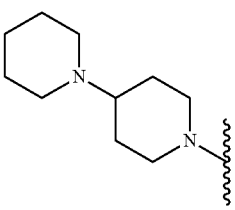

-continued (h)
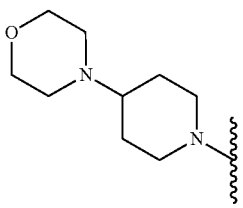

(i)
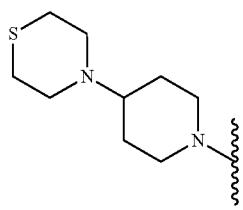

(j)
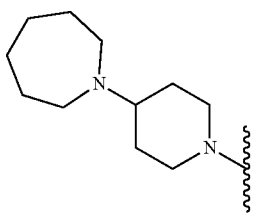

As described generally above for the compounds of formula (I) or formula (II), one of R$^1$ and R$^2$ is selected from Y. Y is selected from —NR$^c$Ar$^1$, —NR$^c$Ar$^2$—Ar$^1$, —NR$^c$CH(Ar$^1$)$_2$, —NR$^c$(CR$^a$R$^b$)$_p$Ar$^1$, —NR$^c$(CR$^a$R$^b$)$_p$CH(Ar$^1$)$_2$, —NR$^c$-G$^2$, —NR$^c$-G$^2$-Ar$^1$, (iii), (iv), (v) or (vi);

(iii)
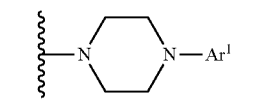

(iv)
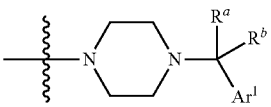

(v)
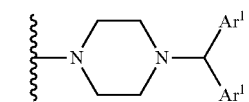

(vi)
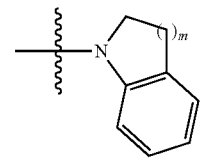

Ar$^1$, at each occurrence, is independently aryl or heteroaryl, wherein said aryl and heteroaryl are unsubstituted or substituted with 1, 2, 3, or 4, or 5 substituents selected from alkoxy, alkyl, cyano, haloalkyl, halogen, or —N(alkyl)$_2$; Ar$^2$ is aryl or heteroaryl, wherein said aryl and heteroaryl are unsubstituted or substituted with 1, 2, 3, or 4 substituents selected from alkoxy, alkyl, cyano, haloalkyl, or halogen; G$^2$ is cycloalkyl; p is 1, 2, 3, or 4.

In one embodiment, G$^2$ is cycloalkyl.
In another embodiment, G$^2$ is cyclopropyl.

In one embodiment, for compounds of formula (I), formula (II), formula (III) or formula (IV), R$^a$ and R$^b$ are at each occurrence independently hydrogen, alkyl, or hydroxyalkyl.

In another embodiment, for compounds of formula (I), formula (II), formula (III) or formula (IV), R$^a$ and R$^b$ are at each occurrence independently hydrogen or hydroxyalkyl.

In a further embodiment, for compounds of formula (I), formula (II), formula (III) or formula (IV), R$^a$ and R$^b$ are at each occurrence hydrogen.

In one embodiment, for compounds of formula (I), formula (II), formula (III) or formula (IV), R$^c$ is hydrogen or alkyl.

In another embodiment, for compounds of formula (I), formula (II), formula (III) or formula (IV), R$^c$ is hydrogen.

In a further embodiment, for compounds of formula (I), formula (II), formula (III) or formula (IV), R$^c$ is alkyl.

In one embodiment for compounds of formula (I), formula (II), formula (III) or formula (IV), R$^3$, R$^4$, R$^5$ and R$^6$ are each independently selected form hydrogen, alkoxy, alkyl, and halogen.

In another embodiment for compounds of formula (I), formula (II), formula (III) or formula (IV), two of R$^3$, R$^4$, R$^5$ and R$^6$ are halogen, and the others are hydrogen.

In another embodiment for compounds of formula (I), formula (II), formula (III) or formula (IV), one of R$^3$, R$^4$, R$^5$ and R$^6$ are alkyl, and the others are hydrogen.

In a further embodiment for compounds of formula (I), formula (II), formula (III) or formula (IV), one of R$^3$, R$^4$, R$^5$ and R$^6$ are halogen, and the others are hydrogen.

In one embodiment for compounds of formula (III) or formula (IV), L$^1$ is C(O) or S(O)$_2$.

In another embodiment for compounds of formula (III) or formula (IV), L$^1$ is C(O).

In a further embodiment for compounds of formula (III) or formula (IV), L$^1$ is S(O)$_2$.

In one embodiment for compounds of formula (III) or formula (IV), R$^7$ is —S(O)$_2$Ar$^3$, —C(O)Ar$^3$, —S(O)$_2$(CR$^a$R$^b$)$_p$Ar$^3$, —C(O)(CR$^a$R$^b$)$_p$Ar$^3$, —S(O)$_2$(CR$^a$R$^b$)$_p$CH(Ar$^3$)$_2$, —C(O)(CR$^a$R$^b$)$_p$CH(Ar$^3$)$_2$, —C(O)CH(Ar$^3$)$_2$, or —CH(Ar$^3$)$_2$; wherein, Ar$^3$, at each occurrence, is aryl or heteroaryl, wherein said aryl and heteroaryl are unsubstituted or substituted with 1, 2, 3, 4, or 5 substituents selected from alkoxy, alkyl, cyano, haloalkyl, or halogen.

In another embodiment for compounds of formula (III) or formula (IV), R$^7$ is —S(O)$_2$Ar$^3$, —C(O)Ar$^3$, —S(O)$_2$(CR$^a$R$^b$)$_p$Ar$^3$, —C(O)(CR$^a$R$^b$)$_p$Ar$^3$.

In a further embodiment, for compounds of formula (III) or formula (IV), R$^7$ is —S(O)$_2$Ar$^3$ or —C(O)Ar$^3$.

In another embodiment for compounds of formula (III) or formula (IV), R$^7$ is —S(O)$_2$(CR$^a$R$^b$)$_p$CH(Ar$^3$)$_2$, —C(O)(CR$^a$R$^b$)$_p$CH(Ar$^3$)$_2$, —C(O)CH(Ar$^3$)$_2$, or —CH(Ar$^3$)$_2$.

In a further embodiment, for compounds of formula (III) or formula (IV), R$^7$ is —C(O)CH(Ar$^3$)$_2$, or —CH(Ar$^3$)$_2$.

In one embodiment for compounds of formula (I) or formula (II), R$^1$ is X, wherein X is

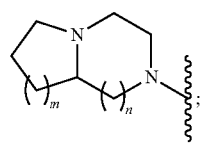

R$^2$ is Y; and Y is —NR$^c$Ar$^1$. In another embodiment for compounds of formula (I), R$^1$ is X, wherein X is

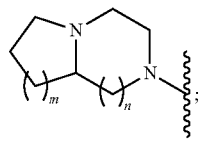

n is 1; R² is Y; and Y is —NR^cAr¹; Ar¹ is aryl; and R³, R⁴, R⁵ and R⁶ are each independently hydrogen or halogen. In one embodiment for compounds of formula (I) or formula (II), R¹ is X, wherein X is

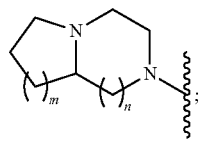

n is 1; R² is Y; and Y is —NR^cCH(Ar¹)₂, —NR^c(CR^aR^b)_pCH(Ar¹)₂, or (v).

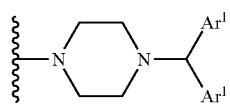
(v)

In another embodiment for compounds of formula (I), R¹ is X, wherein X is

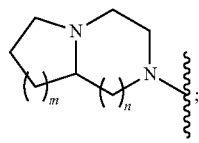

n is 1; R² is Y; and Y is —NR^cCH(Ar¹)₂, —NR^c(CR^aR^b)_pCH(Ar¹)₂, or (v);

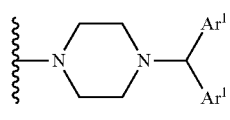
(v)

R^a and R^b are at each occurrence hydrogen; R^c is hydrogen; p is 1, 2 or 3; Ar¹, at each occurrence, is aryl; and R³, R⁴, R⁵ and R⁶ are each independently hydrogen or halogen. In one embodiment for compounds of formula (I) or formula (II), R¹ is X, wherein X is

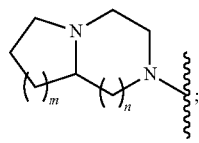

n is 1; R² is Y; and Y is —NR^cAr²—Ar¹, —NR^c(CR^aR^b)_pAr¹, —NR^c-G²-Ar¹, (iii), (iv), or (vi).

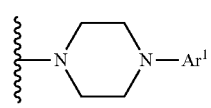
(iii)

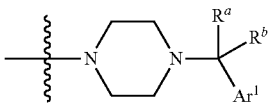
(iv)

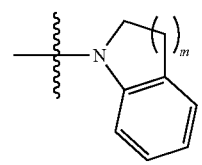
(vi)

In another embodiment for compounds of formula (I), R¹ is X, wherein X is

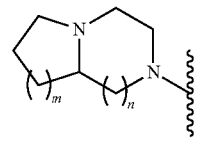

n is 1; R² is Y; and Y is —NR^cAr²—Ar¹, —NR^c(CR^aR^b)_pAr¹, —NR^c-G²-Ar¹, (iii), (iv), or (vi);

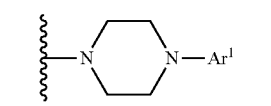
(iii)

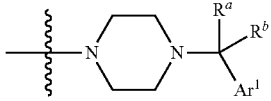
(iv)

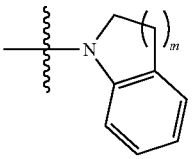
(vi)

R^a and R^b are, at each occurrence, independently hydrogen or hydroxyalkyl; R^c is hydrogen; p is 1, 2 or 3; Ar¹ is aryl; Ar² is aryl; G² is cyclopropyl; and R³, R⁴, R⁵ and R⁶ are each independently hydrogen or halogen. In a further embodiment for compounds of formula (II), R¹ is X, wherein X is

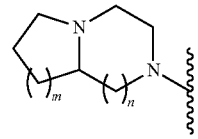

n is 1; R² is Y; and Y is —NR^cAr²—Ar¹, —NR^c(CR^aR^b)_pAr¹, —NR^c-G²-Ar¹, (iii), (iv), or (vi);

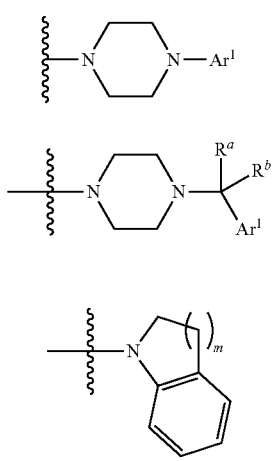

(iii)

(iv)

(vi)

$R^a$ and $R^b$ are, at each occurrence, independently hydrogen or hydroxyalkyl; $R^c$ is hydrogen; p is 1, 2 or 3; $Ar^1$ is aryl; $Ar^2$ is aryl; $G^2$ is cyclopropyl; and $R^3$, $R^4$, $R^5$ and $R^6$ are each independently hydrogen or halogen.

In one embodiment for compounds of formula (I) or formula (II), wherein $R^1$ is X; and X is

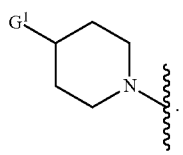

In another embodiment for compounds of formula (I), wherein $R^1$ is X; and X is

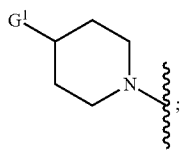

$G^1$ is pyrrolidinyl or piperidinyl; $R^2$ is Y; Y is $NR^cAr^1$; $R^c$ is hydrogen; and $Ar^1$ is aryl, wherein said aryl is unsubstituted or substituted with 1, 2, or 3 substituents selected from haloalkyl and halogen.

In one embodiment for compounds of formula (I) or formula (II), wherein $R^1$ is Y; Y is —NR$^c$CH(Ar$^1$)$_2$, —NR$^c$(CR$^a$R$^b$)$_p$CH(Ar$^1$)$_2$, or (v);

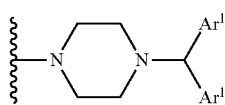

(v)

$R^a$ and $R^b$ at each occurrence are independently hydrogen; $R^2$ is X; X is

and n is 1.

In another embodiment for compounds of formula (I), wherein $R^1$ is Y; Y is —NR$^c$CH(Ar$^1$)$_2$, —NR$^c$(CR$^a$R$^b$)$_p$CH(Ar$^1$)$_2$, or (v);

(v)

$Ar^1$, at each occurrence, is independently aryl, wherein said aryl are unsubstituted or substituted with 1, 2, 3, or 4, or 5 substituents selected from alkoxy, alkyl, cyano, haloalkyl, halogen, or —N(alkyl)$_2$; $R^a$ and $R^b$ at each occurrence are independently hydrogen; p is 1 or 2; $R^2$ is X; X is and n is 1; and $R^3$, $R^4$, $R^5$ and $R^6$ are each independently hydrogen or halogen.

In one embodiment for compounds of formula (I) or formula (II), wherein $R^1$ is Y; Y is —NR$^c$Ar$^1$, —NR$^c$(CR$^a$R$^b$)$_p$Ar$^1$, (iii), (iv), or (vi);

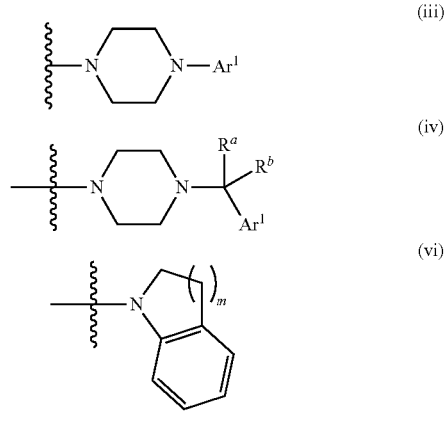

(iii)

(iv)

(vi)

$R^2$ is X; and X is

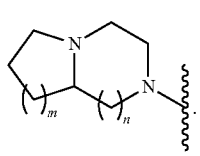

In another embodiment for compounds of formula (I), wherein $R^1$ is Y; Y is —$NR^cAr^1$, —$NR^c(CR^aR^b)_pAr^1$, —$NR^c$-$G^2$, or —$NR^c$-$G^2$-$Ar^1$; $R^a$ and $R^b$ are independently, at each occurrence, hydrogen or hydroxyalkyl; p is 1, 2 or 3; $Ar^1$, at each occurrence, is independently aryl, wherein said aryl are unsubstituted or substituted with 1, 2, 3, or 4, or 5 substituents selected from alkoxy, alkyl, cyano, haloalkyl, halogen, or —N(alkyl)$_2$; $G^2$ is cycloalkyl, wherein cycloalkyl is cyclopropyl, cyclobutyl, cyclopentyl, or cyclohexyl; $R^2$ is X; and X is

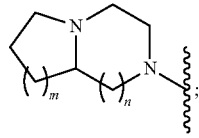

and $R^3$, $R^4$, $R^5$ and $R^6$ are each independently hydrogen or halogen.

In one embodiment for compounds of formula (III) wherein $L^1$ is C(O); $R^2$ is X; X is (i);

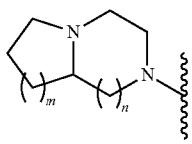

$R^7$ is —$S(O)_2Ar^3$, —$C(O)Ar^3$, —$S(O)_2(CR^aR^b)_pAr^3$, or —$C(O)(CR^aR^b)_pAr^3$; and $Ar^3$, at each occurrence, is aryl, wherein said aryl is unsubstituted or substituted with 1, 2, 3, 4, or 5 substituents selected from alkoxy, alkyl, cyano, haloalkyl, or halogen.

In another embodiment for compounds of formula (IV) wherein $L^1$ is C(O); $R^2$ is X; X is (i);

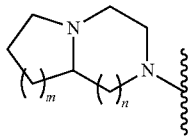

$R^7$ is —$S(O)_2Ar^3$, —$C(O)Ar^3$, —$S(O)_2(CR^aR^b)_pAr^3$, or —$C(O)(CR^aR^b)_pAr^3$; and $Ar^3$ is aryl, wherein said awl is unsubstituted or substituted with 1, 2, 3, 4, or 5 substituents selected from alkoxy, alkyl, cyano, haloalkyl, or halogen.

In another embodiment for compounds of formula (III) wherein $L^1$ is C(O); $R^2$ is X; X is (i);

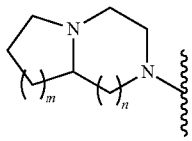

$R^7$ is —$S(O)_2(CR^aR^b)_pCH(Ar^3)_2$, —$C(O)(CR^aR^b)_pCH(Ar^3)_2$, —$C(O)CH(Ar^3)_2$, or —$CH(Ar^3)_2$; $Ar^3$, at each occurrence, is aryl, wherein said aryl is unsubstituted or substituted with 1, 2, 3, 4, or 5 substituents selected from alkoxy, alkyl, cyano, haloalkyl, or halogen; and p is 1, 2, or 3.

In another embodiment for compounds of formula (IV) wherein $L^1$ is C(O); $R^2$ is X; X is (i);

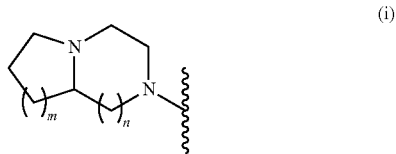

$R^7$ is —$S(O)_2(CR^aR^b)_pCH(Ar^3)_2$, —$C(O)(CR^aR^b)_pCH(Ar^3)_2$, —$C(O)CH(Ar^3)_2$, or —$CH(Ar^3)_2$; $Ar^3$, at each occurrence, is aryl, wherein said aryl is unsubstituted or substituted with 1, 2, 3, 4, or 5 substituents selected from alkoxy, alkyl, cyano, haloalkyl, or halogen; and p is 1, 2, or 3.

Specific embodiments of compounds contemplated as part of the invention include, but are not limited to:
3-[(8aR)-hexahydropyrrolo[1,2-a]pyrazin-2(1H)-ylcarbonyl]-N-[4-(trifluoromethyl)phenyl]benzenesulfonamide;
N-(2-fluorophenyl)-3-[(8aR)-hexahydropyrrolo[1,2-a]pyrazin-2(1H)-ylcarbonyl]benzenesulfonamide;
N-(3-fluorophenyl)-3-[(8aS)-hexahydropyrrolo[1,2-a]pyrazin-2(1H)-ylcarbonyl]benzenesulfonamide;
N-(2,6-difluorophenyl)-3-[(8aS)-hexahydropyrrolo[1,2-a]pyrazin-2(1H)-ylcarbonyl]benzenesulfonamide;
N-(4-fluorophenyl)-3-[(8aS)-hexahydropyrrolo[1,2-a]pyrazin-2(1H)-ylcarbonyl]benzenesulfonamide;
3-[(8aS)-hexahydropyrrolo[1,2-a]pyrazin-2(1H)-yl carbonyl]-N-[3-(trifluoromethyl)phenyl]benzenesulfonamide;
N-(3-fluorophenyl)-3-[(8aR)-hexahydropyrrolo[1,2-a]pyrazin-2 (1H)-ylcarbonyl]benzenesulfonamide;
3-[(8aS)-hexahydropyrrolo[1,2-a]pyrazin-2(1H)-ylcarbonyl]-N-[4-(trifluoromethyl)phenyl]benzenesulfonamide;
N-(2-chlorophenyl)-3-[(8aR)-hexahydropyrrolo[1,2-a]pyrazin-2(1H)-ylcarbonyl]benzenesulfonamide;
N-(2-chlorophenyl)-3-[(8aS)-hexahydropyrrolo[1,2-a]pyrazin-2(1H)-ylcarbonyl]benzenesulfonamide;
N-(2,3-difluorophenyl)-3-[(8aS)-hexahydropyrrolo[1,2-a]pyrazin-2(1H)-ylcarbonyl]benzenesulfonamide;
N-(2,5-difluorophenyl)-3-[(8aS)-hexahydropyrrolo[1,2-a]pyrazin-2(1H)-ylcarbonyl]benzenesulfonamide;
N-(2,6-difluorophenyl)-3-[(8aR)-hexahydropyrrolo[1,2-a]pyrazin-2(1H)-ylcarbonyl]benzenesulfonamide;
N-(2,3-difluorophenyl)-3-[(8aR)-hexahydropyrrolo[1,2-a]pyrazin-2(1H)-ylcarbonyl]benzenesulfonamide;
N-(2,5-difluorophenyl)-3-[(8aR)-hexahydropyrrolo[1,2-a]pyrazin-2(1H)-ylcarbonyl]benzenesulfonamide;
N-(2,4-difluorophenyl)-3-[(8aS)-hexahydropyrrolo[1,2-a]pyrazin-2 (1H)-ylcarbonyl]benzenesulfonamide;
N-(2-fluorophenyl)-3-[(8aS)-hexahydropyrrolo[1,2-a]pyrazin-2 (1H)-ylcarbonyl]benzenesulfonamide;
N-(2,4-difluorophenyl)-3-[(8aR)-hexahydropyrrolo[1,2-a]pyrazin-2(1H)-ylcarbonyl]benzenesulfonamide;
3-[(8aS)-hexahydropyrrolo[1,2-a]pyrazin-2(1H)-ylcarbonyl]-N-[2-(trifluoromethyl)phenyl]benzenesulfonamide;
4-chloro-2-fluoro-N-(2-fluorophenyl)-5-[(8aR)-hexahydropyrrolo[1,2-a]pyrazin-2 (1H)-ylcarbonyl]benzenesulfonamide;
N-(3-chlorophenyl)-3-[(8aS)-hexahydropyrrolo[1,2-a]pyrazin-2(1H)-ylcarbonyl]benzenesulfonamide;
(8aR)-2-[3-({4-[bis(4-fluorophenyl)methyl]piperazin-1-yl}sulfonyl)benzoyl]octahydropyrrolo[1,2-a]pyrazine;

(8aS)-2-[3-({4-[bis(4-fluorophenyl)methyl]piperazin-1-yl}sulfonyl)benzoyl]octahydropyrrolo[1,2-a]pyrazine;

(8aR)-2-{3-[(4-benzhydrylpiperazin-1-yl)sulfonyl]benzoyl}octahydropyrrolo[1,2-a]pyrazine;

N-(3-chlorophenyl)-3-[(8aR)-hexahydropyrrolo[1,2-a]pyrazin-2(1H)-ylcarbonyl]benzenesulfonamide;

N-(2,2-diphenylethyl)-3-[(8aR)-hexahydropyrrolo[1,2-a]pyrazin-2(1H)-ylcarbonyl]benzenesulfonamide;

3-[(8aR)-hexahydropyrrolo[1,2-a]pyrazin-2(1H)-ylcarbonyl]-N-[2-(trifluoromethyl)phenyl]benzenesulfonamide;

(8aS)-2-{3-[(4-benzhydrylpiperazin-1-yl)sulfonyl]benzoyl}octahydropyrrolo[1,2-a]pyrazine;

N-(3,3-diphenylpropyl)-3-[(8aR)-hexahydropyrrolo[1,2-a]pyrazin-2(1H)-ylcarbonyl]benzenesulfonamide;

N-(3,3-diphenylpropyl)-3-[(8aS)-hexahydropyrrolo[1,2-a]pyrazin-2(1H)-ylcarbonyl]benzenesulfonamide;

N-(2,2-diphenylethyl)-3-[(8aS)-hexahydropyrrolo[1,2-a]pyrazin-2(1H)-ylcarbonyl]benzenesulfonamide;

4-chloro-3-[(8aR)-hexahydropyrrolo[1,2-a]pyrazin-2(1H)-ylcarbonyl]-N-[4-(trifluoromethyl)phenyl]benzenesulfonamide;

N-[2-(4-fluorophenyl)ethyl]-3-[(8aS)-hexahydropyrrolo[1,2-a]pyrazin-2(1H)-ylcarbonyl]benzenesulfonamide;

2-chloro-5-[(8aR)-hexahydropyrrolo[1,2-a]pyrazin-2(1H)-ylcarbonyl]-N-[4-(trifluoromethyl)phenyl]benzenesulfonamide;

(8aS)-2-(3-{[4-(4-fluorophenyl)piperazin-1-yl]sulfonyl}benzoyl)octahydropyrrolo[1,2-a]pyrazine;

N-1,1'-biphenyl-2-yl-3-[(8aS)-hexahydropyrrolo[1,2-a]pyrazin-2(1H)-ylcarbonyl]benzenesulfonamide;

3-(octahydro-2H-pyrido[1,2-a]pyrazin-2-ylcarbonyl)-N-[4-(trifluoromethyl)phenyl]benzenesulfonamide;

3-(octahydro-2H-pyrido[1,2-a]pyrazin-2-ylcarbonyl)-N-[3-(trifluoromethyl)phenyl]benzenesulfonamide;

N-(2-fluorophenyl)-3-(octahydro-2H-pyrido[1,2-a]pyrazin-2-ylcarbonyl)benzenesulfonamide;

N-(4-fluorophenyl)-3-[(4-pyrrolidin-1-ylpiperidin-1-yl)carbonyl]benzenesulfonamide;

N-phenyl-3-[(4-pyrrolidin-1-ylpiperidin-1-yl)carbonyl]benzenesulfonamide;

3-[(4-pyrrolidin-1-ylpiperidin-1-yl)carbonyl]-N-[4-(trifluoromethyl)phenyl]benzenesulfonamide;

3-[(4-pyrrolidin-1-ylpiperidin-1-yl)carbonyl]-N-[3-(trifluoromethyl)phenyl]benzenesulfonamide;

N-(3-fluorophenyl)-3-[(4-pyrrolidin-1-ylpiperidin-1-yl)carbonyl]benzenesulfonamide;

N-(2-fluorophenyl)-3-[(4-pyrrolidin-1-ylpiperidin-1-yl)carbonyl]benzenesulfonamide;

3-(1,4'-bipiperidin-1'-ylcarbonyl)-N-(4-fluorophenyl)benzenesulfonamide;

3-(1,4'-bipiperidin-1'-ylcarbonyl)-N-(2-fluorophenyl)benzenesulfonamide;

3-(1,4'-bipiperidin-1'-ylcarbonyl)-N-(3-fluorophenyl)benzenesulfonamide;

3-(1,4'-bipiperidin-1'-ylcarbonyl)-N-[4-(trifluoromethyl)phenyl]benzenesulfonamide;

(8aR)-2-{[3-({4-[bis(4-fluorophenyl)methyl]piperazin-1-yl}carbonyl)phenyl]sulfonyl}octahydropyrrolo[1,2-a]pyrazine;

(8aS)-2-{[3-({4-[bis(4-fluorophenyl)methyl]piperazin-1-yl}carbonyl)phenyl]sulfonyl}octahydropyrrolo[1,2-a]pyrazine;

(8aR)-2-({3-[(4-benzhydrylpiperazin-1-yl)carbonyl]phenyl}sulfonyl)octahydropyrrolo[1,2-a]pyrazine;

N-(2,2-diphenyl ethyl)-3-[(8aS)-hexahydropyrrolo[1,2-a]pyrazin-2(1H)-ylsulfonyl]benzamide;

(8aS)-2-({3-[(4-benzhydrylpiperazin-1-yl)carbonyl]phenyl}sulfonyl)octahydropyrrolo[1,2-a]pyrazine;

N-(3,3-diphenylpropyl)-3-[(8aS)-hexahydropyrrolo[1,2-a]pyrazin-2(1H)-ylsulfonyl]benzamide;

N-[2-(4-fluorophenyl)ethyl]-3-[(8aS)-hexahydropyrrolo[1,2-a]pyrazin-2(1H)-ylsulfonyl]benzamide;

3-[(8aR)-hexahydropyrrolo[1,2-a]pyrazin-2(1H)-ylcarbonyl]-N-[(1S)-2-hydroxy-1-phenylethyl]benzenesulfonamide;

4-chloro-2-fluoro-N-(2-fluorophenyl)-5-[(8aS)-hexahydropyrrolo[1,2-a]pyrazin-2(1H)-ylcarbonyl]benzenesulfonamide;

4-chloro-N-(3,3-diphenylpropyl)-2-fluoro-5-[(8aS)-hexahydropyrrolo[1,2-a]pyrazin-2(1H)-ylcarbonyl]benzenesulfonamide;

3-[(8aS)-hexahydropyrrolo[1,2-a]pyrazin-2(1R)-ylsulfonyl]-N-[(1R,2S)-2-phenylcyclopropyl]benzamide;

3-[(8aS)-hexahydropyrrolo[1,2-a]pyrazin-2(1H)-ylcarbonyl]-N-[(1R,2S)-2-phenylcyclopropyl]benzenesulfonamide;

4-[(8aR)-hexahydropyrrolo[1,2-a]pyrazin-2(1H)-ylcarbonyl]-N-[(1S)-2-hydroxy-1-phenylethyl]benzenesulfonamide;

(8aR)-2-[2-chloro-5-(2,3-dihydro-1H-indol-1-ylsulfonyl)-4-fluorobenzoyl]octahydropyrrolo[1,2-a]pyrazine;

2,4-dichloro-N-(2-fluorophenyl)-5-[(8aR)-hexahydropyrrolo[1,2-a]pyrazin-2(1H)-ylcarbonyl]benzenesulfonamide;

N-{2-fluoro-5-[(8aR)-hexahydropyrrolo[1,2-a]pyrazin-2(1H)-ylcarbonyl]phenyl}-3-(trifluoromethyl)benzenesulfonamide;

4-chloro-2-fluoro-N-(2-fluorophenyl)-5-[(8aR)-hexahydropyrrolo[1,2-a]pyrazin-2(1H)-ylcarbonyl]-N-methylbenzenesulfonamide;

(8aR)-2-(2-chloro-4-fluoro-5-{[4-(4-fluorophenyl)piperazin-1-yl]sulfonyl}benzoyl)octahydropyrrolo[1,2-a]pyrazine;

N-{2-chloro-5-[(8aR)-hexahydropyrrolo[1,2-a]pyrazin-2(1H)-ylcarbonyl]phenyl}-4-fluorobenzamide;

N-{3-[(8aR)-hexahydropyrrolo[1,2-a]pyrazin-2(1H)-ylcarbonyl]phenyl}-N-methyl-3-(trifluoromethyl)benzenesulfonamide;

4-chloro-N-(2,2-diphenylethyl)-2-fluoro-5-[(8aR)-hexahydropyrrolo[1,2-a]pyrazin-2(1H)-ylcarbonyl]benzenesulfonamide;

N-{2-chloro-4-[(8aR)-hexahydropyrrolo[1,2-a]pyrazin-2(1H)-ylcarbonyl]phenyl}-4-fluorobenzamide;

N-{4-[(8aR)-hexahydropyrrolo[1,2-a]pyrazin-2(1H)-ylcarbonyl]-2-methylphenyl}-2-naphthamide;

3,5-dichloro-N-{2-fluoro-5-[(8aR)-hexahydropyrrolo[1,2-a]pyrazin-2(1H)-ylcarbonyl]phenyl}benzamide;

N-benzhydryl-4-chloro-2-fluoro-5-[(8aR)-hexahydropyrrolo[1,2-a]pyrazin-2(1H)-ylcarbonyl]benzenesulfonamide;

N-{2-chloro-4-[(8aR)-hexahydropyrrolo[1,2-a]pyrazin-2(1H)-ylcarbonyl]phenyl}-2,2-diphenylacetamide;

N-{2-chloro-4-[(8aR)-hexahydropyrrolo[1,2-a]pyrazin-2(1H)-ylcarbonyl]phenyl}-2-naphthamide;

N-{3-[(8aR)-hexahydropyrrolo[1,2-a]pyrazin-2(1H)-ylcarbonyl]phenyl}-N-isopropyl-3-(trifluoromethyl)benzenesulfonamide;

N-{2-chloro-5-[(8aR)-hexahydropyrrolo[1,2-a]pyrazin-2(1H)-ylcarbonyl]phenyl}-2,2-diphenylacetamide;

N-benzhydryl-N-{2-chloro-5-[(8aR)-hexahydropyrrolo[1,2-a]pyrazin-2(1H)-ylcarbonyl]phenyl}amine;

N-benzhydryl-N-{3-[(8aR)-hexahydropyrrolo[1,2-a]pyrazin-2(1H)-ylcarbonyl]phenyl}amine;

3-[(8aR)-hexahydropyrrolo[1,2-a]pyrazin-2(1H)-ylsulfonyl]-N-[(1S)-2-hydroxy-1-phenylethyl]benzamide;
N-benzhydryl-2-chloro-4-fluoro-5-[(8aS)-hexahydropyrrolo[1,2-a]pyrazin-2(1H)-ylsulfonyl]benzamide; or
2-chloro-N-cyclopropyl-4-fluoro-5-[(8aS)-hexahydropyrrolo[1,2-a]pyrazin-2(1H)-ylsulfonyl]benzamide.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in formula (I), formula (II), formula (III) or formula (IV), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I), formula (II), formula (III) or formula (IV) are $^{11}$C, $^{13}$N, $^{15}$O, and $^{18}$F. Isotopically-labeled compounds of formula (I), formula (II), formula (III) or formula (IV) can generally be prepared by conventional techniques known to those skilled in the art or by processes analogous to those described in the accompanying Schemes and Examples using appropriate isotopically-labeled reagent in place of non-isotopically-labeled reagent.

c. Biological Data

Abbreviations which have been used in the descriptions of Biological Data that follow are: EGTA for ethylene glycol tetraacetic acid; FLIPR for fluorometric imaging plate reader; HEPES for 4-(2-hydroxyethyl)-1-piperazineethanesulfonic acid; i.p. for intraperitoneal; Mg$_2$ATP for dimagnesium adenosine triphosphate complex; p.o. for per orem (by mouth); and TEA-Cl for tetraethylammonium chloride.

(i) In Vitro Methods—Electrophysiologic Assessment of Calcium Channel Activity:

Patch-clamp recordings were performed using HEK293 cells stably expressing hCa$_v$3.2. Cells were plated in T175 flasks and grown at 37° C. and under 5% CO$_2$ to approximately 50% confluency. On the day of the experiment, cells were harvested with Detachin™ cell detachment solution (Genlantis, San Diego, Calif.) and maintained in serum-free culture medium supplemented with 25 mM HEPES up to several hours prior to experiment. Whole-cell patch-clamp recordings were obtained using extracellular saline consisting of (mM): 87.5 CsCl, 40 TEA-Cl, 5 CaCl$_2$, 1 MgCl$_2$, 10 HEPES, 10 glucose. The pH was adjusted to 7.2 with CsOH and the osmolarity was adjusted to approximately 310 mOsm with sucrose. Intracellular solution consisted of (mM): 112 CsCl, 27 CsF, 2 NaCl, 8.2 EGTA, 10 HEPES. Prior to an experiment 4 mM Mg$_2$ATP was added and the pH was adjusted to 7.2 with CsOH with an osmolarity of approximately 290 mOsm. A two-pulse voltage protocol was utilized to assess compound inhibition. First, cells were held with an 8 s pre-pulse at −100 mV prior to a 160 ms test pulse to −30 mV. This was followed by an 8 s pre-pulse at approximately −75 mV prior to a −160 mV test pulse to 30 mV. Increasing concentrations of antagonist were applied to individual cells in a multi-addition format with 5 minutes in each test concentration. For each cell, responses were normalized to dimethyl sulfoxide vehicle control to generate concentration-response curves.

Table 1 lists IC$_{50}$ values for compounds of the present invention.

TABLE 1

Electrophysiologic Assessment for Human Cav3.2 Channels

| Example | Qualifier | Human Ca$_v$3.2<br>−77 mV<br>IC$_{50}$ (µM)<br>GeoMean |
|---------|-----------|-------------------------------------------------------|
| 1       | >         | 10                                                    |
| 2       |           | 10.6                                                  |
| 3       |           | 5.9                                                   |
| 4       |           | 7.7                                                   |
| 5       |           | 1.8                                                   |
| 6       |           | 1.9                                                   |
| 7       |           | 6.5                                                   |
| 8       |           | 2.1                                                   |
| 9       |           | 7.3                                                   |
| 10      |           | 1.5                                                   |
| 11      |           | 6.6                                                   |
| 12      |           | 4.7                                                   |

TABLE 1-continued

Electrophysiologic Assessment for Human Cav3.2 Channels

| Example | Qualifier | Human Ca$_v$3.2<br>−77 mV<br>IC$_{50}$ (μM)<br>GeoMean |
|---|---|---|
| 13 |  | 5.6 |
| 14 |  | 3.7 |
| 15 | > | 10 |
| 16 |  | 6.0 |
| 17 | > | 10 |
| 18 |  | 9.3 |
| 19 |  | 2.4 |
| 20 |  | 6 |
| 21 |  | 5.9 |
| 22 |  | 1.4 |
| 23 |  | 2.5 |
| 24 |  | 1.0 |
| 25 |  | 8.9 |
| 26 |  | 1.5 |
| 27 | > | 10 |
| 28 |  | 1.9 |
| 29 |  | 2.1 |
| 30 |  | 1.8 |
| 31 |  | 3.3 |
| 32 |  | 8.4 |
| 33 |  | 5.7 |
| 34 |  | 6.2 |
| 35 |  | 4.8 |
| 36 |  | 4.7 |
| 37 |  | 1.1 |
| 38 |  | 4.6 |
| 39 |  | 4.1 |
| 40 |  | 4.1 |
| 41 |  | 5.0 |
| 42 |  | 5.8 |
| 43 |  | 4.9 |
| 44 |  | 4.9 |
| 45 | > | 10 |
| 46 |  | 1.8 |
| 47 |  | 3.8 |
| 48 | > | 10 |
| 49 |  | 1.3 |
| 50 |  | 0.6 |
| 51 |  | 0.9 |
| 52 |  | 0.6 |
| 53 |  | 0.5 |
| 54 |  | 1.2 |
| 55 |  | 1.8 |
| 56 |  | 4.1 |
| 57 |  | 48 |
| 58 |  | 4.6 |
| 59 |  | 9.0 |
| 60 |  | 5.0 |
| 61 | > | 10 |
| 62 | > | 10 |
| 63 | > | 10 |
| 64 |  | 1.7 |
| 65 |  | 1.84 |
| 66 |  | 5.9 |
| 67 |  | 3.18 |
| 68 |  | 10.9 |
| 69 | > | 10 |
| 70 |  | 7.2 |
| 71 |  | 10 |
| 72 | > | 10 |
| 73 |  | 1.8 |
| 74 |  | 2 |
| 75 |  | 6.5 |
| 76 |  | 6.4 |
| 77 | > | 10 |
| 78 | > | 10 |
| 79 |  | 8.5 |
| 80 |  | 2 |
| 81 | > | 10 |
| 82 |  | 2.6 |
| 83 | > | 10 |

(ii) In Vivo Data—Capsaicin Induced Secondary Mechanical Hyperalgesia Model:

Sprague Dawley rats were briefly restrained, and capsaicin was administered at 10 μg in 10 μL of vehicle by intraplantar injection into the center of the right hind paw. Secondary mechanical hyperalgesia (SMH) was measured at the heel away from the site of injection 180 minutes following capsaicin exposure. Compounds and gabapentin (positive control), were administered p.o. 60 minutes before testing (2 hours after capsaicin) or i.p. 30 minutes before testing (2.5 hours after capsaicin). SMH was measured using calibrated von Frey filaments (Stoelting, Woodale, Ill.). Following the 1 hour habituation in the testing room, rats were moved to individual plexiglass chambers that sit on top of a wire mesh to allow for access for stimulation of the plantar surface of the hind paws. Rats were allowed to acclimate to the new chambers for 15 minutes before the onset of testing. The paw withdrawal threshold was determined by increasing and decreasing stimulus intensity (force: g) and calculated using Dixon's up-down method (Chaplan, S. R.; Bach, F. W.; Pogrel, J. W.; Chung, J. M.; Yaksh, T. L.; Quantitative assessment of tactile allodynia in the rat paw. J. Neuroscience Methods 1994, 53(1), 55-63). The filaments (maximum force of 15.0 g) were held in place for 8 seconds or until there was a withdrawal response from the mechanical stimulation.

Table 2 lists results for representative examples of the present invention.

TABLE 2

Inhibition to Pain Response

| Example | % inhibition @<br>30 mg/kg p.o. |
|---|---|
| 2 | 58 |
| 3 | 44 |
| 13 | 37 |
| 20 | 43 |
| 37 | 63 |
| 64 | 57 | d. Methods of using the Compounds

One embodiment of the present invention provides a method of treating pain in a subject in need thereof. The method comprises administering to the subject, including a mammal, such as a human, a therapeutically suitable amount of a compound of formula (I), formula (II), formula (III), or formula (IV), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazapine, histamine antagonist, sedative, skeletal muscle relaxant, transient receptor potential ion channel antagonist, α-adrenergic, tricyclic antidepressant, anti convulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, $5-HT_{2A}$ receptor antagonist, cholinergic analgesic, $\alpha_2\delta$ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin $E_2$ subtype 4 antagonist, leukotriene B4 antagonist, 5-lipoxygenase inhibitor, sodium channel blocker, 5-HT3 antagonist, N-methyl-D-aspartic acid receptor antagonist, or phosphodiesterase V inhibitor.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F.; et al. Calcium channel blockade to prevent stroke in hypertension. American Journal of Hypertension 2004, 17(9), 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F. C.; et al. SB 201823-A antagonizes calcium currents in central neurons and reduces the effects of focal ischemia in rats and mice. Stroke 1995, 26, 1683-1690). In another model of global ischemia, a calcium channel blocker offered neuroprotection although not permanently (Colbourne, F.; et al. Continuing postischemic neuronal death in CA1: Influence of ischemia duration and cytoprotective doses of NBQX and SNX-111 in rats. Stroke 1999, 30(3), 662-668). Additionally, diminished progression of carotid atherosclerosis has been observed with calcium channel blocker use (Zanchetti, A.; et al. Calcium antagonist lacidipine slows down progression of asymptomatic carotid atherosclerosis. Principal results of the European lacidipine study on atherosclerosis (ELSA), a randomized, double-blind, long-term trial. Circulation 2002, 106, r47-r52).

An increase in intracellular calcium concentration has been correlated with seizure activity (Heinemann, U.; et al. Extracellular free calcium and potassium during paroxysmal activity in the cerebral cortex of the cat. Exp. Brain Res. 1977, 27, 237-243). Several studies have indicated that calcium channel blockers produce anti convulsant activity (Vezzani, A.; et al. Effects of various calcium channel blockers on three different models of limbic seizures in rats. Neuropharmacology 1988, 27(5), 451-458. Otoom, S.; et al. Nifedipine inhibits picrotoxin-induced seizure activity: further evidence on the involvement of L-type calcium channel blockers in epilepsy. Fundamental & Clinical Pharmacology 2006, 20, 115-119).

Calcium channel blockers have been evaluated in the treatment of bipolar disorders and manic depression for decades. There are suggestions that the calcium channel subtype has influence on efficacy of these disorders (Gitlin, M. Treatment-resistant bipolar disorder. Molecular Psychiatry 2006, 11, 227-240. Levy, N. A.; Janicak, P. G. Bipolar Disorders 2000, 2, 108-119).

Calcium channel blockers have also been associated with the treatment of anxiety and depression (Saade, S.; et al. The L-type calcium channel blocker nimodipine mitigates "learned helplessness" in rats. Pharmacology, Biochemistry and Behavior 2003, 74, 269-278).

Antischizophrenic drugs have been found to be calcium channel antagonists (Gould, R. J.; et al. Antischizophrenic drugs of the diphenylbutylpiperidine type act as calcium channel antagonists. Proc. Natl. Acad. Sci. USA 1983, 80, 5122-5125). Other calcium channel blockers have been suggested for the treatment of schizophrenia (Tort, A. B. L.; et al. Atypical antipsychotic profile of flunarizine in animal models. Psychopharmacology 2005, 177, 344-348).

Migraines are treated with calcium channel blockers (Arulmoshi, D. K.; et al. Migraine: Current concepts and emerging therapies. Vascular Pharmacology 2005, 43, 176-187. Gladstone, J. P.; et al. Current and emerging treatment options for migraine and other primary headache disorders. Expert Rev. Neurotherapeutics 2003, 3(6), 845-872).

Disorders of the lower urinary tract including overactive bladder, prostatis, prostadynia, interstitial cystitis, and benign prostatic hyperplasia can be treated with calcium channel blockers (Fraser, M. O.; et al. US20050148587, 2005).

Ethanol withdrawal syndrome is decreased with calcium channel blockers (Little, H. J.; et al. Calcium channel antagonists decrease the ethanol withdrawal syndrome. Life Sciences 1986, 39, 2059-2065).

Several cardiac disorders are treated with calcium channel blockers. Atherosclerosis may be reduced by a decrease in free radical-mediated damage as a result of influence on the biophysical properties of membranes (Mason, R. P.; et al. Antioxidant and cytoprotective activities of the calcium channel blocker mibefradil. Biochemical Pharmacology 1998, 55, 1843-1852). Hypertension and angina are both successfully treated with calcium channel blockers (Croom, K. F.; et al. Modified-release nifedipine: A review of the use of modified-release formulations in the treatment of hypertension and angina pectoris. Drugs 2006, 66(4), 497-528).

There is data suggesting that calcium channel blockers inhibit the proliferation of cancer cells (Gray, L. S.; et al. International Publication No. WO200059882, 2000).

Calcium channels have been suggested as a target for the treatment of diabetes (Bhattacharjee, A.; et al. T-Type calcium channels facilitate insulin secretion by enhancing general excitability in the insulin-secreting β-cell line, INS-1. Endocrinology 1997, 138(9), 3735-3740).

Ion channels including calcium channels play an important role in sperm physiology and fertilization (Darszon, A.; et al. Ion channels in sperm physiology. Physiological Reviews 1999, 79(2), 481-510).

Calcium channel blockers modulate inflammation (Bilici, D.; et al. Protective effect of T-type calcium channel blocker in histamine-induced paw inflammation in rat. Pharmacological Research 2001, 44(6), 527-531).

Increased calcium levels in neurones has been implicated in Alzheimer's disease. Two suggested mechanisms of increased calcium influx are that β-amyloid may form calcium permeable channels (Bhatia, R.; et al. Fresh and globular amyloid beta protein (1-42) induces rapid cellular degeneration: evidence for AβP channel-mediated cellular toxicity. FASEB J. 2000, 14(9), 1233-1243) or a G-protein-coupled receptor may be activated by β-amyloid (Lorton, D. β-Amyloid induced IL-1 β release from an activated human monocyte cell line is calcium- and G-protein-dependent. Mech. Ageing Dev. 1997, 94(1-3), 199-211).

Neurodegenerative diseases, including Parkinson's and Alzheimer's diseases can be modulated by calcium channel blockers (Rodnitzky, R. L. Can calcium antagonists provide a neuroprotective effect in Parkinson's disease. Drugs 1999, 57(6), 845-849. Vagnucci, A. H., Jr.; et al. Alzheimer's disease and angiogenesis. The Lancet 2003, 361(9357), 605-608. Veng, L. M.; et al. Age-related working memory impairment is correlated with increases in the L-type calcium channel protein $\alpha_{1D}$ ($Ca_v1.3$) in area CA1 of the hippocampus and both are ameliorated by chronic nimodipine treatment. Molecular Brain Research 2203, 110, 193-202. Geldenhuys, W. J.; et al. Structure-activity relationships of pentacycloundecylamines at the N-methyl-D-aspartate receptor. Bioorganic and Medicinal Chemistry 2007, 15, 1525-1532. Cavalli, A.; et al. Multi-target-directed ligands to combat neurodegenerative diseases. J. Med. Chem. 2008, 51(3), 347-372.)

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level depends upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It is understood, however, that the total daily usage of the compounds and compositions of the invention will be decided by the attending physician within the scope of sound medical judgment. The specific therapeutically effective dose level for any particular patient depends upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, $5-HT_{2A}$ receptor antagonists, cholinergic analgesics, $\alpha_2\delta$ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $L^1$, $R^1$, $R^2$, $R^3$, $R^4$, $R^5$, $R^6$, $R^7$, $R^c$, X, and Y have the meanings as set forth in the Summary of the Invention section unless otherwise noted, can be synthesized as shown in Schemes 1-9.

Abbreviations which have been used in the descriptions of the Schemes and the Examples that follow are: DMSO for dimethyl sulfoxide; ESI for electrospray ionization; and Et for ethyl.

Scheme 1

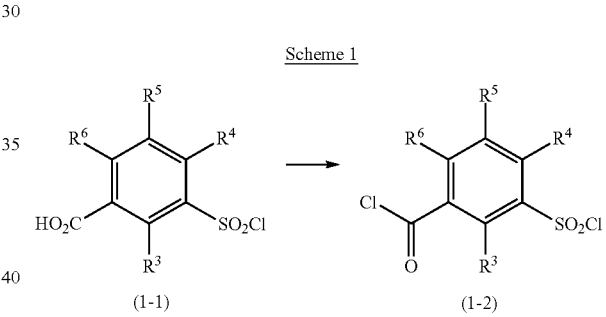

Compounds of formula (1-2) wherein $R^3$, $R^4$, $R^5$ and $R^6$ are as defined for formula (I) can be prepared as described in Scheme 1. Compounds of formula (1-1) can be treated with excess oxalyl chloride optionally in the presence of N,N-dimethylformamide in a solvent such as dichloromethane or toluene at a temperature from room temperature to the reflux temperature of the reaction solvent. Alternatively, a carboxylic acid of formula (1-1) can be reacted with thionyl chloride optionally in the presence of N,N-dimethylformamide at a temperature from room temperature to refluxing to furnish compounds of formula (1-2).

Scheme 2

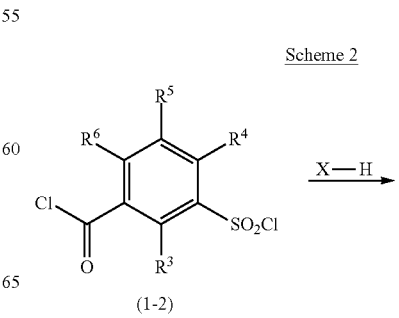

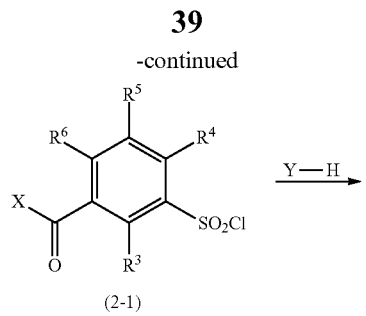

(2-1)

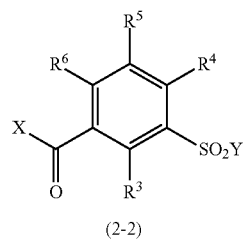

(2-2)

Compounds of formula (2-2) wherein $R^3$, $R^4$, $R^5$ and $R^6$ are as defined for formula (I) can be prepared as described in Scheme 2. Accordingly, compounds of formula (1-2) which are obtained commercially or obtained from the procedures described in Scheme 1 can be reacted with X—H, wherein the H is a hydrogen on a nitrogen atom contained within a heterocycle and X is said heterocycle as described in the Summary of the Invention, in the presence of a base such as sodium carbonate in a solvent such as dichloromethane at room temperature from 2-24 hours to provide compounds of formula (2-1). Compounds of formula (2-1) can be carried on without isolation or purification by treatment with excess Y—H, wherein the H is a hydrogen on a nitrogen atom contained within a heterocycle or primary amine, and wherein Y is as described in the Summary of the Invention, over 1 to 4 days at ambient temperature in a solvent such as dichloromethane or with heating in a neat mixture of the amine to give compounds of formula (2-2) which are representative of compounds of formula (I).

Scheme 3

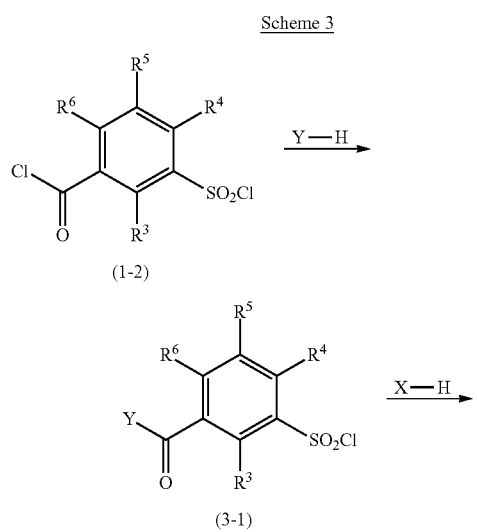

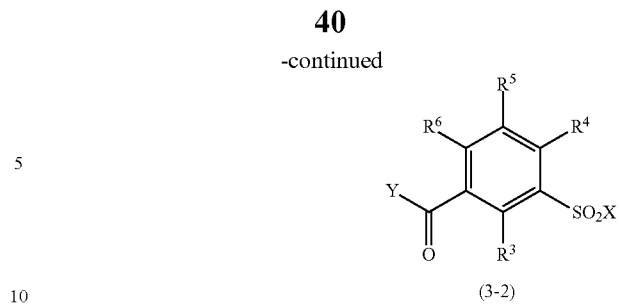

(3-2)

Compounds of formula (3-2) wherein $R^3$, $R^4$, $R^5$ and $R^6$ are as defined for formula (I) can be prepared as described in Scheme 3. Compounds of formula (1-2) which are obtained commercially or obtained from the procedures described in Scheme 1 can be reacted with excess Y—H, wherein the H is a hydrogen on a nitrogen atom contained within a heterocycle or primary amine, and wherein Y is as described in the Summary of the Invention, in the presence of a base such as sodium carbonate in a solvent such as dichloromethane at room temperature from 2-24 hours to provide compounds of formula (3-1). Compounds of formula (3-1) can be carried on without isolation or purification by treatment with X—H, wherein the H is a hydrogen on a nitrogen atom contained within a heterocycle, and wherein X is as described in the Summary of the Invention, optionally initially at reflux and then over 1 to 4 days at ambient temperature to give compounds of formula (3-2) which are representative of compounds of formula (I).

Scheme 4

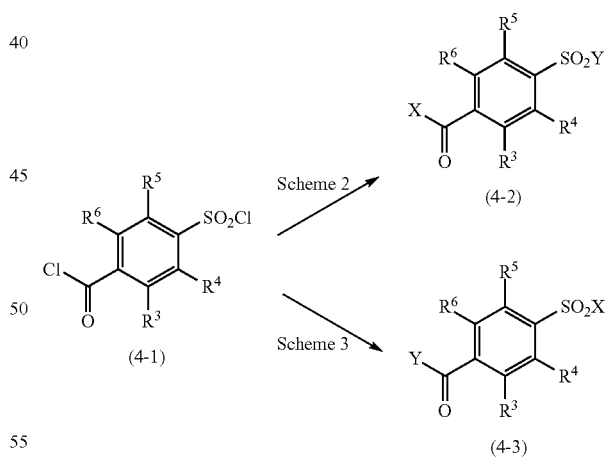

Compounds of formula (4-2) and formula (4-3) wherein $R^3$, $R^4$, $R^5$ and $R^6$ are as defined for formula (II) can be prepared as described in Scheme 4. Compounds of formula (4-1) which are obtained commercially or obtained from the corresponding benzoic acid according to the procedures described in Scheme 1 can be reacted in the sequences described in Scheme 2 and Scheme 3 to give compounds of formula (4-2) and formula (4-3), respectively. Compounds of formula (4-2) and formula (4-3) are representative of compounds of formula (II).

Scheme 5

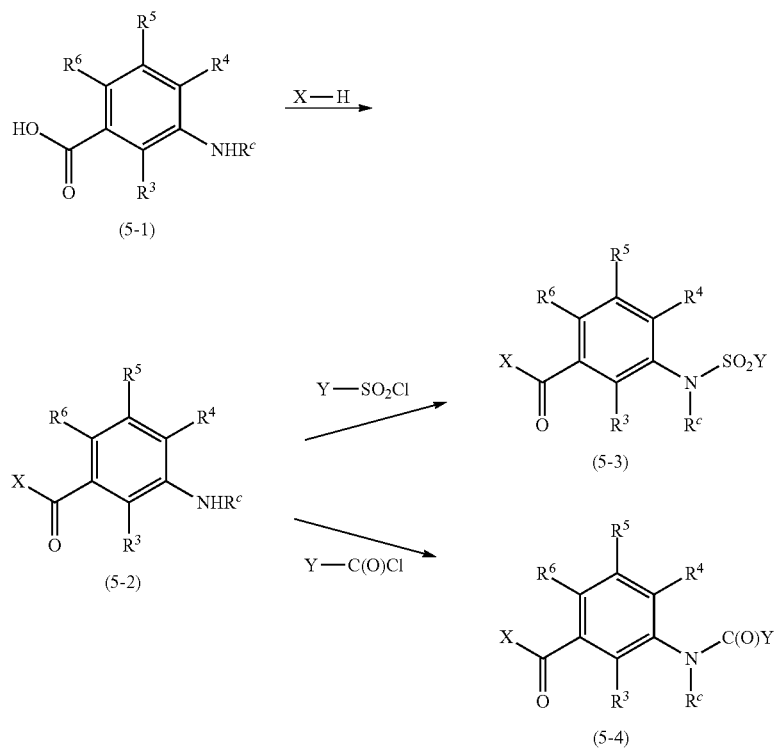

Compounds of formula (5-3) and (5-4) which are representative of compounds of formula (III), wherein $R^3$, $R^4$, $R^5$, $R^6$, $R^c$, X and Y are as described in the Summary of the Invention, can be prepared as described in Scheme 5. Reacting compounds of formula (5-1) with X—H, wherein the H is a hydrogen on a nitrogen atom contained within a heterocycle and X is said heterocycle as described in the Summary of the Invention, under amide bond coupling conditions gives compounds of formula (5-2). Examples of conditions known to generate amides from a mixture of a carboxylic acid and an amine include but are not limited to adding a coupling reagent such as but not limited to N-(3-dimethylaminopropyl)-N-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2-(3H[1,2,3]triazolo[4,5-b]pyridin-3-yl)-1,1,3,3-tetramethylisouronium hexafluorophosphate(V). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate or mixtures thereof. The reaction may be conducted at ambient or elevated temperatures. Compounds of formula (5-2) can then be reacted with sulfonyl chlorides of formula Y—SO₂Cl in the presence of a base such as sodium carbonate or triethylamine in a solvent such as N,N-dimethylformamide either at ambient or elevated temperature to supply compounds of formula (5-3). In similar fashion, compounds of formula (5-2) can be reacted with an acid chloride of formula Y—C(O)Cl to give compounds of formula (5-4).

Scheme 6

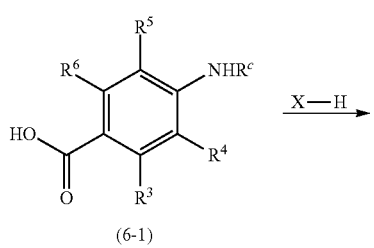

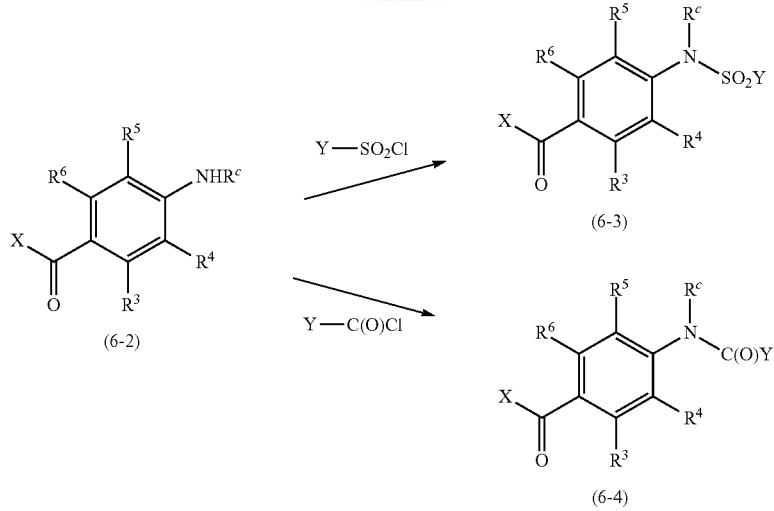

Compounds of formula (6-3) and (6-4) which are representative of compounds of formula (IV), wherein $R^3$, $R^4$, $R^5$, $R^6$, $R^c$, X and Y are as described in the Summary of the Invention, can be prepared as described in Scheme 6. The methodology described in Scheme 5 can be used to convert compounds of formula (6-1) into compounds of formula (6-2). Subsequently, compounds of formula (6-2) can be transformed to either compounds of formula (6-3) or (6-4) also using the procedures described in Scheme 5.

Scheme 7

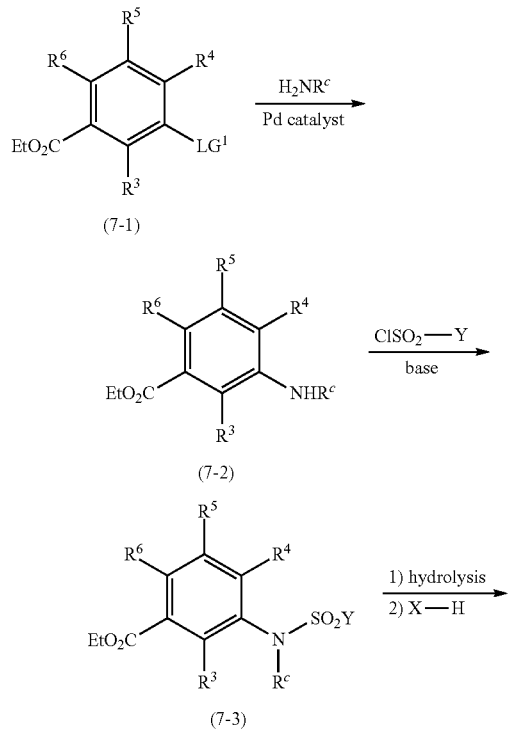

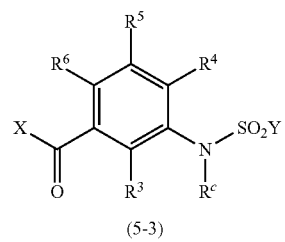

Compounds of formula (5-3) which are representative of compounds of formula (III), wherein $R^3$, $R^4$, $R^5$, $R^6$, $R^c$, X and Y are as described in the Summary of the Invention, can be prepared as described in Scheme 7. Compounds of formula (7-1), wherein $LG^1$ is a leaving group such as bromine, iodine, or trifluoromethansulfonate, may be reacted in cross-coupling reactions with amines of formula $H_2NR^c$ to supply compounds of formula (7-2). The coupling reactions are typically conducted in the presence of a metal catalyst such as palladium or copper with appropriate ligands, bases, temperature, and solvents suggested in the following references: For reviews of Pd catalyzed reaction, see: (a) Schlummer, B.; Scholz, U. *Adv. Synth. Catal.* 2004, 346, 1599. (b) Jiang, L.; Buchwald, S. L. in *Metal Catalyzed Cross-Coupling Reactions,* 2nd ed.; de Meijere, A.; Diederich, F.; Eds.; John Wiley & Sons: Weinheim, 2004. For reviews of Cu catalyzed reactions, see (c) Ley, S. V.; Thomas, A. W. *Angew. Chem. Int. Ed.* 2003, 42, 5400. Compounds of formula (7-2) can then be reacted with sulfonyl chlorides of formula $ClSO_2$—Y in heated pyridine to give sulfonamides of formula (7-3). The ester moiety of compounds of formula (7-3) can then be hydrolyzed by conditions well known in the art, and then the exposed carboxylic acid can then be coupled with a compound of formula X—H, wherein the H is a hydrogen on a nitrogen atom contained within a heterocycle and X is said heterocycle as described in the Summary of the Invention, under the amide bond coupling conditions described in Scheme 5 to give compounds of formula (5-3).

Scheme 8

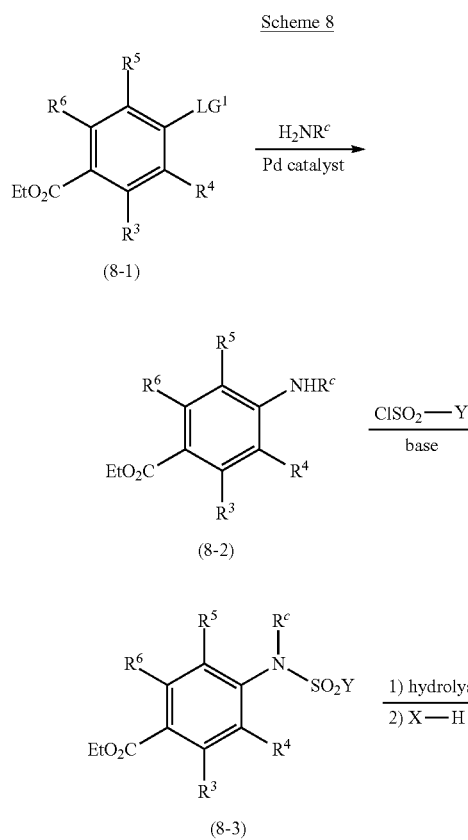

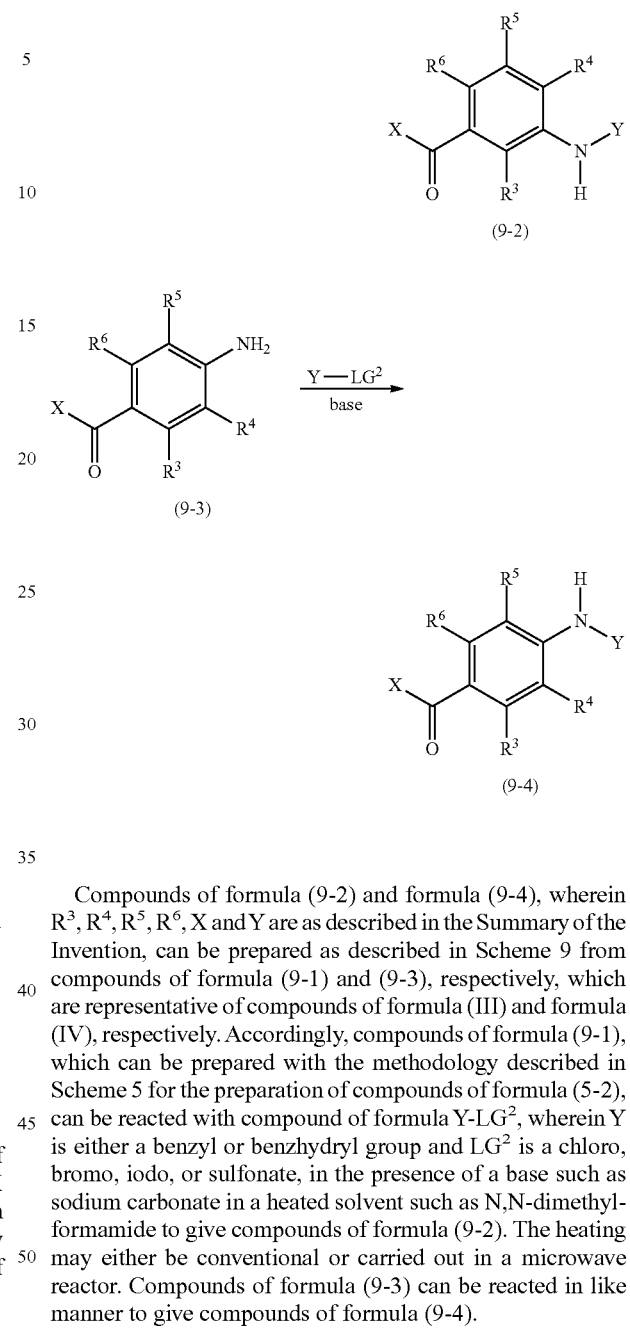

Compounds of formula (6-3), which are representative of compounds of formula (IV), wherein $R^3$, $R^4$, $R^5$, $R^6$, $R^c$, X and Y are as described in the Summary of the Invention, can be prepared as described in Scheme 8. The methodology described in Scheme 7 can be used to convert compounds of formula (8-1) into compounds of formula (6-3).

Compounds of formula (9-2) and formula (9-4), wherein $R^3$, $R^4$, $R^5$, $R^6$, X and Y are as described in the Summary of the Invention, can be prepared as described in Scheme 9 from compounds of formula (9-1) and (9-3), respectively, which are representative of compounds of formula (III) and formula (IV), respectively. Accordingly, compounds of formula (9-1), which can be prepared with the methodology described in Scheme 5 for the preparation of compounds of formula (5-2), can be reacted with compound of formula Y-LG², wherein Y is either a benzyl or benzhydryl group and LG² is a chloro, bromo, iodo, or sulfonate, in the presence of a base such as sodium carbonate in a heated solvent such as N,N-dimethylformamide to give compounds of formula (9-2). The heating may either be conventional or carried out in a microwave reactor. Compounds of formula (9-3) can be reacted in like manner to give compounds of formula (9-4).

Scheme 9

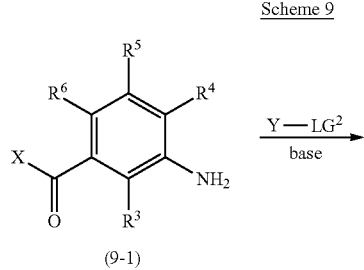

Scheme 10

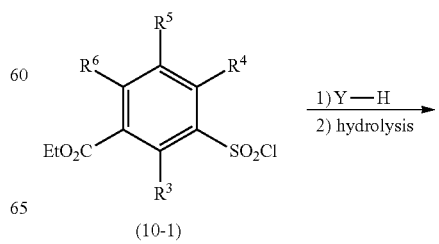

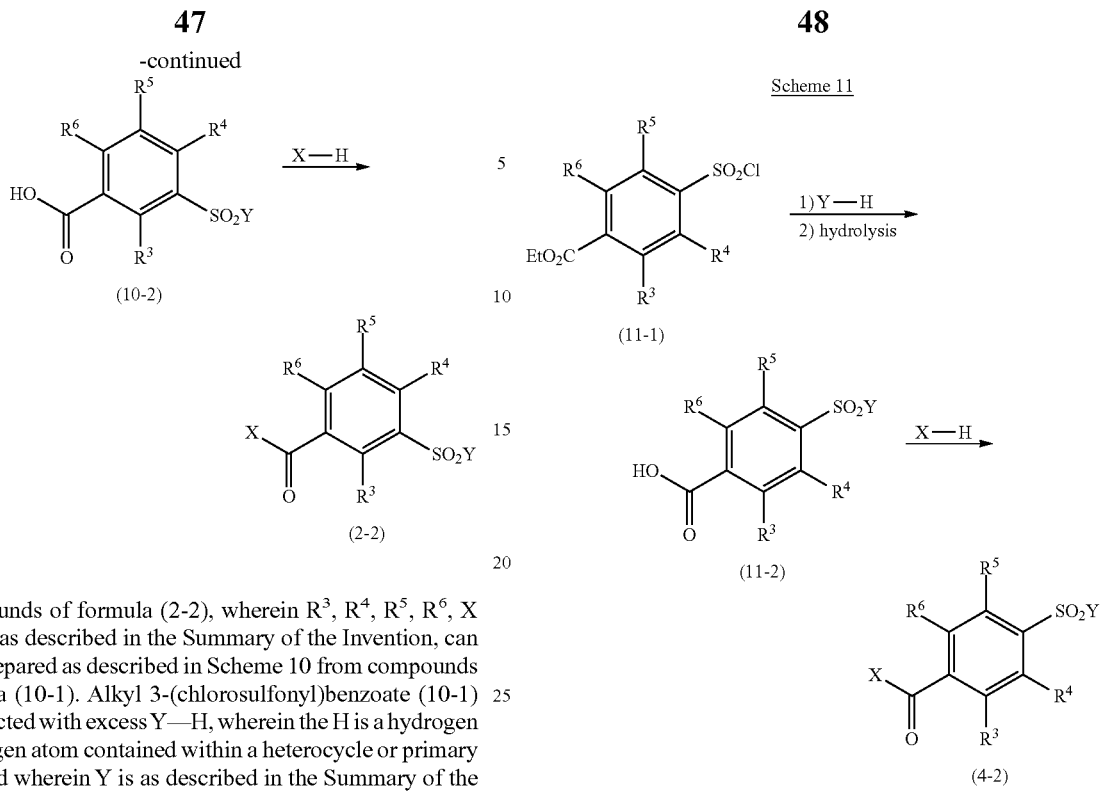

Compounds of formula (2-2), wherein $R^3$, $R^4$, $R^5$, $R^6$, X and Y are as described in the Summary of the Invention, can also be prepared as described in Scheme 10 from compounds of formula (10-1). Alkyl 3-(chlorosulfonyl)benzoate (10-1) can be reacted with excess Y—H, wherein the H is a hydrogen on a nitrogen atom contained within a heterocycle or primary amine, and wherein Y is as described in the Summary of the Invention, over 1 to 8 hours at ambient temperature in a solvent such as N,N-dimethylacetamide. Subsequent hydrolysis under conditions known to one skilled in the art supplies benzoic acid analogs of formula (10-2). Coupling of compounds of formula (10-2) with compounds of formula X—H, wherein the H is a hydrogen on a nitrogen atom contained within a heterocycle and X is said heterocycle as described in the Summary of the Invention, under amide bond coupling conditions gives compounds of formula (2-2). Examples of conditions known to generate amides from a mixture of a carboxylic acid and an amine include but are not limited to adding a coupling reagent such as but not limited to N-(3-dimethylaminopropyl)-N-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2-(3H-[1,2,3]triazolo[4,5-b]pyridin-3-yl)-1,1,3,3-tetramethylisouronium hexafluorophosphate(V). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, 2-methyltetrahydrofuran, N,N-dimethylformamide, dichloromethane, and ethyl acetate or mixtures thereof. The reaction may be conducted at ambient or elevated temperatures. Compounds of formula (2-2) are representative of compounds of formula (I).

Compounds of formula (4-2), wherein $R^3$, $R^4$, $R^5$ and $R^6$ are as defined for formula (II) can also be prepared as described in Scheme 11. Compounds of formula (11-1) can be reacted in the sequences described in Scheme 10 to give compounds of formula (4-2). Compounds of formula (4-2) are representative of compounds of formula (II).

It is appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

Example 1

3-[(8aR)-hexahydropyrrolo[1,2-a]pyrazin-2(1H)-ylcarbonyl]-N-[4-(trifluoromethyl)phenyl]benzenesulfonamide Step A:

To 3-(chlorosulfonyl)benzoyl chloride (0.359 g, 1.5 mmol) in anhydrous dichloromethane (80 mL) was added (R)-octahydropyrrolo[1,2-a]pyrazine (0.189 g, 1.5 mmol) in dichloromethane (4 mL) slowly over 10 minutes at room temperature. Then sodium carbonate (0.32 g, 2 mmol) was added, and the mixture was stirred at room temperature for 5 hours. Subsequently 4-(trifluoromethyl)aniline (2.42 g, 15 mmol) was added. The mixture was stirred at room temperature for 3 days, and then sodium carbonate (0.32 g, 3 mmol) and methanol (5 mL) were added. The mixture was stirred for 20 minutes, then filtered, and concentrated under reduced pressure. The residue was purified by chromatography on silica gel (methanol/ethyl acetate=1:10) to give the titled compound: $^1$H NMR (400 MHz, DMSO-d$_6$) δ ppm 1.10-1.90 (m, 6H), 2.10 (m, 1H), 2.70-3.15 (m, 5H), 4.40-4.60 (m, 1H), 7.30 (d, 2H, J=7 Hz), 7.63 (m, 4H), 7.76 (br s, 1H), 7.90 (m, 1H), 10.85 (br s, 1H); MS (ESI) m/z 454 (M+H)$^+$.

Step B:

To the above compound (560 mg, 1.236 mmol) was added 2 mL of 1 N HCl solution and 1 mL of methanol, and then the mixture was concentrated to dryness to give the HCl salt of the titled compound: $^1$H NMR (400 MHz, DMSO-d$_6$) δ ppm 1.60-2.20 (m, 4H), 2.90-3.90 (m, 8H), 4.60-4.80 (m, 1H), 7.35 (d, 2H, J=7 Hz), 7.62 (d, 2H, J=7 Hz), 7.72 (m, 2H), 7.92 (m, 2H), 11.06 (m, 1H), 11.50 (m, 1H); MS (ESI) m/z 454 (M+H)$^+$.

Example 2

N-(2-fluorophenyl)-3-[(8aR)-hexahydropyrrolo[1,2-a]pyrazin-2(1H)-ylcarbonyl]benzenesulfonamide Step A:

To ethyl 3-(chlorosulfonyl)benzoate (1 g, 4.02 mmol) in N,N-dimethylacetamide (13.4 mL) was added 2-fluoroaniline (1.551 mL, 16.08 mmol) dropwise over 1 minute at room temperature. The mixture was stirred at room temperature for 1 hour and then diluted with ethyl acetate (35 mL). The organic solution was washed with 1 N HCl (2×13 mL) and saturated NaCl (13 mL). The organic layer was concentrated, ethanol (38 mL) was added to the reside, and the mixture was concentrated to give ethyl 3-{[(2-fluorophenyl)amino]sulfonyl}benzoate.

Step B:

To the product of Step A was added ethanol (8 mL) followed by a solution of NaOH (0.483 g, 12.06 mmol) in water (8 mL). The reaction was stirred at ambient temperature for 45 minutes. To the mixture was added 1 N HCl (23 mL) and the mixture was stirred overnight. The solids were collected by filtration, washed with water (1×5 mL) and dried by vacuum filtration to give 3-{[(2-fluorophenyl)amino]sulfonyl}benzoic acid: $^1$H-NMR: (400 MHz, DMSO-d$_6$) δ ppm 13.97 (bs, 1H), 10.62 (bs, 1H), 8.26 (dd, 1H, J=1.6, 1.6, 3.2 Hz), 8.16 (ddd, 1H, J=8.1, 1.1, 1.1 Hz), 7.90 (ddd, 1H, J=8.1, 1.4, 1.4 Hz), 7.68 (dd, 1H, J=7.8, 7.8 Hz), 7.25-7.1 (m, 4H); MS (ESI) m/z 294.2 (M−H)$^-$.

Step C:

To a mixture of 3-{[(2-fluorophenyl)amino]sulfonyl}benzoic acid (800 mg, 2.71 mmol) and 2-(3H-[1,2,3]triazolo[4,5-h]pyridin-3-yl)-1,1,3,3-tetramethylisouronium hexafluorophosphate(V) (1133 mg, 2.98 mmol) in N,N-dimethylacetamide (6.5 mL) and 2-methyltetrahydrofuran (19.5 mL) was added (R)-octahydropyrrolo[1,2-a]pyrazine (479 mg, 3.79 mmol). The reaction was stirred at room temperature for 3 hours, diluted with 2-methyltetrahydrofuran (5 mL), and washed with saturated bicarbonate (2×25 mL). The combined aqueous layers were adjusted to pH 7 with buffer and re-extracted with 2-methyltetrahydrofuran (3×15 mL). The combined organic layers were concentrated under reduced pressure. The residue was taken up in ethanol (25 mL) and concentrated to give the title compound.

Step D:

To the product of Step C was added ethanol (25 mL) and then concentrated HCl (0.11 g, 2.98 mmol) in ethanol (1 mL) dropwise over 1 minute. The mixture was stirred at ambient temperature overnight and concentrated to afford the title compound as the hydrochloride salt: $^1$H NMR (400 MHz, DMSO-d6) δ ppm 11.35-11.05 (m, 1H), 10.30 (bs, 1H), 8.30-7.63 (m, 4H), 7.28-7.09 (m, 4H), 4.85-4.55 (m, 1H), 3.95-2.95 (m, 8H), 2.28-1.45 (m, 4H); MS (ESI) m/z 404.2 (M+H)$^+$.

Example 3

N-(3-fluorophenyl)-3-[(8aS)-hexahydropyrrolo[1,2-a]pyrazin-2(1H)-ylcarbonyl]benzenesulfonamide Step A:

To ethyl 3-(chlorosulfonyl)benzoate (1.0 g, 4.02 mmol) in N,N-dimethylacetamide (5 mL) was added 3-fluoroaniline (1.79 g, 16.08 mmol) dropwise over 30 seconds at room temperature. The mixture was stirred at room temperature for 4 hours, and then it was diluted with ethyl acetate (33 mL). The organic solution was washed with 1 N HCl (2×13 mL) and saturated NaCl (13 mL). The organic layer was concentrated, ethanol (8 mL) was added, and the mixture concentrated to give ethyl 3-{[(3-fluorophenyl)amino]sulfonyl}benzoate.

Step B:

To the product of Step A was added ethanol (6.4 mL) followed by a solution of NaOH (0.483 g, 12.1 mmol) in water (6.4 mL). The reaction was stirred at ambient temperature for 1 hour. To the mixture was added 1 N HCl (22.8 mL), and the mixture stirred at ambient temperature overnight. The solids were collected by filtration, washed with water (2×4 mL) and dried in a vacuum oven at 45° C. overnights to give 3-{[(3-fluorophenyl)amino]sulfonyl}benzoic acid: $^1$H NMR (400 MHz, DMSO-$d_6$) δ ppm 13.51 (bs, 1H), 10.68 (bs, 1H), 8.30 (t, J=1.8, 1H), 8.14 (dt, J=7.7, 1.4, 1H), 7.99 (ddd, J=7.8, 2.0, 1.1, 1H), 7.70 (t, J=7.8, 1H), 7.27 (m, 1H), 6.94-6.82 (m, 3H); MS (ESI) m/z 294 (M−H)$^-$.

Step C:

To 3-{[(3-fluorophenyl)amino]sulfonyl}benzoic acid (0.9 g, 3.05 mmol) and 2-(3H-[1,2,3]triazolo[4,5-b]pyridin-3-yl)-1,1,3,3-tetramethylisouronium hexafluorophosphate(V) (1.27 g, 3.35 mmol) in N,N-dimethylacetamide (6.4 mL) and 2-methyltetrahydrofuran (15 mL) was added (S)-octahydropyrrolo[1,2-a]pyrazine (0.55 g, 4.33 mmol) in 2-methyltetrahydrofuran (4 mL). The reaction was stirred at ambient temperature overnight and then diluted with 2-methyltetrahydrofuran (15 mL). The organic solution was washed with 6% NaHCO$_3$/6% NaCl (10 mL), and the aqueous layer was extracted with 2-methyltetrahydrofuran (15 mL). The combined organic layers were washed with 6% NaHCO$_3$/6% NaCl (10 mL), saturated NaCl (2×10 mL, 2×20 mL) and 1:1 saturated NaCl/water (2×20 mL), and then concentrated. The residue was concentrated from ethanol (2×10 mL) to give the title compound.

Step D:

To the product of Step C was added ethanol (25 mL) and then concentrated HCl (0.29 g, 3.0 mmol) in ethanol (1 mL) dropwise over 1 minute. The mixture was stirred at ambient temperature overnight and concentrated to afford the title compound as the hydrochloride salt: $^1$H NMR (400 MHz, DMSO-$d_6$/D$_2$O) δ ppm 7.95-7.78 (m, 2H), 7.75-7.58 (m, 2H), 7.34-7.17 (m, 1H), 7.00-6.77 (m, 3H), 4.74 (br d, J=60.9, 1H), 4.04-2.81 (m, 8H), 2.32-1.36 (m, 4H); MS (EST) m/z 402 (M+H)$^+$.

Example 4

N-(2,6-difluorophenyl)-3-[(8aS)-hexahydropyrrolo[1,2-a]pyrazin-2(1H)-ylcarbonyl]benzenesulfonamide Step A:

To 3-(chlorosulfonyl)benzoyl chloride (0.474 g, 1.98 mmol) in anhydrous dichloromethane (10 mL) was added (S)-octahydropyrrolo[1,2-a]pyrazine (0.250 g, 1.98 mmol) in dichloromethane (4 mL) slowly over 10 minutes at room temperature. Then sodium carbonate (0.420 g, 3.96 mmol) was added. The mixture was stirred at room temperature for 5 hours. Then 2,6-difluoroaniline (2.56 g, 19.81 mmol) was added. The mixture was stirred at room temperature overnight and then concentrated. The residue was purified by chromatography on silica gel (dichloromethane, then methanol/dichloromethane=1:10) to give the title compound.

Step B:

To the material from Step A (230 mg, 0.546 mmol) was added 2 mL of 1 N HCl solution, and 1 mL of methanol. The solid was dissolved, and then the mixture was concentrated to dryness to give the titled compound as the hydrochloride salt: $^1$H NMR (400 MHz, DMSO-$d_6$) δ ppm 1.71-1.95 (m, 4H), 2.99 (m, 2H), 3.25 (m, 2H), 3.43 (m, 2H), 3.81 (m, 2H), 4.72 (m, 1H), 7.13 (m, 2H), 7.38 (m, 1H), 7.75 (m, 3H), 10.35 (s, 1H), 11.46 (m, 1H); MS (ESI) m/z 422 (M+H)$^+$.

Example 5

N-(4-fluorophenyl)-3-[(8aS)-hexahydropyrrolo[1,2-a]pyrazin-2(1H)-ylcarbonyl]benzenesulfonamide The titled compound was prepared as the HCl salt using the procedures described in Example 4 substituting 4-fluoroaniline for 2,6-difluoroaniline: $^1$H NMR (400 MHz, DMSO-$d_6$) δ ppm 1.15-2.05 (m, 8H), 2.8-3.07 (m, 4H), 4.45 (m, 1H), 7.08 (m, 4H), 7.62 (m, 3H), 7.79 (m, 1H), 10.25 (br s, 1H); MS (ESI) m/z 404 (M+H)$^+$.

Example 6

3-[(8aS)-hexahydropyrrolo[1,2-a]pyrazin-2(1H)-ylcarbonyl]-N-[3-(trifluoromethyl)phenyl]benzenesulfonamide The titled compound was prepared using the procedure described in Example 4 Step A substituting 3-(trifluoromethyl)aniline for 2,6-difluoroaniline: $^1$H NMR (400 MHz, DMSO-$d_6$) δ ppm 1.15-2.05 (m, 8H), 2.75-3.02 (m, 4H), 4.46 (m, 1H), 7.42 (m, 4H), 7.66 (m, 3H), 7.84 (m, 1H), 10.75 (br s, 1H); MS (ESI) m/z 454 (M+H)$^+$.

Example 7

N-(3-fluorophenyl)-3-[(8aR)-hexahydropyrrolo[1,2-a]pyrazin-2(1H)-ylcarbonyl]benzenesulfonamide The titled compound was prepared as the HCl salt using the procedures described in Example 1 substituting 3-fluoroaniline for 4-(trifluoromethyl)aniline: $^1$H NMR (400 MHz, DMSO-$d_6$) δ ppm 1.65-2.10 (m, 4H), 2.85-3.85 (m, 8H), 4.60-4.80 (m, 1H), 6.90 (m, 3H), 7.29 (m, 1H), 7.68 (m, 2H), 7.90 (m, 2H), 10.85 (br s, 1H), 11.30 (m, 1H); MS (ESI) m/z 404 (M+H)$^+$.

Example 8

3-[(8aS)-hexahydropyrrolo[1,2-a]pyrazin-2(1H)-ylcarbonyl]-N-[4-(trifluoromethyl)phenyl]benzenesulfonamide The titled compound was prepared using the procedure described in Example 4 Step A substituting 4-(trifluoromethyl)aniline for 2,6-difluoroaniline: $^1$H NMR (400 MHz, DMSO-$d_6$) δ ppm 1.12-2.05 (m, 8H), 2.77-3.15 (m, 4H), 4.46 (m, 1H), 7.29 (d, 2H, J=8 Hz), 7.63 (m, 4H), 7.73 (s, 1H), 7.90 (m, 1H), 10.86 (br s, 1H); MS (ESI) m/z 454 (M+H)$^+$.

Example 9

N-(2-chlorophenyl)-3-[(8aR)-hexahydropyrrolo[1,2-a]pyrazin-2(1H)-ylcarbonyl]benzenesulfonamide The titled compound was prepared using the procedure described in Example 1, Step A substituting 2-chloroaniline for 4-(trifluoromethyl)aniline: $^1$H NMR (400 MHz, DMSO-$d_6$) δ ppm 1.23-2.08 (m, 8H), 2.79-3.02 (m, 4H), 4.47 (m, 1H), 7.30 (m, 4H), 7.67 (m, 3H), 7.76 (s, 1H), 10.08 (br s, 1H); MS (ESI) m/z 420 (M+H)$^+$.

Example 10

N-(2-chlorophenyl)-3-[(8aS)-hexahydropyrrolo[1,2-a]pyrazin-2(1H)-ylcarbonyl]benzenesulfonamide The titled compound was prepared using the procedure described in Example 4 Step A substituting 2-chloroaniline for 2,6-difluoroaniline: $^1$H NMR (400 MHz, DMSO-d$_6$) δ ppm 1.22-2.05 (m, 8H), 2.79-3.02 (m, 4H), 4.46 (m, 1H), 7.29 (m, 4H), 7.62 (m, 3H), 7.76 (s, 1H), 9.88 (br s, 1H); MS (ESI) m/z 420 (M+H)$^+$.

Example 11

N-(2,3-difluorophenyl)-3-[(8aS)-hexahydropyrrolo[1,2-a]pyrazin-2(1H)-ylcarbonyl]benzenesulfonamide The titled compound was prepared using the procedure described in Example 4 Step A substituting 2,3-difluoroaniline for 2,6-difluoroaniline: $^1$H NMR (400 MHz, DMSO-d$_6$) δ ppm 1.12-2.08 (m, 8H), 2.58-3.12 (m, 4H), 4.48 (m, 1H), 7.13 (m, 4H), 7.65 (m, 3H), 7.81 (m, 1H); MS (ESI) m/z 422 (M+H)$^+$.

Example 12

N-(2,5-difluorophenyl)-3-[(8aS)-hexahydropyrrolo[1,2-a]pyrazin-2(1H)-ylcarbonyl]benzenesulfonamide The titled compound was prepared using the procedure described in Example 4 Step A substituting 2,5-difluoroaniline for 2,6-difluoroaniline: $^1$H NMR (400 MHz, DMSO-d$_6$) δ ppm 1.30-2.30 (m, 8H), 2.60-2.90 (m, 4H), 4.47 (m, 1H), 7.09 (m, 3H), 7.67 (m, 3H), 7.82 (m, 1H); MS (ESI) m/z 422 (M+H)$^+$.

Example 13

N-(2,6-difluorophenyl)-3-[(8aR)-hexahydropyrrolo[1,2-a]pyrazin-2(1H)-ylcarbonyl]benzenesulfonamide Step A:
To ethyl 3-(chlorosulfonyl)benzoate (1.0 g, 4.02 mmol) in N,N-dimethylacetamide (6 mL) was added 2,6-difluoroaniline (2.03 g, 15.8 mmol) dropwise at room temperature. The mixture was stirred at room temperature for 5 hours and then diluted with ethyl acetate (40 mL). The organic solution was washed with 1 N HCl (2×15 mL and 3×30 mL) and saturated NaCl (30 mL). The organics were concentrated, ethanol (10 mL) was added, and the mixture was concentrated to give ethyl 3-{[(2,6-difluorophenyl)amino]sulfonyl}benzoate.

Step B:
To the product of Step A was added ethanol (8 mL) followed by a solution of 50% NaOH (0.96 g, 12.1 mmol) in water (8 mL). The reaction was stirred at ambient temperature for 1.5 hours. To the mixture was added dropwise 1 N HCl (28 mL), and the mixture was stirred at ambient temperature overnight. The solids were collected by filtration, washed with water (2×5 mL), and dried in a vacuum oven at 50° C. overnights to give 3-{[(2,6-difluorophenyl)amino]sulfonyl}benzoic acid: $^1$H NMR (400 MHz, DMSO-d$_6$) δ ppm 7.11 (t, J=8.1 Hz, 2H), 7.33-7.41 (m, 1H), 7.71 (t, J=7.7 Hz, 1H), 7.92 (dt, J=8.4, 1.1 Hz, 1H), 8.19 (dt, J=7.8, 1.1 Hz, 1H), 8.27 (t, J=1.51 Hz, 1H), 10.20 (s, 1H), 13.48 (s, 1H); MS (ESI) m/z 312 (M−H)$^-$.

Step C:
To 3-{[(2,6-difluorophenyl)amino]sulfonyl}benzoic acid (0.96 g, 3.06 mmol) and 2-(3H-[1,2,3]triazolo[4,5-b]pyridin-3-yl)-1,1,3,3-tetramethylisouronium hexafluorophosphate (V) (1.28 g, 3.37 mmol) in N,N-dimethylacetamide (7.4 mL) and 2-methyltetrahydrofuran (22 mL) was added (R)-octahydropyrrolo[1,2-a]pyrazine (0.54 g, 4.28 mmol). The reaction was stirred at ambient temperature for 5.5 hours, and then it was diluted with 2-methyltetrahydrofuran (15 mL). The organic solution was washed with 6% NaHCO$_3$/6% NaCl (35 mL), and the aqueous layer was extracted with 2-methyltetrahydrofuran (50 mL). The organic layer was washed with 6% NaHCO$_3$/6% NaCl (50 mL) and 1:1 saturated NaCl/water (6×15 mL), and then it was concentrated. The residue was concentrated from ethanol (2×10 mL) to give the title compound.

Step D:
To the product of Step C was added ethanol (13 mL) and then concentrated HCl (0.47 g, 4.8 mmol) in ethanol (1 mL) dropwise over 1 minute. The mixture was stirred at ambient temperature overnight and concentrated to afford the title compound as the hydrochloride salt: $^1$H NMR (400 MHz, DMSO-d$_6$) δ ppm 1.50-2.28 (m, 4H), 2.83-3.99 (m, 8H), 4.60-4.93 (br d J=65 Hz, 1H), 7.08-7.13 (m, 2H), 7.34-7.41 (m, 1H), 7.66-7.83 (m, 4H), 10.19 (s, 1H), 10.94-11.14 (m, 1H); MS (ESI) m/z 422 (M+H)$^+$.

Example 14

N-(2,3-difluorophenyl)-3-[(8aR)-hexahydropyrrolo[1,2-a]pyrazin-2(1H)-ylcarbonyl]benzenesulfonamide The titled compound was prepared using the procedure described in Example 1, Step A substituting 2,3-difluoroaniline for 4-(trifluoromethyl)aniline: $^1$H NMR (400 MHz, DMSO-d$_6$) δ ppm 1.12-2.08 (m, 8H), 2.58-3.12 (m, 4H), 4.48 (m, 1H), 7.13 (m, 3H), 7.65 (m, 3H), 7.81 (m, 1H); MS (ESI) m/z 422 (M+H)$^+$.

Example 15

N-(2,5-difluorophenyl)-3-[(8aR)-hexahydropyrrolo[1,2-a]pyrazin-2(1H)-ylcarbonyl]benzenesulfonamide The titled compound was prepared using the procedure described in Example 1, Step A substituting 2,5-difluoroaniline for 4-(trifluoromethyl)aniline: $^1$H NMR (400 MHz, DMSO-d$_6$) δ ppm 1.30-2.30 (m, 8H), 2.60-2.90 (m, 4H), 4.47 (m, 1H), 7.09 (m, 3H), 7.67 (m, 3H), 7.82 (m, 1H); MS (ESI) m/z 422 (M+H)$^+$.

Example 16

N-(2,4-difluorophenyl)-3-[(8aS)-hexahydropyrrolo[1,2-a]pyrazin-2(1H)-ylcarbonyl]benzenesulfonamide The titled compound was prepared using the procedure described in Example 4 Step A substituting 2,4-difluoroaniline for 2,6-difluoroaniline: $^1$H NMR (400 MHz, DMSO-d$_6$) δ ppm 1.26 (m, 2H), 1.67 (m, 2H), 1.85 (m, 2H), 2.06 (m, 2H), 2.87 (m, 2H), 2.99 (m, 2H), 4.49 (m, 1H), 7.05 (m, 1H), 7.24 (m, 2H), 7.63 (m, 3H), 7.75 (m, 1H); MS (ESI) m/z 422 (M+H)$^+$.

Example 17

N-(2-fluorophenyl)-3-[(8aS)-hexahydropyrrolo[1,2-a]pyrazin-2(1H)-ylcarbonyl]benzenesulfonamide Step A:

To 3-(chlorosulfonyl)benzoyl chloride (0.521 g, 2.18 mmol) in anhydrous dichloromethane (10 mL) was added (S)-octahydropyrrolo[1,2-a]pyrazine (0.250 g, 1.98 mmol) in dichloromethane (4 mL) slowly over 10 minutes at room temperature. The mixture was stirred at room temperature for 5 hours. Then 2-fluoroaniline (1.54 g, 13.87 mmol) was added. The mixture was stirred at room temperature overnight and then concentrated. The residue was purified by chromatography on silica gel (dichloromethane, then methanol/dichloromethane=1:10) to give the titled compound.

Step B:

To the product of Step A (339 mg, 0.84 mmol) was added 2 mL of 1 N HCl solution, and 1 mL of methanol. The mixture was stirred until homogeneous, and then the mixture was concentrated to dryness to give the titled compound as the corresponding HCl salt: $^1$H NMR (400 MHz, DMSO-$d_6$) δ 1.60 (m, 2H), 1.99 (m, 4H), 2.95 (m, 3H), 3.67 (m, 3H), 4.75 (m, 1H), 7.19 (m, 4H), 7.75 (m, 4H), 10.25 (s, 1H), 11.35 (br s, 1H, HCl); MS (ESI): m/z 404 (M+H)$^+$.

Example 18

N-(2,4-difluorophenyl)-3-[(8aR)-hexahydropyrrolo[1,2-a]pyrazin-2(1H)-ylcarbonyl]benzenesulfonamide The titled compound was prepared using the procedure described in Example 1 Step A substituting 2,4-difluoroaniline for 4-(trifluoromethyl)aniline: $^1$H NMR (400 MHz, DMSO-$d_6$) δ ppm 1.26 (m, 2H), 1.67 (m, 2H), 1.85 (m, 2H), 2.06 (m, 2H), 2.87 (m, 2H), 2.99 (m, 2H), 4.49 (m, 1H), 7.05 (m, 1H), 7.24 (m, 2H), 7.63 (m, 3H), 7.75 (m, 1H); MS (ESI) m/z 422 (M+H)$^+$.

Example 19

3-[(8aS)-hexahydropyrrolo[1,2-a]pyrazin-2(1H)-ylcarbonyl]-N-[2-(trifluoromethyl)phenyl]benzenesulfonamide The titled compound was prepared using the procedure described in Example 4 Step A substituting 2-(trifluoromethyl)aniline for 2,6-difluoroaniline: $^1$H NMR (400 MHz, DMSO-$d_6$) δ ppm 1.33-1.83 (m, 4H), 2.14-2.25 (m, 4H), 2.65-3.07 (m, 4H), 4.46 (m, 1H), 7.14 (m, 1H), 7.27 (m, 1H), 7.48 (m, 1H), 7.63 (m, 4H), 7.69 (s, 1H), 7.83 (m, 1H); MS (ESI) m/z 454 (M+H)$^+$.

Example 20

4-chloro-2-fluoro-N-(2-fluorophenyl)-5-[(8aR)-hexahydropyrrolo[1,2-a]pyrazin-2(1H)-ylcarbonyl]benzenesulfonamide Step A:

To Ethyl 2-chloro-5-(chlorosulfonyl)-4-fluorobenzoate (1.0 g, 3.32 mmol) in N,N-dimethylacetamide (5 mL) was added 2-fluoroaniline (1.48 g, 13.28 mmol) dropwise over 30 seconds at room temperature. The mixture was stirred at room temperature for 2 hours, and then it was diluted with ethyl acetate (33 mL). The organic solution was washed with 1 N HCl (2×13 mL) and saturated NaCl (13 mL). The organic layer was concentrated, ethanol (8 mL) was added, and the mixture concentrated to give ethyl 2-chloro-4-fluoro-5-{[(2-fluorophenyl)amino]sulfonyl}benzoate.

Step B:

To ethyl 2-chloro-4-fluoro-5-{[(2-fluorophenyl)amino]sulfonyl}benzoate (1.45 g) was added ethanol (6.4 mL) followed by a solution of NaOH (0.398 g, 9.96 mmol) in water (6.4 mL). The reaction was stirred at ambient temperature for 1 hour. To the mixture was added 1 N HCl (22.8 mL), and the mixture was stirred for 30 minutes. The solids were collected by filtration, washed with water (2×4 mL), and dried in a vacuum oven at 45° C. for 2.5 days to give 2-chloro-4-fluoro-5-{[(2-fluorophenyl)amino]sulfonyl}benzoic acid: $^1$H NMR (400 MHz, DMSO-$d_6$) δ ppm 13.89 (s, 1H), 10.67 (s, 1H), 8.09 (d, J=7.7, 1H), 7.88 (d, J=9.9, 1H), 7.32-7.11 (m, 4H); MS (ESI) m/z 346 (M−H)$^-$.

Step C:

To 2-chloro-4-fluoro-5-{[(2-fluorophenyl)amino]sulfonyl}benzoic acid (0.9 g, 2.59 mmol) and 2-(3H-[1,2,3]triazolo[4,5-b]pyridin-3-yl)-1,1,3,3-tetramethylisouronium hexafluorophosphate(V) (1.08 g, 2.85 mmol) in N,N-dimethylacetamide (6.4 mL) and 2-methyltetrahydrofuran (15 mL) was added (R)-octahydropyrrolo[1,2-a]pyrazine (0.46 g, 3.68 mmol) in 2-methyltetrahydrofuran (4 mL). The reaction was stirred at ambient temperature overnight and diluted with 2-methyltetrahydrofuran (15 mL). The organic solution was washed with 6% NaHCO$_3$/6% NaCl (10 mL), and the aqueous layer was extracted with 2-methyltetrahydrofuran (15 mL). The combined organic layers were washed with 6% NaHCO$_3$/6% NaCl (10 mL) and saturated NaCl (2×10 mL), and then concentrated. The residue was concentrated from ethanol (2×10 mL) to give the title compound.

Step D:

To the product of Step C was added ethanol (25 mL) and then concentrated HCl (0.29 g, 3.0 mmol) in ethanol (1 mL) dropwise over 1 minute. The mixture was stirred at ambient temperature for 30 minutes, and the solids were collected by filtration. The product was washed with ethanol and dried in a vacuum oven at room temperature to give the hydrochloride salt of the title compound: $^1$H NMR (400 MHz, DMSO-$d_6$/D$_2$O) δ ppm 8.28-7.65 (m, 2H), 7.50-7.07 (m, 4H), 4.71 (br d, J=65.4, 1H), 4.2-2.8 (m, 8H), 2.33-1.38 (m, 4H); MS (ESI) m/z 456 (M+H)$^+$. Diffraction patterns were collected at ambient conditions in reflection mode using Cu—Kα1 (λ=1.54060 Å) radiation. The diffractometer is equipped with a position sensitive detector that is calibrated at 1 degree intervals using the direct beam. Calibration is verified with a NIST standard. Main characteristic diffraction peak positions (degrees 2-theta±0.1) based on a diffraction pattern collected under aforementioned conditions are as follows: 8.0, 14.9, 15.7, 16.4, 21.0, 22.0, 22.8.

Example 21

N-(3-chlorophenyl)-3-[(8aS)-hexahydropyrrolo[1,2-a]pyrazin-2(1H)-ylcarbonyl]benzenesulfonamide The titled compound was prepared using the procedure described in Example 4 Step A substituting 3-chloroaniline for 2,6-difluoroaniline: $^1$H NMR (400 MHz, DMSO-$d_6$) δ ppm 1.27-2.05 (m, 8H), 2.80-3.15 (m, 4H), 4.49 (m, 1H), 7.08 (m, 3H), 7.27 (m, 1H), 7.66 (m, 3H), 7.85 (m, 1H), 10.61 (br s, 1H); MS (ESI) m/z 422 (M+H)$^+$.

Example 22

(8aR)-2-[3-({4-[bis(4-fluorophenyl)methyl]piperazin-1-yl}sulfonyl)benzoyl]octahydropyrrolo[1,2-a]pyrazine The titled compound was prepared using the procedure described in Example 1 Step A substituting 1-(bis(4-fluorophenyl)methyl)piperazine (1 equivalent) for 4-(trifluoromethyl)aniline: $^1$H NMR (500 MHz, DMSO-$d_6$) δ ppm 1.20-1.40 (m, 2H), 1.60 (m, 3H), 1.80-2.20 (3H), 2.35 (m, 4H), 2.90-3.10 (m, 8H), 3.20 (m, 1H), 4.45-4.60 (m, 1H), 7.10 (m, 4H), 7.39 (m, 4H), 7.63 (br s, 1H), 7.80 (m, 3H); MS (ESI) m/z 581 (M+H)$^+$.

Example 23

(8aS)-2-[3-({4-[bis(4-fluorophenyl)methyl]piperazin-1-yl}sulfonyl)benzoyl]octahydropyrrolo[1,2-a]pyrazine The titled compound was prepared using the procedure described in Example 4 Step A substituting 1-(bis(4-fluorophenyl)methyl)piperazine (1 equivalent) for 2,6-difluoroaniline: $^1$H NMR (400 MHz, DMSO-$d_6$) δ ppm 1.59 (m, 2H), 1.69 (m, 2H), 1.91 (m, 2H), 2.07 (m, 2H), 2.33 (m, 4H), 2.93 (m, 4H), 3.02 (m, 2H), 3.52 (m, 2H), 4.39 (s, 1H), 4.49 (m, 1H), 7.08 (t, 4H, J=8 Hz), 7.37 (t, 4H, J=8 Hz), 7.66 (s, 1H), 7.77 (m, 2H), 7.80 (m, 1H); MS (ESI) m/z 581 (M+H)$^+$.

Example 24

(8aR)-2-{3-[(4-benzhydrylpiperazin-1-yl)sulfonyl]benzoyl}octahydropyrrolo[1,2-a]pyrazine The titled compound was prepared using the procedure described in Example 1 Step A substituting 1-benzhydrylpiperazine (1 equivalent) for 4-(trifluoromethyl)aniline: $^1$H NMR (500 MHz, DMSO-$d_6$) δ ppm 1.20-1.40 (m, 2H), 1.63 (m, 3H), 1.80-2.16 (3H), 2.35 (m, 4H), 2.92-3.20 (m, 8H), 3.40-3.55 (m, 1H), 4.45-4.62 (m, 1H), 7.15 (m, 2H), 7.25 (m, 4H), 7.38 (m, 4H), 7.62 (br s, 1H), 7.80 (m, 3H); MS (ESI) m/z 545 (M+H)$^+$.

Example 25

N-(3-chlorophenyl)-3-[(8aR)-hexahydropyrrolo[1,2-a]pyrazin-2(1H)-ylcarbonyl]benzenesulfonamide The titled compound was prepared using the procedure described in Example 1 Step A substituting 3-chloroaniline for 4-(trifluoromethyl)aniline: $^1$H NMR (400 MHz, DMSO-$d_6$) δ ppm 1.27-2.05 (m, 8H), 2.80-3.15 (m, 4H), 4.49 (m, 1H), 7.08 (m, 3H), 7.27 (m, 1H), 7.66 (m, 3H), 7.85 (m, 1H), 10.61 (br s, 1H); MS (ESI) m/z 421 (M+H)$^+$.

Example 26

N-(2,2-diphenylethyl)-3-[(8aR)-hexahydropyrrolo[1,2-a]pyrazin-2(1H)-ylcarbonyl]benzenesulfonamide The titled compound was prepared using the procedure described in Example 1 Step A substituting 2,2-diphenylethanamine (1 equivalent) for 4-(trifluoromethyl)aniline: $^1$H NMR (500 MHz, DMSO-$d_6$) δ ppm 1.10 (m, 1H), 1.36 (m, 1H), 1.50-1.90 (m, 5H), 1.95-2.15 (3H), 2.80-3.40 (4H), 3.98 (t, 1H, J=8 Hz), 4.46-4.58 (m, 1H), 7.16 (m, 2H), 7.26 (m, 8H), 7.63 (m, 2H), 7.72 (br s, 1H), 7.82 (m, 2H); MS (ESI) m/z 490 (M+H)$^+$.

Example 27

3-[(8aR)-hexahydropyrrolo[1,2-a]pyrazin-2(1H)-ylcarbonyl]-N-[2-(trifluoromethyl)phenyl]benzenesulfonamide The titled compound was prepared using the procedure described in Example 1 Step A substituting 2-(trifluoromethyl)aniline for 4-(trifluoromethyl)aniline: $^1$H NMR (400 MHz, DMSO-$d_6$) δ ppm 1.33-1.83 (m, 4H), 2.14-2.25 (m, 4H), 2.65-3.07 (m, 4H), 4.46 (m, 1H), 7.14 (m, 1H), 7.27 (m, 1H), 7.48 (m, 1H), 7.63 (m, 4H), 7.69 (s, 1H), 7.83 (m, 1H); MS (ESI) m/z 454 (M+H)$^+$.

Example 28

(8aS)-2-{3-[(4-benzhydrylpiperazin-1-yl)sulfonyl]benzoyl}octahydropyrrolo[1,2-a]pyrazine The titled compound was prepared using the procedure described in Example 4 Step A substituting 1-benzhydrylpiperazine (1 equivalent) for 2,6-difluoroaniline: $^1$H NMR (400 MHz, DMSO-$d_6$) δ ppm 1.27 (m, 2H), 1.63 (m, 2H), 1.91 (m, 2H), 2.08 (m, 2H), 2.37 (m, 4H), 2.94 (m, 4H), 3.02 (m, 2H), 3.54 (m, 2H), 4.30 (s, 1H), 4.53 (m, 1H), 7.16 (t, 2H, J=8 Hz), 7.24 (t, 4H, J=8 Hz), 7.35 (d, 4H, J=8 Hz), 7.66 (s, 1H), 7.77 (m, 2H), 7.80 (m, 1H); MS (ESI) m/z 545 (M+H)$^+$.

Example 29

N-(3,3-diphenylpropyl)-3-[(8aR)-hexahydropyrrolo[1,2-a]pyrazin-2(1H)-ylcarbonyl]benzenesulfonamide The titled compound was prepared using the procedure described in Example 1 Step A substituting 3,3-diphenylpropan-1-amine (1 equivalent) for 4-(trifluoromethyl)aniline: $^1$H NMR (500 MHz, DMSO-$d_6$) δ ppm 1.15 (m, 1H), 1.38 (m, 1H), 1.50-1.90 (m, 5H), 1.96-2.10 (m, 3H), 2.62 (m, 2H), 2.78-3.10 (m, 3H), 3.42 (m, 1H), 3.97 (t, 1H, J=8 Hz), 4.46-4.58 (m, 1H), 7.16-7.26 (m, 10H), 7.62 (m, 2H), 7.70 (br s, 1H), 7.80 (m, 2H); MS (ESI) m/z 504 (M+H)$^+$.

Example 30

N-(3,3-diphenylpropyl)-3-[(8aS)-hexahydropyrrolo[1,2-a]pyrazin-2(1H)-ylcarbonyl]benzenesulfonamide The titled compound was prepared using the procedure described in Example 4 Step A substituting 3,3-diphenylpropan-1-amine (1 equivalent) for 2,6-difluoroaniline: $^1$H NMR (400 MHz, DMSO-$d_6$) δ ppm 1.25 (m, 2H), 1.68 (m, 2H), 1.85 (m, 2H), 2.03 (m, 2H), 2.11 (m, 2H), 2.66 (m, 2H), 2.99 (m, 2H), 3.09 (m, 2H), 3.97 (m, 1H), 4.52 (m, 1H), 7.14 (t, 2H, J=8 Hz), 7.19 (d, 4H, J=8 Hz), 7.24 (t, 4H, J=8 Hz), 7.65 (m, 2H), 7.70 (s, 1H), 7.80 (m, 2H); MS (ESI) m/z 504 (M+H)$^+$.

Example 31

N-(2,2-diphenylethyl)-3-[(8aS)-hexahydropyrrolo[1,2-a]pyrazin-2(1H)-ylcarbonyl]benzenesulfonamide The titled compound was prepared using the procedure described in Example 4 Step A substituting 2,2-diphenylethanamine (1 equivalent) for 2,6-difluoroaniline: $^1$H NMR (400 MHz, DMSO-$d_6$) δ ppm 1.37 (m, 2H), 1.53 (m, 2H), 1.83 (m, 2H), 2.03 (m, 2H), 2.84 (m, 2H), 2.99 (m, 2H), 3.39 (m, 2H), 4.10 (m, 1H), 4.52 (m, 1H), 7.18 (m, 2H), 7.29 (m, 8H), 7.64 (m, 2H), 7.74 (s, 1H), 7.83 (m, 2H); MS (ESI) m/z 490 (M+H)$^+$.

Example 32

4-chloro-3-[(8aR)-hexahydropyrrolo[1,2-a]pyrazin-2 (1H)-ylcarbonyl]-N-[4-(trifluoromethyl)phenyl]benzenesulfonamide To 2-chloro-5-(chlorosulfonyl)benzoic acid (0.51 g, 2.0 mmol) was added dichloromethane (10 mL), oxalyl chloride (1.5 mL) and one small drop of N,N-dimethylformamide. The mixture was stirred at room temperature for 3 days. The mixture was then concentrated until oxalyl chloride was gone to give 2-chloro-5-(chlorosulfonyl)benzoyl chloride. The residue was used without purification.

To crude 2-chloro-5-(chlorosulfonyl)benzoyl chloride (2 mmol) in anhydrous dichloromethane (50 mL) was added (R)-octahydropyrrolo[1,2-a]pyrazine (0.252 g, 2 mmol) in dichloromethane (4 mL) slowly over 10 minutes at room temperature. Then sodium carbonate (0.46 g, 4.4 mmol) was added. The mixture was stirred at room temperature overnight. Then dichloromethane was removed by concentration, and 4-(trifluoromethyl)aniline (3.22 g, 20 mmol) was added. The mixture was stirred at 70° C. overnight. Then sodium carbonate (0.21 g, 2 mmol) and methanol (5 mL) were added at room temperature. The mixture was stirred for 30 minutes, then filtered, and concentrated. The residue was purified by chromatography on silica gel (ethyl acetate, then methanol/ethyl acetate=1:10) to give the titled compound: $^1$H NMR (500 MHz, DMSO-$d_6$) δ ppm 1.30 (m, 1H), 1.55 (m, 1H), 1.70-2.00 (m, 4H), 2.60 (m, 2H), 2.80-3.50 (m, 4H), 4.40-4.60 (m, 1H), 7.30 (m, 2H), 7.62 (m, 2H), 7.82 (m, 3H), 11.00 (br s, 1H); MS (ESI) m/z 488 (M+H)$^+$.

Example 33

N-[2-(4-fluorophenyl)ethyl]-3-[(8aS)-hexahydropyrrolo[1,2-a]pyrazin-2(1H)-ylcarbonyl]benzenesulfonamide The titled compound was prepared using the procedure described in Example 4 Step A substituting 2-(4-fluorophenyl)ethanamine (1 equivalent) for 2,6-difluoroaniline: $^1$H NMR (400 MHz, DMSO-$d_6$) δ ppm 1.24 (m, 2H), 1.64 (m, 2H), 1.86 (m, 2H), 2.06 (m, 2H), 2.67 (m, 2H), 2.88 (m, 2H), 2.98 (m, 2H), 3.43 (m, 2H), 4.52 (m, 1H), 7.07 (t, 2H, J=8 Hz), 7.19 (t, 2H, J=8 Hz), 7.65 (m, 2H), 7.74 (s, 1H), 7.82 (m, 2H); MS (ESI) m/z 432 (M+H)$^+$.

Example 34

2-chloro-5-[(8aR)-hexahydropyrrolo[1,2-a]pyrazin-2 (1H)-ylcarbonyl]-N-[4-(trifluoromethyl)phenyl]benzenesulfonamide The titled compound was prepared using the procedure described in Example 32 substituting 4-chloro-3-(chlorosulfonyl)benzoic acid for 2-chloro-5-(chlorosulfonyl)benzoic acid: $^1$H NMR (500 MHz, DMSO-$d_6$) δ ppm 1.40-1.60 (m, 2H), 1.80-2.05 (m, 4H), 2.75 (m, 2H), 2.95-3.50 (m, 4H), 4.20-4.45 (m, 1H), 7.30 (d, 2H, J=8 Hz), 7.62 (d, 2H, J=8 Hz), 7.78 (m, 2H), 8.15 (s, 1H), 11.10 (br s, 1H); MS (ESI) m/z 488 (M+H)$^+$.

Example 35

(8aS)-2-(3-{[4-(4-fluorophenyl)piperazin-1-yl] sulfonyl}benzoyl)octahydropyrrolo[1,2-a]pyrazine The titled compound was prepared using the procedure described in Example 4 Step A substituting 1-(4-fluorophenyl)piperazine (1 equivalent) for 2,6-difluoroaniline: $^1$H NMR (400 MHz, DMSO-$d_6$) δ ppm 1.20 (m, 2H), 1.63 (m, 2H), 1.86 (m, 2H), 2.07 (m, 2H), 2.88 (m, 2H), 2.93 (m, 2H), 3.06 (m, 4H), 3.14 (m, 4H), 4.52 (m, 1H), 6.93 (m, 2H), 7.04 (m, 2H), 7.72 (s, 1H), 7.75 (m, 2H), 7.85 (m, 1H); MS (ESI) m/z 473 (M+H)$^+$.

Example 36

N-1,1'-biphenyl-2-yl-3-[(8aS)-hexahydropyrrolo[1,2-a]pyrazin-2(1H)-ylcarbonyl]benzenesulfonamide The titled compound was prepared using the procedure described in Example 4 Step A substituting biphenyl-2-amine for 2,6-difluoroaniline: $^1$H NMR (400 MHz, DMSO-$d_6$) δ ppm 1.26 (m, 2H), 1.67 (m, 2H), 1.83 (m, 2H), 2.05 (m, 2H), 2.85 (m, 2H), 2.99 (m, 2H), 4.50 (m, 1H), 7.04 (m, 1H), 7.28 (m, 8H), 7.57 (m, 4H), 9.65 (s, 1H); MS (ESI) m/z 462 (M+H)$^+$.

Example 37

3-(octahydro-2H-pyrido[1,2-a]pyrazin-2-ylcarbonyl)-N-[4-(trifluoromethyl)phenyl]benzenesulfonamide Step A:
To ethyl 3-(chlorosulfonyl)benzoate (4.0 g, 16.08 mmol) in N,N-dimethylacetamide (20 mL) was added 4-(trifluoromethyl)aniline (10.37 g, 64.3 mmol) dropwise at room temperature. The mixture was stirred at room temperature for 2.5 hours, and then it was diluted with ethyl acetate (130 mL). The organic solution was washed with 1 N HCl (2×60 mL) and saturated NaCl (60 mL). The organic layer was concentrated, ethanol (40 mL) was added, and the mixture was concentrated to give ethyl 3-({[4-(trifluoromethyl)phenyl] amino}sulfonyl)benzoate.

Step B:
To the product of Step A was added ethanol (25 mL) followed by a solution of NaOH (1.93 g, 48.3 mmol) in water (25 mL). The reaction was stirred at ambient temperature for 1.5 hours. To the mixture was added dropwise 1 N HCl (95 mL), and the mixture was stirred at ambient temperature overnight. The solids were collected by filtration, washed with water (2×20 mL), and dried in a vacuum oven at 45° C. overnights to give 3-({[4-(trifluoromethyl)phenyl] amino}sulfonyl)benzoic acid: $^1$H NMR (400 MHz, DMSO-$d_6$) δ ppm 7.28 (d, J=8.4 Hz, 2H), 7.62 (d, J=8.5 Hz, 2H), 7.71 (t, J=7.8 Hz, 1H), 8.03 (ddd, J=7.8, 1.9, 1.1 Hz, 1H), 8.15 (dt, J=7.8, 1.4 Hz, 1H), 8.34 (t, J=1.7 Hz, 1H), 10.98 (s, 1H), 13.54 (s, 1H); MS (EST) m/z 344 (M–H)$^-$.

Step C:
To 3-({[4-(trifluoromethyl)phenyl]amino}sulfonyl)benzoic acid (4.35 g, 12.6 mmol) and 2-(3H-[1,2,3]triazolo[4,5-b]pyridin-3-yl)-1,1,3,3-tetramethylisouronium hexafluorophosphate(V) (5.27 g, 13.9 mmol) in N,N-dimethylacetamide (30 mL) and 2-methyltetrahydrofuran (90 mL) was added 1,4-diazabicyclo[4.4.0]decane (2.47 g, 17.6 mmol). The reaction was stirred at ambient temperature for 2.5 hours, and then it was diluted with 2-methyltetrahydrofuran (57 mL). The organic solution was washed with 6% $NaHCO_3$/6% NaCl (35 mL), and the aqueous layer was extracted with 2-methyltetrahydrofuran (50 mL). The organic layer was washed with 6% $NaHCO_3$/6% NaCl (50 mL) and 1:1 saturated NaCl/water (6×50 mL), and then it was concentrated. The residue was concentrated from ethanol (2×50 mL) to give the title compound.

Step D:

To the product of Step C was added ethanol (100 mL) and then concentrated HCl (1.6 g, 16.2 mmol) in ethanol (2 mL) dropwise over 1 minute. The mixture was stirred at ambient for 4.5 hours. The solids were collected by filtration, washed with ethanol (15 mL), and dried overnight at 55° C. to yield the title compound as the hydrochloride salt: $^1$H NMR (400 MHz, DMSO-$d_6$) δ ppm 1.23-1.99 (m, 6H), 2.79-3.65 (m, 8H), 4.53 (s, 1H), 7.31 (d, J=8.4 Hz, 2H), 7.61 (d, J=8.4 Hz, 2H), 7.66-7.72 (m, 2H), 7.91-7.93 (m, 2H), 11.07 (s, 2H); MS (ESI) m/z 468 (M+H)$^+$. Diffraction patterns were collected at ambient conditions in reflection mode using Cu—Kα1 (λ=1.54060 Å) radiation. The diffractometer is equipped with a position sensitive detector that is calibrated at 1 degree intervals using the direct beam. Calibration is verified with a NIST standard. Main characteristic diffraction peak positions (degrees 2-theta±0.1) based on a diffraction pattern collected under aforementioned conditions are as follows: 6.2, 12.8, 15.2, 15.7, 17.5, 18.8, 20.3.

Example 38

3-(octahydro-2H-pyrido[1,2-a]pyrazin-2-ylcarbonyl)-N-[3-(trifluoromethyl)phenyl]benzenesulfonamide To 3-(chlorosulfonyl)benzoyl chloride (0.36 g 1.5 mmol) in anhydrous dichloromethane (50 mL) was added octahydro-1H-pyrido[1,2-a]pyrazine (0.21 g, 1.5 mmol) in dichloromethane (4 mL) slowly over 10 minutes at room temperature. Then sodium carbonate (0.32 g, 3 mmol) was added. The mixture was stirred at room temperature for 5 hours. Then 3-(trifluoromethyl)aniline (2.9 g, 18 mmol) was added. The mixture was stirred at room temperature for 5 days, then sodium carbonate (0.32 g, 3 mmol) and methanol (5 mL) were added, the mixture was stirred for 20 minutes, then filtered, and concentrated. The residue was purified by chromatography on silica gel (methanol/ethyl acetate=1:10) to give the titled compound: $^1$H NMR (400 MHz, DMSO-$d_6$) δ ppm 1.00-1.27 (m, 3H), 1.42-2.10 (m, 7H), 2.70-3.40 (m, 4H), 4.25-4.40 (m, 1H), 7.40 (m, 3H), 7.50 (m, 1H), 7.70 (m, 3H), 7.85 (m, 1H), 10.80 (br s, 1H); MS (ESI) m/z 468 (M+H)$^+$.

Example 39

N-(2-fluorophenyl)-3-(octahydro-2H-pyrido[1,2-a]pyrazin-2-ylcarbonyl)benzenesulfonamide The titled compound was prepared using the procedure described in Example 38 substituting 2-fluoroaniline for 4-(trifluoromethyl)aniline: $^1$H NMR (400 MHz, DMSO-$d_6$) δ ppm 1.05-1.30 (m, 3H), 1.45-1.70 (m, 4H), 1.80-2.10 (m, 3H), 2.70-3.40 (m, 4H), 4.30-4.40 (m, 1H), 7.17 (m, 2H), 7.22 (m, 2H), 7.63 (m, 3H), 7.80 (br s, 1H), 10.20 (br s, 1H); MS (ESI) m/z 418 (M+H)$^+$.

Example 40

N-(4-fluorophenyl)-3-[(4-pyrrolidin-1-ylpiperidin-1-yl)carbonyl]benzenesulfonamide To 3-(chlorosulfonyl)benzoyl chloride (0.178 g, 0.746 mmol) in anhydrous dichloromethane (10 mL) was added 4-(pyrrolidin-1-yl)piperidine (0.115 g, 0.746 mmol) in dichloromethane (4 mL) slowly over 10 minutes at room temperature. Then sodium carbonate (0.277 g, 2.61 mmol) was added. The mixture was stirred at room temperature for 5 hours. Then 4-fluoroaniline (0.83 g, 7.5 mmol) was added. The mixture was stirred at room temperature overnight. Then methanol (5 mL) was added, the mixture was stirred for 20 minutes, then filtered, and concentrated. The residue was purified by chromatography on silica gel (ethyl acetate, then methanol/ethyl acetate=1:10) to give the titled compound: $^1$H NMR (400 MHz, DMSO-$d_6$) δ ppm 1.37 (m, 2H), 1.73 (m, 6H), 1.93 (m, 2H), 2.63 (m, 4H), 2.96 (m, 2H), 4.25 (m, 1H), 7.08 (m, 4H), 7.62 (m, 3H), 7.79 (m, 1H); MS (ESI) m/z 432 (M+H)$^+$.

Example 41

N-phenyl-3-[(4-pyrrolidin-1-ylpiperidin-1-yl)carbonyl]benzenesulfonamide

The titled compound was prepared using the procedure described in Example 40 substituting aniline for 4-fluoroaniline: $^1$H NMR (400 MHz, DMSO-$d_6$) δ ppm 1.38 (m, 2H), 1.74 (m, 6H), 1.93 (m, 2H), 2.74 (m, 4H), 2.93 (m, 2H), 4.25 (m, 1H), 7.07 (m, 3H), 7.23 (m, 2H), 7.62 (m, 3H), 7.81 (s, 1H); MS (ESI) m/z 414 (M+H)$^+$.

Example 42

3-[(4-pyrrolidin-1-ylpiperidin-1-yl)carbonyl]-N-[4-(trifluoromethyl)phenyl]benzenesulfonamide The titled compound was prepared using the procedure described in Example 40 substituting 4-(trifluoromethyl)aniline for 4-fluoroaniline: $^1$H NMR (400 MHz, DMSO-$d_6$) δ ppm 1.37 (m, 2H), 1.74 (m, 6H), 1.93 (m, 2H), 2.66 (m, 4H), 2.9 (m, 2H), 4.28 (m, 1H), 7.24 (m, 2H), 7.62 (m, 5H), 7.75 (m, 1H); MS (ESI) m/z 482 (M+H)$^+$.

Example 43

3-[(4-pyrrolidin-1-ylpiperidin-1-yl)carbonyl]-N-[3-(trifluoromethyl)phenyl]benzenesulfonamide The titled compound was prepared using the procedure described in Example 40 substituting 3-(trifluoromethyl)aniline for 4-fluoroaniline: $^1$H NMR (400 MHz, DMSO-$d_6$) δ ppm 1.51 (m, 2H), 1.84 (m, 6H), 2.07 (m, 2H), 2.86 (m, 4H), 3.05 (m, 2H), 4.43 (m, 1H), 7.44 (m, 4H), 7.68 (m, 3H), 7.87 (m, 1H), 10.81 (br s, 1H, NH); MS (ESI) m/z 482 (M+H)$^+$.

Example 44

N-(3-fluorophenyl)-3-[(4-pyrrolidin-1-ylpiperidin-1-yl)carbonyl]benzenesulfonamide The titled compound was prepared using the procedure described in Example 40 substituting 3-fluoroaniline for 4-fluoroaniline: $^1$H NMR (400 MHz, DMSO-$d_6$) δ ppm 1.60 (m, 2H), 1.88 (m, 6H), 2.07 (m, 2H), 2.84 (m, 4H), 3.07 (m, 2H), 4.43 (m, 1H), 6.91 (m, 3H), 7.29 (m, 1H), 7.65 (m, 2H), 7.74 (s, 1H), 7.87 (m, 1H), 10.85 (br s, 1H NH); MS (ESI) m/z 432 (M+H)$^+$.

Example 45

N-(2-fluorophenyl)-3-[(4-pyrrolidin-1-ylpiperidin-1-yl)carbonyl]benzenesulfonamide The titled compound was prepared as the HCl salt using first the procedure described in Example 40 substituting 2-fluoroaniline for 4-fluoroaniline and then the procedure described in Example 1 Step B: $^1$H NMR (400 MHz, DMSO-d$_6$) δ ppm 1.61 (m, 2H), 1.89 (m, 6H), 2.10 (m, 2H), 2.80 (m, 4H), 3.04 (m, 2H), 4.48 (m, 1H), 7.19 (m, 4H), 7.65 (m, 3H), 7.79 (m, 1H), 10.25 (s, 1H), 11.09 (m, 1H); MS (ESI) m/z 432 (M+H)$^+$.

Example 46

3-(1,4'-bipiperidin-1'-ylcarbonyl)-N-(4-fluorophenyl)benzenesulfonamide

To 3-(chlorosulfonyl)benzoyl chloride (0.359 g, 1.5 mmol) in anhydrous dichloromethane (80 mL) was added 1,4'-bipiperidine (0.252 g, 1.5 mmol) in dichloromethane (4 mL) slowly over 10 minutes at room temperature. Then sodium carbonate (0.32 g, 3 mmol) was added. The mixture was stirred at room temperature for 5 hours. Then 4-fluoroaniline (1.167 g, 10.5 mmol) was added. The mixture was stirred at room temperature for 3 days, then sodium carbonate (0.32 g, 3 mmol) and methanol (5 mL) were added. The mixture was stirred for 20 minutes, then filtered, and concentrated. The residue was purified by chromatography on silica gel (ethyl acetate, then methanol/ethyl acetate=1:10) to give the titled compound: $^1$H NMR (400 MHz, DMSO-d$_6$) δ ppm 1.40-1.90 (m, 10H), 2.60-3.40 (m, 8H), 4.45 (m, 1H), 7.08 (m, 4H), 7.62 (m, 3H), 7.78 (m, 1H); MS (ESI) m/z 446 (M+H)$^+$.

Example 47

3-(1,4'-bipiperidin-1'-ylcarbonyl)-N-(2-fluorophenyl)benzenesulfonamide

The titled compound was prepared using the procedure described in Example 46 substituting 2-fluoroaniline for 4-fluoroaniline: $^1$H NMR (400 MHz, DMSO-d$_6$) δ ppm 1.35-1.90 (m, 10H), 2.50-3.30 (m, 8H), 4.43 (m, 1H), 7.10 (m, 3H), 7.22 (m, 1H), 7.60 (m, 3H), 7.79 (m, 1H); MS (ESI) m/z 446 (M+H)$^+$.

Example 48

3-(1,4'-bipiperidin-1'-ylcarbonyl)-N-(3-fluorophenyl)benzenesulfonamide

The titled compound was prepared using the procedure described in Example 46 substituting 3-fluoroaniline for 4-fluoroaniline: $^1$H NMR (400 MHz, DMSO-d$_6$) δ ppm 1.30-1.90 (m, 10H), 2.50-3.20 (m, 8H), 4.42 (m, 1H), 6.82 (m, 3H), 7.21 (m, 1H), 7.63 (m, 3H), 7.82 (m, 1H); MS (ESI) m/z 446 (M−H)$^+$.

Example 49

3-(1,4'-bipiperidin-1'-ylcarbonyl)-N-[4-(trifluoromethyl)phenyl]benzenesulfonamide The titled compound was prepared using the procedure described in Example 46 substituting 4-(trifluoromethyl) aniline for 4-fluoroaniline: $^1$H NMR (400 MHz, DMSO-d$_6$) δ ppm 1.30-1.85 (m, 10H), 2.50-3.15 (m, 8H), 4.46 (m, 1H), 7.20 (d, 2H, J=8 Hz), 7.57 (d, 2H, J=8 Hz), 7.62 (m, 2H), 7.72 (s, 1H), 7.85 (m, 1H); MS (ESI) m/z 496 (M+H)$^+$.

Example 50

(8aR)-2-{[3-({4-[bis(4-fluorophenyl)methyl]piperazin-1-yl}carbonyl)phenyl]sulfonyl}octahydropyrrolo[1,2-a]pyrazine To 3-(chlorosulfonyl)benzoyl chloride (0.359 g, 1.5 mmol) in anhydrous dichloromethane (40 mL) was added 1-(bis(4-fluorophenyl)methyl)piperazine (0.433 g, 1.5 mmol) in dichloromethane (4 mL) slowly over 10 minutes at room temperature. Then sodium carbonate (0.64 g, 6 mmol) was added. The mixture was stirred at room temperature overnight. Then (R)-octahydropyrrolo[1,2-a]pyrazine (0.208 g, 1.65 mmol) was added. The mixture was stirred at reflux for 20 minutes, and then at room temperature for 3 days. Methanol (5 mL) was added, the mixture was stirred for 20 minutes, then filtered, and concentrated. The residue was purified by chromatography on silica gel (ethyl acetate/methanol=20:1) to give the titled compound: $^1$H NMR (500 MHz, DMSO-d$_6$) δ ppm 1.09 (m, 1H), 1.55 (m, 2H), 1.72 (m, 1H), 1.90 (m, 4H), 2.10 (m, 1H), 2.20-2.50 (m, 6H), 2.90 (m, 2H), 3.58-3.78 (m, 4H), 4.42 (s, 1H), 7.12 (m, 4H), 7.42 (m, 4H), 7.71 (m, 3H), 7.80 (m, 1H); MS (ESI) m/z 581 (M+H)$^+$.

Example 51

(8aS)-2-{[3-({4-[bis(4-fluorophenyl)methyl]piperazin-1-yl}carbonyl)phenyl]sulfonyl}octahydropyrrolo[1,2-a]pyrazine To 3-(chlorosulfonyl)benzoyl chloride (0.474 g, 1.981 mmol) in anhydrous dichloromethane (40 mL) was added 1-(bis(4-fluorophenyl)methyl)piperazine (0.571 g, 1.981 mmol) in dichloromethane (4 mL) slowly over 10 minutes at room temperature. Then sodium carbonate (0.64 g, 6 mmol) was added. The mixture was stirred at room temperature overnight. Then (S)-octahydropyrrolo[1,2-a]pyrazine (0.250 g, 1.981 mmol) was added. The mixture was stirred at reflux for 20 minutes and then at room temperature for 3 days. Methanol (5 mL) was added, the mixture was stirred for 20 minutes, then filtered, and concentrated. The residue was purified by chromatography on silica gel (ethyl acetate/methanol=20:1) to give the titled compound: $^1$H NMR (400 MHz, DMSO-d$_6$) δ ppm 1.07 (m, 1H), 1.55 (m, 2H), 1.71 (m, 1H), 1.95 (m, 4H), 2.08 (m, 1H), 2.28 (m, 3H), 2.39 (m, 3H), 2.85 (m, 1H), 2.92 (m, 1H), 3.57 (m, 2H), 3.74 (m, 2H), 4.45 (s, 1H), 7.13 (m, 4H), 7.45 (m, 4H), 7.66 (s, 1H), 7.70 (m, 2H), 7.80 (m, 1H); MS (ESI) m/z 581 (M+H)$^+$.

Example 52

(8aR)-2-({3-[(4-benzhydrylpiperazin-1-yl)carbonyl]phenyl}sulfonyl)octahydropyrrolo[1,2-a]pyrazine The titled compound was prepared using the procedure described in Example 50 substituting 1-benzhydrylpiperazine for 1-(bis(4-fluorophenyl)methyl)piperazine: $^1$H NMR (500 MHz, DMSO-d$_6$) δ ppm 1.07 (m, 1H), 1.57 (m, 2H), 1.72 (m, 1H), 1.92 (m, 4H), 2.09 (m, 1H), 2.25-2.50 (m, 6H), 2.90 (m, 2H), 3.60-3.78 (m, 4H), 4.39 (s, 1H), 7.18 (m, 2H), 7.30 (m, 4H), 7.62 (m, 4H), 7.70 (m, 3H), 7.80 (m, 1H); MS (ESI) m/z 545 (M+H)$^+$.

Example 53

N-(2,2-diphenylethyl)-3-[(8aS)-hexahydropyrrolo[1,2-a]pyrazin-2(1H)-ylsulfonyl]benzamide The titled compound was prepared using the procedure described in Example 51 substituting 2,2-diphenylethanamine for 1-(bis(4-fluorophenyl)methyl)piperazine: $^1$H NMR (400 MHz, DMSO-d$_6$) δ ppm 1.20 (m, 1H), 1.61 (m, 2H), 1.75 (m, 1H), 1.98 (m, 4H), 2.10 (m, 1H), 2.25 (m, 1H), 2.92 (m, 2H), 3.54 (m, 1H), 3.71 (m, 1H), 3.92 (m, 1H), 4.43 (m, 1H), 7.19 (m, 2H), 7.32 (m, 8H), 7.70 (m, 1H), 7.84 (m, 1H), 8.00 (m, 2H), 8.83 (m, 1H); MS (ESI) m/z 490 (M+H)$^+$.

Example 54

(8aS)-2-({3-[(4-benzhydrylpiperazin-1-yl)carbonyl]phenyl}sulfonyl)octahydropyrrolo[1,2-a]pyrazine The titled compound was prepared using the procedure described in Example 51 substituting 1-benzhydrylpiperazine for 1-(bis(4-fluorophenyl)methyl)piperazine: $^1$H NMR (400 MHz, DMSO-d$_6$) δ ppm 1.10 (m, 1H), 1.46 (m, 1H), 1.56 (m, 2H), 1.92 (m, 2H), 2.12 (m, 1H), 2.22 (m, 1H), 2.56 (m, 1H), 2.81 (m, 2H), 3.76 (m, 1H), 3.98 (m, 9H), 4.36 (s, 1H), 7.17 (m, 2H), 7.29 (m, 2H), 7.52 (m, 4H), 7.72 (m, 1H), 7.97 (m, 1H), 8.16 (m, 1H), 8.65 (m, 3H); MS (ESI) m/z 545 (M+H)$^+$.

Example 55

N-(3,3-diphenylpropyl)-3-[(8aS)-hexahydropyrrolo[1,2-a]pyrazin-2(1H)-ylsulfonyl]benzamide The titled compound was prepared using the procedure described in Example 51 substituting 3,3-diphenylpropan-1-amine for 1-(bis(4-fluorophenyl)methyl)piperazine: $^1$H NMR (400 MHz, DMSO-d$_6$) δ ppm 1.21 (m, 1H), 1.61 (m, 2H), 1.76 (m, 1H), 2.03 (m, 4H), 2.34 (m, 3H), 2.93 (m, 2H), 3.22 (m, 2H), 3.61 (m, 1H), 3.76 (m, 1H), 4.04 (m, 1H), 7.18 (m, 2H), 7.32 (m, 8H), 7.75 (m, 1H), 7.88 (m, 1H), 8.16 (m, 2H), 8.88 (m, 1H); MS (ESI) m/z 504 (M+H)$^+$.

Example 56

N-[2-(4-fluorophenyl)ethyl]-3-[(8aS)-hexahydropyrrolo[1,2-a]pyrazin-2(1H)-ylsulfonyl]benzamide The titled compound was prepared using the procedure described in Example 51 substituting 2-(4-fluorophenyl)ethanamine for 1-(bis(4-fluorophenyl)methyl)piperazine: $^1$H NMR (400 MHz, DMSO-d$_6$) δ ppm 1.22 (m, 1H), 1.62 (m, 2H), 1.77 (m, 1H), 2.03 (m, 4H), 2.32 (m, 1H), 2.91 (m, 4H), 3.49 (m, 2H), 3.62 (m, 1H), 3.76 (m, 1H), 7.10 (dd, 2H, J=8, 9 Hz), 7.28 (dd, 2H, J=8, 11 Hz), 7.74 (m, 1H), 7.89 (m, 1H), 8.13 (m, 2H), 8.85 (m, 1H); MS (ESI) m/z 432 (M+H)$^+$.

Example 57

3-[(8aR)-hexahydropyrrolo[1,2-a]pyrazin-2(1H)-ylcarbonyl]-N-[(1S)-2-hydroxy-1-phenylethyl]benzenesulfonamide To 3-(chlorosulfonyl)benzoyl chloride (0.359 g, 1.5 mmol) in anhydrous dichloromethane (40 mL) was added (R)-octahydropyrrolo[1,2-a]pyrazine (0.189 g, 1.5 mmol) in dichloromethane (4 mL) slowly over 10 min at room temperature. Then sodium carbonate (0.48 g, 4.52 mmol) was added. The mixture was stirred at room temperature overnight. Then (S)-2-amino-2-phenylethanol (0.274 g, 2.0 mmol) in N,N-dimethylformamide (10 mL) was added. The mixture was stirred at room temperature for 4 days. Then methanol (5 mL) was added, the mixture was stirred for 20 minutes, then filtered, and concentrated. The residue was purified by chromatography on silica gel (methanol/dichloromethane=1:12) to give the titled compound: $^1$H NMR (500 MHz, DMSO-d$_6$) δ ppm 1.30 (m, 1H), 1.60-2.10 (m, 6H), 2.80-3.10 (m, 4H), 3.40 (m, 3H), 4.25 (m, 1H), 4.40-4.60 (m, 1H), 4.82 (t, 1H, J=4 Hz), 7.10 (m, 5H), 7.44 (m, 2H), 7.60 (s, 1H), 7.65 (m, 1H), 8.30 (d, 1H, J=7 Hz); MS (ESI) m/z 430 (M+H)$^+$.

Example 58

4-chloro-2-fluoro-N-(2-fluorophenyl)-5-[(8aS)-hexahydropyrrolo[1,2-a]pyrazin-2(1H)-ylcarbonyl]benzenesulfonamide Step A:

To 2-chloro-5-(chlorosulfonyl)-4-fluorobenzoic acid (1.092 g, 4.0 mmol) was added dichloromethane (10 mL), oxalyl chloride (2.8 mL) and one small drop of N,N-dimethylformamide. The mixture was stirred at room temperature overnight. The mixture was then concentrated to give 2-chloro-5-(chlorosulfonyl)-4-fluorobenzoyl chloride which was used without additional purification.

To crude 2-chloro-5-(chlorosulfonyl)-4-fluorobenzoyl chloride (4 mmol) in anhydrous dichloromethane (100 mL) was added (S)-octahydropyrrolo[1,2-a]pyrazine (0.505 g, 4 mmol) in dichloromethane (10 mL) slowly over 10 minutes at room temperature. Then sodium carbonate (0.933 g, 8.8 mmol) was added. The mixture was stirred at room temperature overnight. Then dichloromethane was removed by concentration in vacuo, and 2-fluoroaniline (4.44 g, 40 mmol) in dichloromethane (30 mL) was added. The mixture was stirred at room temperature for 4 days. At that time, sodium carbonate (0.42 g, 4 mmol) and methanol (20 mL) were added, the mixture was stirred for 30 minutes, then filtered, and concentrated. The residue was purified by chromatography on silica gel (ethyl acetate, then methanol/ethyl acetate=1:15) to give the titled compound: $^1$H NMR (500 MHz, DMSO-d$_6$) δ ppm 1.20-1.38 (m, 1H), 1.60-2.20 (m, 7H), 2.80-3.40 (m, 4H), 4.40-4.60 (m, 1H), 7.20 (m, 4H), 7.60 (m, 1H), 7.88 (m, 1H), 10.60 (br s, 1H); MS (ESI) m/z 456 (M+H)$^+$.

Step B:

The HCl salt (1.0 equiv.) was prepared according to the procedure for Example 1 Step B: $^1$H NMR (400 MHz, DMSO-d$_6$) δ ppm 1.60-2.20 (m, 5H), 2.80-4.00 (m, 7H), 4.60-4.80 (m, 1H), 7.15-7.30 (m, 4H), 7.75-7.97 (m, 2H), 10.65 (br s, 1H), 11.60 (m, 1H); MS (ESI) m/z 456 (M+H)$^+$.

Example 59

4-chloro-N-(3,3-diphenylpropyl)-2-fluoro-5-[(8aS)-hexahydropyrrolo[1,2-a]pyrazin-2(1H)-ylcarbonyl]benzenesulfonamide The titled compound was prepared using the procedure described in Example 58 substituting 3,3-diphenylpropan-1-amine (1 equivalent) for 2-fluoroaniline: $^1$H NMR (400 MHz, DMSO-d$_6$) δ ppm 1.21 (m, 1H), 1.56 (m, 1H), 1.66 (m, 2H), 1.78 (m, 2H), 2.04 (m, 4H), 2.83 (m, 3H), 2.99 (m, 2H), 3.98 (m, 1H), 4.52 (m, 1H), 7.14 (m, 2H), 7.23 (m, 8H), 7.64 (m, 1H), 7.83 (m, 1H), 8.22 (m, 1H); MS (ESI) m/z 557 (M+H)$^+$.

Example 60

3-[(8aS)-hexahydropyrrolo[1,2-a]pyrazin-2(1H)-ylsulfonyl]-N-[(1R,2S)-2-phenylcyclopropyl]benzamide The titled compound was prepared using the procedure described in Example 51 substituting (1R,2S)-2-phenylcyclopropanamine for 1-(bis(4-fluorophenyl)methyl)piperazine: $^1$H NMR (400 MHz, DMSO-$d_6$) δ ppm 1.22 (m, 2H), 1.37 (m, 1H), 1.60 (m, 2H), 1.77 (m, 1H), 1.97 (m, 3H), 2.13 (m, 2H), 2.32 (m, 1H), 2.97 (m, 3H), 3.60 (m, 1H), 3.76 (m, 1H), 7.17 (m, 3H), 7.29 (m, 2H), 7.77 (m, 1H), 7.89 (m, 1H), 8.18 (m, 2H), 9.15 (m, 1H); (ESI) m/z 426 (M+H)$^+$.

Example 61

3-[(8aS)-hexahydropyrrolo[1,2-a]pyrazin-2(1H)-ylcarbonyl]-N-[(1R,2S)-2-phenylcyclopropyl]benzenesulfonamide The titled compound was prepared using the procedure described in Example 4 Step A substituting (1R,2S)-2-phenylcyclopropanamine (1 equivalent) for 2,6-difluoroaniline: $^1$H NMR (400 MHz, DMSO-$d_6$) δ ppm 1.11 (m, 3H), 1.64 (m, 3H), 1.86 (m, 3H), 2.05 (m, 2H), 2.27 (m, 1H), 2.83 (m, 2H), 3.00 (m, 2H), 4.50 (m, 1H), 6.90 (m, 2H), 7.12 (m, 1H), 7.19 (m, 2H), 7.67 (m, 2H), 7.72 (m, 1H), 7.83 (m, 1H), 8.28 (m, 1H); (ESI) m/z 426 (M+H)$^+$.

Example 62

4-[(8aR)-hexahydropyrrolo[1,2-a]pyrazin-2(1H)-ylcarbonyl]-N-[(1S)-2-hydroxy-1-phenylethyl]benzenesulfonamide Oxalyl chloride (2.2 mL) was added to a mixture of 4-(chlorosulfonyl)benzoic acid (0.662 g, 3.0 mmol) in anhydrous dichloromethane (25 mL) followed by one small drop of N,N-dimethylformamide. The mixture was stirred at room temperature overnight. Then the mixture was then concentrated to provide 4-(chlorosulfonyl)benzoyl chloride which was used without additional purification.

To 4-(chlorosulfonyl)benzoyl chloride (3 mmol) in anhydrous dichloromethane (100 mL) was slowly added over 10 minutes (R)-octahydropyrrolo[1,2-a]pyrazine (0.379 g, 3 mmol) at room temperature in dichloromethane (4 mL). Then sodium carbonate (0.954 g, 9 mmol) was added. The mixture was stirred at room temperature overnight. Then the reaction mixture was concentrated to provide 4-[(8aR)-hexahydropyrrolo[1,2-a]pyrazin-2(1H)-ylcarbonyl]benzenesulfonyl chloride which was used without additional purification.

Then (S)-2-amino-2-phenylethanol (0.494 g, 3.6 mmol) in dichloromethane/N,N-dimethylformamide (5:1, 40 mL) was added to the crude 4-[(8aR)-hexahydropyrrolo[1,2-a]pyrazin-2(1H)-ylcarbonyl]benzenesulfonyl chloride. The mixture was stirred at room temperature for 3 days, then sodium carbonate (0.21 g, 2 mmol) and methanol (10 mL) were added. The mixture was stirred for an additional 30 minutes, then the reaction mixture was filtered, and the filtrate was concentrated. The residue was purified by chromatography on silica gel (ethyl acetate/methanol=10:1) to give the titled compound: $^1$H NMR (500 MHz, DMSO-$d_6$) δ ppm 1.35 (m, 1H), 1.60-2.10 (m, 6H), 2.90-3.20 (m, 4H), 3.30-3.50 (m, 3H), 4.30 (m, 1H), 4.50 (m, 1H), 4.85 (m, 1H), 7.10 (m, 5H), 7.30 (m, 2H), 7.61 (m, 2H), 8.30 (br s, 1H); MS (EST) m/z 430 (M+H)$^+$.

Example 63

(8aR)-2-[2-chloro-5-(2,3-dihydro-1H-indol-1-ylsulfonyl)-4-fluorobenzoyl]octahydropyrrolo[1,2-a]pyrazine The titled compound was prepared using the procedure described in Example 58 Step A substituting (R)-octahydropyrrolo[1,2-a]pyrazine for (S)-octahydropyrrolo[1,2-a]pyrazine and substituting indoline for 2-fluoroaniline: $^1$H NMR (300 MHz, DMSO-$d_6$) δ ppm 1.20 (m, 1H), 1.35 (m, 1H), 1.60-2.20 (m, 7H), 2.70-2.90 (m, 2H), 3.00-3.10 (m, 3H), 4.05 (m, 2H), 4.40-4.60 (m, 1H), 7.00 (m, 1H), 7.18 (m, 1H), 7.21 (m, 1H), 7.36 (m, 1H), 7.90 (m, 2H); MS (ESI) m/z 463 (M+H)$^+$.

Example 64

2,4-dichloro-N-(2-fluorophenyl)-5-[(8aR)-hexahydropyrrolo[1,2-a]pyrazin-2(1H)-ylcarbonyl]benzenesulfonamide Step A:

To ethyl 2,4-dichloro-5-(chlorosulfonyl)benzoate (1 g, 3.15 mmol) in N,N-dimethylacetamide (10.5 mL) was added 2-fluoroaniline (1.215 mL, 12.60 mmol) dropwise over 1 minute at room temperature. The mixture was stirred at room temperature for 1 hour, and then it was diluted with ethyl acetate (35 mL). The organic solution was washed with 1 N HCl (2×13 mL) and saturated NaCl (13 mL). The organic layer was concentrated, ethanol (38 mL) was added, and the mixture concentrated to give ethyl 2,4-dichloro-5-{[(2-fluorophenyl)amino]sulfonyl}benzoate.

Step B:

To the product of Step A was added ethanol (8 mL) followed by a solution of NaOH (0.378 g, 9.45 mmol) in water (8 mL). The reaction was stirred at ambient temperature for 45 minutes. To the mixture was added 1 N HCl (23 mL), and the mixture was stirred overnight. The solids were collected by filtration, washed with water (1×5 mL), and dried by vacuum filtration to give 2,4-dichloro-5-{[(2-fluorophenyl)amino]sulfonyl}benzoic acid: $^1$H NMR (400 MHz, DMSO-$d_6$) δ ppm 13.50 (bs, 1H), 10.30 (bs, 1H), 8.22 (s, 1H), 8.04 (s, 1H), 7.28-7.11 (m, 4H); MS (ESI) m/z 362.3 (M−H)$^-$.

Step C:

To 2,4-dichloro-5-{[(2-fluorophenyl)amino]sulfonyl}benzoic acid (800 mg, 2.197 mmol) and 2-(3H-[1,2,3]triazolo[4,5-b]pyridin-3-yl)-1,1,3,3-tetramethylisouronium hexafluorophosphate(V) (919 mg, 2.416 mmol) in 2-methyltetrahydrofuran (15 mL) was added (R)-octahydropyrrolo[1,2-a]pyrazine (388 mg, 3.08 mmol). The reaction was stirred at room temperature for 45 minutes at which time N,N-dimethylacetamide (1 mL) was added. The reaction was stirred for an additional 45 minutes and N,N-dimethylacetamide (3 mL) was added. The reaction was stirred for an addition 2.5 hours, diluted with 2-methyltetrahydrofuran (15 mL), and washed with a solution of 6% sodium bicarbonate and 6% brine (2×15 mL). The aqueous layers were combined and re-extracted with 2-methyltetrahydrofuran (15 mL). The organic layer was washed with saturated brine (4×25 mL), dried over MgSO$_4$, and concentrated. The residue was taken up in ethanol (20 mL) and reconcentrated to give the title compound.

Step D:

To the product of Step C was added ethanol (25 mL) and then concentrated HCl (0.96 g, 2.64 mmol) in ethanol (1 mL) dropwise over 1 minute. The mixture was stirred at ambient temperature overnight and filtered. The product was washed with ethanol and dried in a vacuum oven at room temperature to yield the title compound as the hydrochloride salt: $^1$H NMR (400 MHz, DMSO-$d_6$) δ ppm 11.3-10.9 (m, 1H), 10.6 (bs, 1H), 8.1-7.2 (m, 2H), 7.3-7.05 (m, 4H), 4.82 (bs d, J=13.45, 1H), 4.0-2.8 (m, 8H), 2.33-1.48 (m, 4H); MS (ESI) m/z 472 (M+H)$^+$. Diffraction patterns were collected at ambient conditions in reflection mode using Cu—Kα1 (λ=1.54060 Å) radiation. The diffractometer is equipped with a position sensitive detector that is calibrated at 1 degree intervals using the direct beam. Calibration is verified with a NIST standard. Main characteristic diffraction peak positions (degrees 2-theta±0.1) based on a diffraction pattern collected under aforementioned conditions are as follows: 7.9, 14.1, 15.4, 15.8, 20.4, 22.1, 25.8

Example 65

N-{2-fluoro-5-[(8aR)-hexahydropyrrolo[1,2-a]pyrazin-2(1H)-ylcarbonyl]phenyl}-3-(trifluoromethyl)benzenesulfonamide Step A:
To 3-amino-4-fluorobenzoic acid (0.621 g, 4 mmol) and 1-hydroxybenzotriazole hydrate (0.613 g, 4 mmol) in dichloromethane/N,N-dimethylformamide (10:1, 60 mL) was added 1-(3-dimethylaminopropyl)-3-ethylcarbodiimide (EDC, 0.621 g, 4 mmol). After 5 minutes, (R)-octahydropyrrolo[1,2-a]pyrazine (0.505 g, 4 mmol) in dichloromethane (1 mL) was added. The mixture was stirred at room temperature overnight. Then the mixture was concentrated. The residue was purified by chromatography on silica gel (dichloromethane, then methanol/dichloromethane=1:10) to give (R)-(3-amino-4-fluorophenyl)(hexahydropyrrolo[1,2-a]pyrazin-2(1H)-yl)methanone: $^1$H NMR (500 MHz, DMSO-$d_6$) δ ppm 1.25 (m, 1H), 1.60-2.10 (m, 6H), 2.70-3.10 (m, 4H), 3.55-3.70 (m, 1H), 4.40-4.60 (m, 1H), 5.30 (s, 2H), 6.50 (m, 1H), 6.77 (m, 1H), 7.00 (m, 1H); MS (ESI) m/z 264 (M+H)$^+$.

Step B:
To (R)-(3-amino-4-fluorophenyl)(hexahydropyrrolo[1,2-a]pyrazin-2(1H)-yl)methanone (79 mg, 0.3 mmol) and sodium carbonate (64 mg, 0.6 mmol) in N,N-dimethylformamide (1 mL) was added 3-(trifluoromethyl)benzene-1-sulfonyl chloride (88 mg, 0.36 mmol) in dichloromethane (1 mL), and the mixture was stirred at room temperature for 18 hours. Then ethyl acetate was added, and the mixture was washed with water (2×10 mL). The organic phase was dried over sodium sulfate and concentrated. The residue was purified by chromatography on silica gel (methanol/dichloromethane=1:15) to give the titled compound: $^1$H NMR (500 MHz, DMSO-$d_6$) δ ppm 1.25 (m, 1H), 1.60-2.20 (m, 6H), 2.70-3.10 (m, 5H), 4.35-4.55 (m, 1H), 7.22 (m, 3H), 7.82 (m, 1H), 8.00 (m, 3H); MS (ESI) m/z 472 (M+H)$^+$.

Example 66

4-chloro-2-fluoro-N-(2-fluorophenyl)-5-[(8aR)-hexahydropyrrolo[1,2-a]pyrazin-2(1H)-ylcarbonyl]-N-methylbenzenesulfonamide The titled compound was prepared using the procedure described in Example 58 Step A substituting (R)-octahydropyrrolo[1,2-a]pyrazine for (S)-octahydropyrrolo[1,2-a]pyrazine and substituting 2-fluoro-N-methylaniline for 2-fluoroaniline: $^1$H NMR (500 MHz, DMSO-$d_6$) δ ppm 1.18-1.35 (m, 1H), 1.60-2.10 (m, 7H), 2.70-3.25 (m, 4H), 3.30 (s, 3H), 4.40-4.58 (m, 1H), 7.20-7.55 (m, 4H), 7.58 (m, 1H), 7.98 (m, 1H); MS (ESI) m/z 470 (M+H)$^+$.

Example 67

(8aR)-2-(2-chloro-4-fluoro-5-{[4-(4-fluorophenyl)piperazin-1-yl]sulfonyl}benzoyl)octahydropyrrolo[1,2-a]pyrazine The titled compound was prepared using the procedure described in Example 58 Step A substituting (R)-octahydropyrrolo[1,2-a]pyrazine for (S)-octahydropyrrolo[1,2-a]pyrazine and substituting 1-(4-fluorophenyl)piperazine for 2-fluoroaniline: $^1$H NMR (400 MHz, DMSO-$d_6$) δ ppm 1.21 (m, 1H), 1.56 (m, 1H), 1.66 (m, 3H), 2.88 (m, 3H), 2.98 (m, 4H), 3.16 (m, 4H), 3.23 (m, 4H), 4.54 (m, 1H), 6.95 (m, 2H), 7.05 (m, 2H), 7.76 (m, 1H), 7.93 (m, 1H); MS (ESI) m/z 526 (M+H)$^+$.

Example 68

N-{2-chloro-5-[(8aR)-hexahydropyrrolo[1,2-a]pyrazin-2(1H)-ylcarbonyl]phenyl}-4-fluorobenzamide Step A:
(R)-(3-Amino-4-chlorophenyl)(hexahydropyrrolo[1,2-a]pyrazin-2(1H)-yl)methanone was prepared using the procedure described in Example 65 Step A substituting 3-amino-4-chlorobenzoic acid for 3-amino-4-fluorobenzoic acid: $^1$H NMR (300 MHz, DMSO-$d_6$) δ ppm 1.30 (m, 1H), 1.60-2.10 (m, 6H), 2.70-3.10 (m, 4H), 3.55-3.70 (m, 1H), 4.40-4.60 (m, 1H), 5.50 (s, 2H), 6.49 (m, 1H), 6.76 (s, 1H), 7.21 (m, 1H); MS (ESI) m/z 280 (M+H)$^+$.

Step B:
The titled compound was prepared using the procedure described in Example 65 Step B substituting (R)-(3-amino-4-chlorophenyl)(hexahydropyrrolo[1,2-a]pyrazin-2(1H)-yl)methanone for (R)-(3-amino-4-fluorophenyl)(hexahydropyrrolo[1,2-a]pyrazin-2(1H)-yl)methanone and substituting 4-fluorobenzoyl chloride for 3-(trifluoromethyl)benzene-1-sulfonyl chloride: $^1$H NMR (500 MHz, DMSO-$d_6$) δ ppm 1.30 (m, 1H), 1.60-2.10 (m, 6H), 2.80-3.20 (m, 4H), 3.55-3.68 (m, 1H), 4.45-4.55 (m, 1H), 7.30 (m, 1H), 7.40 (m, 2H), 7.62 (m, 2H), 8.08 (m, 2H), 10.20 (s, 1H); MS (ESI) m/z 402 (M+H)$^+$.

Example 69

N-{3-[(8aR)-hexahydropyrrolo[1,2-a]pyrazin-2(1H)-ylcarbonyl]phenyl}-N-methyl-3-(trifluoromethyl)benzenesulfonamide Step A:
(R)-(3-Amino-4-methylphenyl)(hexahydropyrrolo[1,2-a]pyrazin-2(1H)-yl)methanone was prepared using the procedure described in Example 65 Step A substituting 3-(methylamino)benzoic acid for 3-amino-4-fluorobenzoic acid: $^1$H NMR (300 MHz, DMSO-$d_6$) δ ppm 1.25 (m, 1H), 1.60-1.85 (m, 4H), 2.00 (m, 2H), 2.65 (d, 3H, J=6 Hz), 2.70-3.10 (m, 4H), 3.56-3.70 (m, 1H), 4.40-4.55 (m, 1H), 5.82 (m, 1H), 6.48 (m, 2H), 6.58 (m, 1H), 7.11 (m, 1H); MS (ESI) m/z 260 (M+H)$^+$.

Step B:
The title compound was prepared using the procedure described in Example 65 Step B substituting (R)-(3-amino-4-methylphenyl)(hexahydropyrrolo[1,2-a]pyrazin-2(1H)-yl)

methanone for (R)-(3-amino-4-fluorophenyl)(hexahydropyrrolo[1,2-a]pyrazin-2(1H)-yl)methanone: $^1$H NMR (500 MHz, DMSO-d$_6$) δ ppm 1.29 (m, 1H), 1.65-2.10 (m, 6H), 2.75-3.05 (m, 4H), 3.20 (s, 3H), 3.40-3.50 (m, 1H), 4.40-4.55 (m, 1H), 7.10-7.25 (m, 2H), 7.33 (m, 1H), 7.42 (m, 1H), 7.62 (m, 1H), 7.82 (m, 2H), 8.15 (m, 1H); MS (ESI) m/z 468 (M+H)$^+$.

Example 70

4-chloro-N-(2,2-diphenylethyl)-2-fluoro-5-[(8aR)-hexahydropyrrolo[1,2-a]pyrazin-2(1H)-ylcarbonyl]benzenesulfonamide The titled compound was prepared using the procedure described in Example 58 Step A substituting (R)-octahydropyrrolo[1,2-a]pyrazine for (S)-octahydropyrrolo[1,2-a]pyrazine and substituting 2,2-diphenylethanamine for 2-fluoroaniline: $^1$H NMR (400 MHz, DMSO-d$_6$) δ ppm 1.20 (m, 1H), 1.56 (m, 1H), 1.67 (m, 3H), 2.89 (m, 3H), 2.97 (m, 4H), 3.56 (m, 2H), 4.12 (m, 1H), 4.53 (m, 1H), 7.11 (m, 10H), 7.66 (m, 2H), 8.28 (m, 1H); MS (ESI) m/z 543 (M+H)$^+$.

Example 71

N-{2-chloro-4-[(8aR)-hexahydropyrrolo[1,2-a]pyrazin-2(1H)-ylcarbonyl]phenyl}-4-fluorobenzamide Step A:
(R)-(4-Amino-3-chlorophenyl)(hexahydropyrrolo[1,2-a]pyrazin-2(1H)-yl)methanone was prepared using the procedure described in Example 65 Step A substituting 4-amino-3-chlorobenzoic acid for 3-amino-4-fluorobenzoic acid: $^1$H NMR (300 MHz, DMSO-d$_6$) δ ppm 1.28 (m, 1H), 1.70 (m, 4H), 2.00 (m, 2H), 2.65 (m, 1H), 3.00 (m, 3H), 4.00-4.20 (m, 2H), 5.77 (s, 2H), 6.79 (d, 1H, J=8 Hz), 7.09 (d, 1H, J=8 Hz), 7.22 (s, 1H); MS (ESI) m/z 280 (M+H)$^+$.

Step B:
The titled compound was prepared using the procedure described in Example 65 Step B substituting (R)-(4-amino-3-chlorophenyl)(hexahydropyrrolo[1,2-a]pyrazin-2(1H)-yl)methanone for (R)-(3-amino-4-fluorophenyl)(hexahydropyrrolo[1,2-a]pyrazin-2(1H)-yl)methanone and substituting 4-fluorobenzoyl chloride for 3-(trifluoromethyl)benzene-1-sulfonyl chloride: $^1$H NMR (500 MHz, DMSO-d$_6$) δ ppm 1.30 (m, 1H), 1.60-2.06 (m, 6H), 2.80-3.20 (m, 4H), 3.50-3.62 (m, 1H), 4.40-4.60 (m, 1H), 7.39 (m, 3H), 7.57 (s, 1H), 7.65 (m, 1H), 8.05 (m, 2H), 10.18 (s, 1H); MS (ESI) m/z 402 (M+H)$^+$.

Example 72

N-{4-[(8aR)-hexahydropyrrolo[1,2-a]pyrazin-2(1H)-ylcarbonyl]-2-methylphenyl}-2-naphthamide The titled compound was prepared using the procedure described in Example 65 substituting 4-amino-3-methylbenzoic acid for 3-amino-4-fluorobenzoic acid in Step A and substituting 2-naphthoyl chloride for 3-(trifluoromethyl)benzene-1-sulfonyl chloride in Step B: $^1$H NMR (500 MHz, DMSO-d$_6$) δ ppm 1.30 (m, 1H), 1.60-2.10 (m, 6H), 2.33 (s, 3H), 2.80-3.20 (m, 4H), 3.58-3.70 (m, 1H), 4.45-4.55 (m, 1H), 7.22 (m, 1H), 7.36 (m, 1H), 7.50 (m, 1H), 7.62 (m, 2H), 8.10 (m, 4H), 8.60 (s, 1H), 10.15 (s, 1H); MS (ESI) m/z 414 (M+H)$^+$.

Example 73

3,5-dichloro-N-{2-fluoro-5-[(8aR)-hexahydropyrrolo[1,2-a]pyrazin-2(1H)-ylcarbonyl]phenyl}benzamide The titled compound was prepared using the procedure described in Example 65 Step B substituting 3,5-dichlorobenzoyl chloride for 3-(trifluoromethyl)benzene-1-sulfonyl chloride: $^1$H NMR (500 MHz, DMSO-d$_6$) ppm 1.30 (m, 1H), 1.60-2.20 (m, 6H), 2.80-3.20 (m, 4H), 3.55-3.70 (m, 1H), 4.40-4.58 (m, 1H), 7.36 (m, 1H), 7.40 (m, 1H), 7.67 (m, 1H), 7.91 (s, 1H), 8.00 (s, 2H), 10.45 (s, 1H); MS (ESI) m/z 436 (M+H)$^+$.

Example 74

N-benzhydryl-4-chloro-2-fluoro-5-[(8aR)-hexahydropyrrolo[1,2-a]pyrazin-2(1H)-ylcarbonyl]benzenesulfonamide The titled compound was prepared using the procedure described in Example 58 Step A substituting (R)-octahydropyrrolo[1,2-a]pyrazine for (S)-octahydropyrrolo[1,2-a]pyrazine and substituting diphenylmethanamine for 2-fluoroaniline: $^1$H NMR (400 MHz, DMSO-d$_6$) ppm 1.05 (m, 1H), 1.33 (m, 1H), 1.67 (m, 2H), 1.93 (m, 5H), 2.94 (m, 3H), 4.33 (m, 1H), 4.61 (m, 1H), 7.22 (m, 10H), 7.46 (m, 1H), 7.61 (m, 1H), 9.41 (m, 1H); MS (ESI) m/z 529 (M+H)$^+$.

Example 75

N-{2-chloro-4-[(8aR)-hexahydropyrrolo[1,2-a]pyrazin-2(1H)-ylcarbonyl]phenyl}-2,2-diphenylacetamide The titled compound was prepared using the procedure described in Example 65 substituting 4-amino-3-chlorobenzoic acid for 3-amino-4-fluorobenzoic acid in Step A and substituting 2,2-diphenylacetyl chloride for 3-(trifluoromethyl)benzene-1-sulfonyl chloride in Step B: $^1$H NMR (500 MHz, DMSO-d$_6$) δ ppm 1.30 (m, 1H), 1.60-2.10 (m, 6H), 2.80-3.20 (m, 4H), 3.50-3.60 (m, 1H), 4.40-4.55 (m, 1H), 5.45 (s, 1H), 7.25-7.40 (m, 11H), 7.52 (s, 1H), 7.82 (m, 1H), 10.00 (s, 1H); MS (ESI) m/z 474 (M+H)$^+$.

Example 76

N-{2-chloro-4-[(8aR)-hexahydropyrrolo[1,2-a]pyrazin-2(1H)-ylcarbonyl]phenyl}-2-naphthamide The titled compound was prepared using the procedure described in Example 65 substituting 4-amino-3-chlorobenzoic acid for 3-amino-4-fluorobenzoic acid in Step A and substituting 2-naphthoyl chloride for 3-(trifluoromethyl)benzene-1-sulfonyl chloride in Step B: $^1$H NMR (500 MHz, DMSO-d$_6$) δ ppm 1.30 (m, 1H), 1.60-2.10 (m, 6H), 2.80-3.20 (m, 4H), 3.55-3.70 (m, 1H), 4.45-4.55 (m, 1H), 7.42 (m, 1H), 7.60-7.75 (m, 4H), 8.08 (m, 4H), 8.62 (s, 1H), 10.30 (s, 1H); MS (ESI) m/z 434 (M+H)$^+$.

Example 77

N-{3-[(8aR)-hexahydropyrrolo[1,2-a]pyrazin-2(1H)-ylcarbonyl]phenyl}-N-isopropyl-3-(trifluoromethyl)benzenesulfonamide Step A:

Potassium phosphate (1.38 g, 6.5 mmol), palladium(II) acetate (56 mg, 0.25 mmol), and (R)-1-[(S)-2-(dicyclohexylphosphino)ferrocenyl]ethyl-di-tert-butylphosphine (139 mg, 0.25 mmol) were combined in a microwave tube under nitrogen. Ethyl 3-bromobenzoate (1.145 g, 5 mmol) in dimethoxyethane (2 mL) and isopropylamine (385 mg, 6.5 mmol) in dimethoxyethane (2 mL) were added. The tube was filled with nitrogen again. The tube was then capped, and the reaction mixture was heated in a microwave oven (Biotage Initiator™ 2.0, 0 to 100 watts) with stirring at 160° C. for 70 minutes. Then dichloromethane was added, and the crude mixture was filtered. The filtrate was concentrated. The residue was purified by chromatography on silica gel (hexane/ethyl acetate=7:1) to give ethyl 3-(isopropylamino)benzoate.

Step B:

To ethyl 3-(isopropylamino)benzoate (540 mg, 2.412 mmol in pyridine (0.7 mL) was added 3-(trifluoromethyl)benzene-1-sulfonyl chloride (1.08 g, 4.43 mmol), and the mixture was stirred at 90° C. for 18 hours. The mixture was diluted with ethyl acetate (60 mL) and washed with water (3×15 mL). The organic phase was dried over sodium sulfate and concentrated. The residue was purified by chromatography on silica gel (hexane/ethyl acetate=7:1) to give 3-(N-isopropyl-3-(trifluoromethyl)phenylsulfonamido)benzoate: $^1$H NMR (300 MHz, CDCl$_3$) δ ppm 1.08 (d, 6H, J=8 Hz), 1.38 (t, 3H, J=8 Hz), 4.38 (t, 2H, J=8 Hz), 4.62 (m, 1H), 7.24 (m, 1H), 7.45 (m, 1H), 7.62 (m, 2H), 7.82 (m, 1H), 7.95 (m, 2H), 8.15 (m, 1H); MS (ESI) m/z 416 (M+H)$^+$.

Step C:

To ethyl 3-(N-isopropyl-3-(tri fluoromethyl)phenylsulfonamido)benzoate (330 mg, 0.794 mmol) in ethanol (5 mL) was added 2 N KOH solution (2.4 mL). The mixture was stirred at room temperature for 3 days, and then 4 N HCl solution (1.3 mL) was added. The mixture was concentrated until the water was gone. Then dichloromethane/methanol (50:1, 50 mL) was added, the solution was filtered, and the filtrate was concentrated to give 3-(N-isopropyl-3-(trifluoromethyl)phenylsulfonamido)benzoic acid: $^1$H NMR (300 MHz, DMSO-d$_6$) δ ppm 1.00 (d, 6H, J=8 Hz), 4.62 (m, 1H), 7.30 (m, 1H), 7.45 (s, 1H), 7.60 (m, 1H), 7.80-8.10 (m, 5H), 13.18 (br s, 1H); MS (ESI) m/z 416 (M−H)$^−$.

Step D:

To a mixture of 3-(N-isopropyl-3-(trifluoromethyl)phenylsulfonamido)benzoic acid (155 mg, 0.4 mmol) and 1-hydroxybenzotriazole hydrate (61 mg, 0.4 mmol) in dichloromethane/N,N-dimethylformamide (4:1, 6 mL) was added 1-(3-dimethylaminopropyl)-3-ethylcarbodiimide (EDC, 62 mg, 0.4 mmol) in dichloromethane (1 mL). After 5 minutes, (R)-octahydropyrrolo[1,2-a]pyrazine (50 mg, 0.4 mmol) in dichloromethane (1 mL) was added. The mixture was stirred at room temperature overnight. Then the mixture was concentrated. The residue was diluted with ethyl acetate (100 mL), washed with water (2×20 mL), dried over sodium sulfate, and concentrated. The residue was purified by chromatography on silica gel (dichloromethane, then methanol/dichloromethane=1:12) to give the titled compound: $^1$H NMR (300 MHz, DMSO-d$_6$) δ ppm 1.00 (d, 6H, J=8 Hz), 1.35 (m, 1H), 1.65-2.10 (m, 6H), 2.80-3.05 (m, 4H), 3.45-3.55 (m, 1H), 4.40-4.50 (m, 1H), 4.60 (m, 1H), 6.98 (s, 1H), 7.15 (m, 1H), 7.50 (m, 2H), 7.88 (m, 2H), 8.10 (m, 2H); MS (ESI) m/z 496 (M+H)$^+$.

Example 78

N-{2-chloro-5-[(8aR)-hexahydropyrrolo[1,2-a]pyrazin-2(1H)-ylcarbonyl]phenyl}-2,2-diphenylacetamide The titled compound was prepared using the procedure described in Example 65 substituting 3-amino-4-chlorobenzoic acid for 3-amino-4-fluorobenzoic acid in Step A and substituting 2,2-diphenylacetyl chloride for 3-(trifluoromethyl)benzene-1-sulfonyl chloride in Step B: $^1$H NMR (500 MHz, DMSO-d$_6$) δ ppm 1.30 (m, 1H), 1.60-2.10 (m, 6H), 2.80-3.20 (m, 4H), 3.55-3.65 (m, 1H), 4.40-4.55 (m, 1H), 5.42 (s, 1H), 7.20-7.40 (m, 11H), 7.60 (m, 1H), 7.77 (s, 1H), 10.00 (s, 1H); MS (ESI) m/z 474 (M+H)$^+$.

Example 79

N-benzhydryl-N-{2-chloro-5-[(8aR)-hexahydropyrrolo[1,2-a]pyrazin-2(1H)-ylcarbonyl]phenyl}amine The titled compound was prepared using the procedure described in Example 65 substituting 3-amino-4-chlorobenzoic acid for 3-amino-4-fluorobenzoic acid in Step A and substituting (bromomethylene)dibenzene for 3-(trifluoromethyl)benzene-1-sulfonyl chloride in Step B. In this instance, the Step B reaction was performed with heating in a microwave oven (Biotage Initiator™ 2.0, 0 to 100 watts) at 120° C. for 40 minutes: $^1$H NMR (500 MHz, DMSO-d$_6$) δ ppm 1.10 (m, 1H), 1.50-2.00 (m, 6H), 2.40-2.90 (m, 4H), 3.20 (m, 1H), 4.35-4.50 (m, 1H), 5.43 (m, 1H), 5.82 (m, 1H), 6.50 (s, 1H), 6.60 (m, 1H), 7.25-7.55 (m, 11H); MS (ESI) m/z 446 (M+H)$^+$.

Example 80

N-benzhydryl-N-{3-[(8aR)-hexahydropyrrolo[1,2-a]pyrazin-2(1H)-ylcarbonyl]phenyl}amine The titled compound was prepared using the procedure described in Example 65 substituting 3-aminobenzoic acid for 3-amino-4-fluorobenzoic acid in Step A and substituting (bromomethylene)dibenzene for 3-(trifluoromethyl)benzene-1-sulfonyl chloride in Step B. In this instance, the Step B reaction was performed with heating in a microwave oven (Biotage Initiator™ 2.0, 0 to 100 watts) at 120° C. for 40 minutes: $^1$H NMR (500 MHz, DMSO-d$_6$) δ ppm 1.20 (m, 1H), 1.60-2.00 (m, 6H), 2.60-2.95 (m, 4H), 3.40 (m, 1H), 4.35-4.50 (m, 1H), 5.64 (m, 1H), 6.45 (m, 1H), 6.55 (s, 1H), 6.60 (m, 1H), 6.76 (m, 1H), 7.09 (m, 1H), 7.20-7.45 (m, 10H); MS (ESI) m/z 412 (M+H)$^+$.

Example 81

3-[(8aR)-hexahydropyrrolo[1,2-a]pyrazin-2(1H)-ylsulfonyl]-N-[(1S)-2-hydroxy-1-phenylethyl]benzamide The titled compounds was prepared using the procedure described in Example 1 Step A substituting (S)-2-amino-2-phenylethanol for (R)-octahydropyrrolo[1,2-a]pyrazine and substituting (R)-octahydropyrrolo[1,2-a]pyrazine for 4-(trifluoromethyl)aniline: $^1$H NMR (500 MHz, DMSO-d$_6$) δ ppm 1.20 (m, 1H), 1.60 (m, 2H), 1.80 (m, 1H), 1.90-2.08 (m, 3H), 2.15 (m, 1H), 2.35 (m, 1H), 2.90 (m, 1H), 2.98 (m, 1H), 3.60-3.80 (m, 4H), 5.00 (m, 1H), 5.10 (m, 1H), 7.20-7.40 (m, 5H), 7.78 (m, 1H), 7.95 (m, 1H), 8.22 (m, 2H), 9.08 (m, 1H); MS (ESI) m/z 430 (M+H)$^+$.

Example 82

N-benzhydryl-2-chloro-4-fluoro-5-[(8aS)-hexahydropyrrolo[1,2-a]pyrazin-2(1H)-ylsulfonyl]benzamide The titled compound was prepared using the procedure described in Example 58 Step A substituting diphenylmethanamine for (S)-octahydropyrrolo[1,2-a]pyrazine and substituting (S)-octahydropyrrolo[1,2-a]pyrazine for 2-fluoroaniline: $^1$H NMR (400 MHz, DMSO-d$_6$) δ ppm 1.24 (m, 1H), 1.63 (m, 2H), 1.79 (m, 1H), 1.94 (m, 1H), 2.07 (m, 3H), 2.33 (m, 1H), 2.62 (m, 1H), 2.96 (m, 2H), 3.63 (m, 1H), 3.77 (m, 1H), 6.31 (m, 1H), 7.28 (m, 3H), 7.37 (m, 6H), 7.70 (m, 1H), 7.81 (m, 1H), 9.59 (m, 1H); MS (ESI) m/z 529 (M+H)$^+$.

Example 83

2-chloro-N-cyclopropyl-4-fluoro-5-[(8aS)-hexahydropyrrolo[1,2-a]pyrazin-2(1H)-ylsulfonyl]benzamide The titled compound was prepared using the procedure described in Example 58 Step A substituting cyclopropanamine for (S)-octahydropyrrolo[1,2-a]pyrazine and substituting (S)-octahydropyrrolo[1,2-a]pyrazine for 2-fluoroaniline: $^1$H NMR (400 MHz, DMSO-d$_6$) δ ppm 0.54 (m, 2H), 0.70 (m, 2H), 1.24 (m, 1H), 1.63 (m, 2H), 1.78 (m, 1H), 1.93 (m, 1H), 2.08 (m, 2H), 2.34 (m, 1H), 2.64 (m, 1H), 2.80 (m, 1H), 2.97 (m, 2H), 3.65 (m, 1H), 3.78 (m, 1H), 7.72 (m, 1H), 7.86 (m, 1H), 8.65 (m, 1H); MS (ESI) m/z 402 (M+H)$^+$.

Many variations in the invention suggest themselves to those skilled in the art in light of the foregoing detailed description. All such obvious variations are within the full intended scope of the appended claims.

We claim:

1. A compound that is 4-chloro-2-fluoro-N-(2-fluorophenyl)-5-[(8aR)-hexahydropyrrolo[1,2-a]pyrazin-2(1H)-ylcarbonyl]-benzenesulfonamide, or a pharmaceutically acceptable salt thereof.

2. A pharmaceutical composition comprising a therapeutically effective amount of 4-chloro-2-fluoro-N-(2-fluorophenyl)-5-[(8aR)-hexahydropyrrolo[1,2-a]pyrazin-2(1H)-ylcarbonyl]-benzenesulfonamide, or a pharmaceutically acceptable salt thereof, in combination with a pharmaceutically acceptable carrier.

* * * * *